US008101385B2

(12) United States Patent
Cload et al.

(10) Patent No.: US 8,101,385 B2
(45) Date of Patent: Jan. 24, 2012

(54) MATERIALS AND METHODS FOR THE GENERATION OF TRANSCRIPTS COMPRISING MODIFIED NUCLEOTIDES

(75) Inventors: Sharon Cload, Cambridge, MA (US); John L. Diener, Cambridge, MA (US); Anthony Dominic Keefe, Cambridge, MA (US); Kristin Thompson, Arlington, MA (US)

(73) Assignee: Archemix Corp., Cambridge, MA (US)

( * ) Notice: Subject to any disclaimer, the term of this patent is extended or adjusted under 35 U.S.C. 154(b) by 744 days.

(21) Appl. No.: 12/004,626

(22) Filed: Dec. 21, 2007

(65) Prior Publication Data

US 2010/0120024 A1 May 13, 2010

Related U.S. Application Data

(63) Continuation-in-part of application No. 11/480,188, filed on Jun. 30, 2006.

(60) Provisional application No. 60/696,292, filed on Jun. 30, 2005, provisional application No. 60/876,780, filed on Dec. 22, 2006, provisional application No. 60/879,830, filed on Jan. 10, 2007.

(51) Int. Cl.
*C12P 19/34* (2006.01)
*C12N 9/12* (2006.01)

(52) U.S. Cl. ................... 435/91.1; 435/91.3; 435/91.21; 435/6

(58) Field of Classification Search ........................ None
See application file for complete search history.

(56) References Cited

U.S. PATENT DOCUMENTS

| | | | | |
|---|---|---|---|---|
| 5,270,163 | A | 12/1993 | Gold et al. | 435/6 |
| 5,385,834 | A | 1/1995 | Ikeda | 435/172.3 |
| 5,475,096 | A | 12/1995 | Gold et al. | 536/23.1 |
| 5,496,938 | A | 3/1996 | Gold et al. | 536/22.1 |
| 5,567,588 | A | 10/1996 | Gold et al. | 435/6 |
| 5,580,737 | A | 12/1996 | Polisky et al. | 435/6 |
| 5,637,459 | A | 6/1997 | Burke et al. | 435/6 |
| 5,648,214 | A | 7/1997 | Nieuwlandt et al. | 435/6 |
| 5,660,985 | A | 8/1997 | Pieken et al. | 435/6 |
| 5,668,264 | A | 9/1997 | Janjic et al. | 536/23.1 |
| 5,672,695 | A | 9/1997 | Eckstein et al. | 536/24.5 |
| 5,674,685 | A | 10/1997 | Janjic et al. | 435/6 |
| 5,683,867 | A | 11/1997 | Biesecker et al. | 435/6 |
| 5,698,687 | A | 12/1997 | Eckstein et al. | 536/25.3 |
| 5,705,537 | A | 1/1998 | Hartman, Jr. et al. | 521/84.1 |
| 5,707,796 | A | 1/1998 | Gold et al. | 435/6 |
| 5,763,177 | A | 6/1998 | Gold et al. | 435/6 |
| 5,817,635 | A | 10/1998 | Eckstein et al. | 514/44 |
| 5,827,661 | A | 10/1998 | Blais | 435/6 |
| 5,861,254 | A | 1/1999 | Schneider et al. | 435/6 |
| 5,869,320 | A | 2/1999 | Studier et al. | 435/252.33 |
| 5,958,691 | A | 9/1999 | Pieken et al. | 435/6 |
| 6,011,020 | A | 1/2000 | Gold et al. | 514/44 |
| 6,051,698 | A | 4/2000 | Janjic et al. | 536/24.31 |
| 6,207,646 | B1 | 3/2001 | Krieg et al. | 514/44 |
| 6,207,816 | B1 | 3/2001 | Gold et al. | 536/24.1 |
| 6,214,806 | B1 | 4/2001 | Krieg et al. | 514/44 |
| 6,229,002 | B1 | 5/2001 | Janjic et al. | 536/23.1 |
| 6,239,116 | B1 | 5/2001 | Krieg et al. | 514/44 |
| 6,366,530 | B1 | 4/2002 | Sluiter et al. | 365/240 |
| 6,426,434 | B1 | 7/2002 | Yoshida et al. | 564/71 |
| 6,429,199 | B1 | 8/2002 | Krieg et al. | 514/44 |
| 6,498,148 | B1 | 12/2002 | Raz | 514/44 |
| 6,514,948 | B1 | 2/2003 | Raz et al. | 514/44 |
| 6,562,575 | B1 | 5/2003 | Dahl | 435/6 |
| 6,653,292 | B1 | 11/2003 | Krieg et al. | 514/44 |
| 6,867,027 | B1 | 3/2005 | Hayashizaki et al. | 435/194 |
| 7,022,144 | B2 | 4/2006 | Legrand et al. | 8/405 |
| 7,335,471 | B2 | 2/2008 | Guillerez et al. | 435/6 |
| 2004/0180360 | A1 | 9/2004 | Wilson et al. | 435/6 |
| 2004/0197804 | A1 | 10/2004 | Keefe et al. | 435/6 |
| 2005/0037394 | A1 | 2/2005 | Keefe et al. | 435/6 |
| 2005/0069907 | A1 | 3/2005 | Sousa | |
| 2006/0183702 | A1 | 8/2006 | Diener et al. | 514/44 A |
| 2007/0117112 | A1 | 5/2007 | Diener et al. | 435/6 |
| 2009/0081679 | A1 | 3/2009 | Keefe et al. | 435/6 |

FOREIGN PATENT DOCUMENTS

| | | |
|---|---|---|
| WO | WO 91/19813 | 12/1991 |
| WO | WO 92/07065 | 4/1992 |
| WO | WO 98/18480 | 5/1998 |

OTHER PUBLICATIONS

Ngo et al. In The Protein Folding Problem and Tertiary Structure Prediction, 1994, Merz et al. (ed.), Birkhauser, Boston, MA, pp. 433 and 492-495.*

Bradford, M.M., "A Rapid and Sensitive Method for the Quantitation of Microgram Quantities of Protein Utilizing the Principle of Protein-Dye Binding", *Anal. Biochem.*, 72:248-254 (1976).

Bull et al., "Experimental Evolution Yields Hundreds of Mutations in a Functional Viral Genome", *J. Mol. Evol.*, 57:241-248 (2003).

Burmeister et al., "Direct In Vitro Selection of a 2'-O-Methyl Aptamer To VEGF", *Chem. Biol.*, 12:25-33 (2005).

Chelliserrykattil et al., "Evolution of a T7 RNA polymerase variant that transcribes 2'-O-methyl RNA", *Nat. Biotech.*, 22(9):1155-1160 (2004).

Cotton et al., "2'-O-methyl, 2'-O-ethyl oligoribonudeotides and phosphorothioate oligodeoxyribonucleotides as inhibitors of the in vitro U7 snRNP-dependent mRNA processing event", *Nuc. Acids Res.*, 19(10):2629-2635 (1991).

Froehler et al., "Synthesis of DNA via deoxynucleoside H-phosphonate Intermediates", *Nuc. Acids Res.*, 14(13):5399-5407 (1986).

Froehler, B.C., "Deoxynucleoside H-Phosphonate Diester intermediates in the Synthesis of Internucleotide Phosphate Analogues", *Tet. Letters*, 27(46):5575-5578 (1986).

Greenwald et al., "Highly Water Soluble Taxol Derivatives: 7-Polyethylene Glycol Carbamates and Carbonates", *J. Org. Chem.*, 60:331-336 (1995).

(Continued)

*Primary Examiner* — Richard Hutson

(74) *Attorney, Agent, or Firm* — Mintz Levin Cohn Ferris Glovsky and Popeo, P.C.; Ivor R. Elrifi

(57) ABSTRACT

Materials and methods are provided for producing aptamer therapeutics having modified nucleotide triphosphates incorporated into their sequence.

24 Claims, 14 Drawing Sheets

OTHER PUBLICATIONS

Guillerez et al., "A mutation in T7 RNA polymerase that facilitates promoter clearance", *PNAS*, 102(17):5958-5963 (2005).

Harris et al., "Effect of Pegylation on Pharmaceuticals", *Nat. Rev.*, 2:214-221 (2003).

Hirose et al., "Rapid Synthesis of Trideoxyribonucleotide Blocks", *Tet. Letters*, 28:2449-2452 (1978).

Hobbs et al., "Polynucleotides containing 2'-amino-2'-deoxyribose and 2'-azido-2'-deoxyribose", *Biochem.*, 12(25):5138-5145 (1973).

Krieg, A.M., "CPG Motifs in Bacterial DNA and Their Immune Effects", *Annu. Rev. Immunol.*, 20:709-760 (2002).

Padilla et al., "A Y639F/H784A T7 RNA polymerase double mutant displays superior properties for synthesizing RNAs with non-canonical NTPs", *Nuc. Acids Res.*, 30(24):e138 (2002).

Padilla et al., "Efficient synthesis of nucleic acids heavily modified with non-canonical ribose 2'-groups using a mutant T7 RNA polymerase (RNAP)", *Nuc. Acids Res.*, 27(6):1561-1563 (1999).

Pietersz et al., "A 16-mer peptide (RQIKIWFQNRRMKWKK) from antennapedia preferentially targets the Class I pathway", *Vaccine*, 19:1397-1405 (2001).

Rothbard et al., "Arginine-Rich Molecular Transporters for Drug Delivery: Role of Backbone Spacing in Cellular Uptake", *J. Med. Chem.*, 45(17):3612-3618 (2002).

Rothbard et al., "Conjugation of arginine oligomers to cyclosporine A facilitates topical delivery and inhibition of inflammation", *Nat. Med.*, 6(11)1253-1257 (2000).

Ruckman et al., "2'-Fluoropyrimidine RNA-based Aptamers to the 165-Amino Acid Form of Vascular Endothelial Growth Factor ($VEGF_{165}$)", *J. Biol. Chem.*, 273(32):20556-20567 (1998).

Sood et al., "A rapid and convenient synthesis of poly-thymidylic acid by the modified trimester approach", *Nuc. Acids Res.*, 4(8):2757-2765 (1977).

Sproat et al., "New synthetic routes to synthons suitable for 2'-O'allyloligoribonucleotide assembly", *Nuc. Acids Res.*, 19(4):733-738 (1990).

Tucker et al., "Detection and plasma pharmacokinetics of an anti-vascular endothelial growth factor ofigonucleotide-aptamer (NX1838) in rhesus monkeys", *J. Chromatograph. B.*, 732:203-212 (1999).

Vives et al., "A Truncated HIV-1 Tat Protein Basic Domain Rapidly Translocates through the Plasma Membrane and Accumulates in the Cell Nucleus", *J. Biol. Chem.*, 272(25):16010-16017 (1997).

Dewey et al., "New uridine derivatives for systematic evolution of RNA ligands by exponential enrichment", *J. Am. Chem. Soc.*, 117:8474-8475 (1995).

Ebara et al., "Construction of nonnatural DNA library", *Nucl. Acids Symposium*, Series No. 2:175-176 (1999).

Gugliotti et al., "RNA-mediated control of metal nanoparticle shape", *J. Am. Chem. Soc.*, 127:17814-17818 (2005).

Gugliotti et al., "RNA-mediated metal-metal bond formation in the synthesis of hexagonal palladium nanoparaticles", *Science*, 304:850-852 (2004).

Ito et al., "Synthesis, thermal stability and resistance to enzymatic hydrolysis of the oligonucleotides containing 5-(N-aminohexyl)carbamoyl-2'-O-methyluridines", *Nucl. Acids Res.*, 31(10):2514-2523 (2003).

Ito, Y., "Modified nucleic acids for in vitro selection", *Nucl. Acids Symposium*, Series 37:259-260 (1997).

Jager et al., "A versatile toolbox for variable DNA fictionalization at high density", *J. Am. Chem. Soc.*, 127:15071-15082 (2005).

Kuwahara et al., "Direct PCR amplification of various modified DNAs having amino acids: convenient preparation of DNA libraries with high-potential activities for in vitro selection", *Bioorg. Med. Chem.*, 14:2518-2526 (2006).

Kuwahara et al., "Enzymatic incorporation of chemically-modified nucleotides into DNAs", *Nucl. Acids Res., Suppl.* 2:83-84 (2002).

Kuwahara et al., "Systematic characterization of 2'-deoxynucleoside-5'-triphosphate analogs as substrates for DNA polymerases by polymerase chain reaction and kinetic studies on enzymatic production of modified DNA", *Nucl. Acids Res.*, 34(19):5383-5394 (2006).

Liu et al., "RNA-Mediated synthesis of palladium nanoparticles on Au surfaces", *Langmuir*, 22:5862-5866 (2006).

Masud et al., "Enzymatic synthesis of modified DNA by PCR", *Nucl. Acids Res.*, Suppl. 1:21-22 (2001).

Masud et al., "Modified DNA bearing 5-(Methoxycarbonyl-methyl)-2'-deoxyuridine: preparation by PCR with thermophilic DNA polymerase and post-synthetic derivatization", *ChemBioChem.*, 4:584-588 (2003).

Nieuwlandt et al., "The first example of an RNA urea synthase: selection through the enzyme active site of human neutrophile elastase", *ChemBioChem.*, 4:651-654 (2003).

Obayashi et al., "Enzymatic synthesis of labeled DNA by PCR using new fluorescent thymidine nucleotide analogue and superthermophilic KOD dash DNA polymerase", *Bioorg. Med. Chem. Lett.*, 12:1167-1170 (2002).

Ohbayashi et al., "Expansion of repertoire of modified DNAs prepared by PCR using KOD dash DNA polymerase", *Org. Biomol. Chem.*, 3:2463-2468 (2005).

Saitoh et al., "Modified DNA aptamers against sweet agent aspartame", *Nucl. Acids Res.*, Suppl. 2:215-216 (2002).

Sawai et al., "Synthesis of new modified DNAs by hyperthermophilic DNA polymerase: substrate and template specificity of functionalized thymidine analogues bearing an sp3-hybridized carabon at the C5 α-position for several DNA polymerases", *Bioconj. Chem.*, 13:309-316 (2002).

Schoetzau et al., "Aminomodified nucleobases: functionalized nucleoside triphosphates applicable for SELEX", *Bioconj. Chem.*, 14:919-926 (2003).

Shoji et al., "Chemico-enzymatic synthesis of a new fluorescent-labeled DNA by PCR with a thymidine nucleotide analogue bearing an acridone derivative", *Bioorg. Med. Chem. Lett.*, 17:776-779 (2007).

Tarasow et al., "RNA-catalysed carbon-carbon bond formation", *Nature*, 389:54-57 (1997).

Vaught et al., "T7 RNA polymerase transcription with 5-position modified UTP derivatives", *J. Am. Chem. Soc.*, 126:11231-11237 (2004).

Brieba et al., "Roles of Histidine 784 and Tyrosine 639 in Ribose Discrimination by T7 RNA Polymerase", *Biochemistry*, 39:919-923 (2000).

Burmeister, et al., "2-Deoxy Purine, 2'O-Methyl Pyrimidine (dRmY) Aptamers as Candidate Therapeutics", *Oligonucleotides*, 16(4):337-351 (2006).

Henry et al., "The evolution of DNA polymerases with novel activities," Current Opinion in Biotechnology, vol. 16(4): 370-77 (2005).

Ito et al., "In vitro selection of RNA aptamers carrying multiple biotin groups in the side chains," Bioconjugate Chemistry, vol. 12(6): 850-54 (2001).

* cited by examiner atgaacacgattaacatcgctaagaacgacttctctgacatcgaactggctgctatcccgttcaacactctggctgaccattacggtgagcgtttagctcgcgaacagttg
gcccttgagcatgagtcttacgagatgggtgaagcacgcttccgcaagatgtttgagcgtcaacttaaagctggtgaggttgcggataacgctgccgccaagcctctca
tcactaccctactccctaagatgattgcacgcatcaacgactggtttgaggaagtgaaagctaagcgcggcaagcgcccgacagccttccagttcctgcaagaaatca
agccggaagccgtagcgtacatcaccattaagaccactctggcttgcctaaccagtgctgacaatacaaccgttcaggctgtagcaagcgcaatcggtcgggccattg
aggacgaggctcgcttcggtcgtatccgtgaccttgaagctaagcacttcaagaaaaacgttgaggaacaactcaacaagcgcgtagggcacgtctacaagaaagca
tttatgcaagttgtcgaggctgacatgctctctaagggtctactcggtggcgaggcgtggtcttcgtggcataaggaagactctattcatgtaggagtacgctgcatcga
gatgctcattgagtcaaccggaatggttagcttacaccgccaaaatgctggcgtagtaggtcaagactctgagactatcgaactcgcacctgaatacgctgaggctatc
gcaacccgtgcaggtgcgctggctggcatctctccgatgttccaaccttgcgtagttcctcctaagccgtggactggcattactggtggtggctattgggctaacggtcg
tcgtcctctggcgctggtgcgtactcacagtaagaaagcactgatgcgctacgaagacgtttacatgcctgaggtgtacaaagcgattaacattgcgcaaaacaccgca
tggaaaatcaacaagaaagtcctagcggtcgccaacgtaatcaccaagtggaagcattgtccggtcgaggacatccctgcgattgagcgtgaagaactcccgatgaa
accggaagacatcgacatgaatcctgaggctctcaccgcgtggaaacgtgctgccgctgctgtgtaccgcaaggacaaggctcgcaagtctcgccgtatcagccttg
agttcatgcttgagcaagccaataagtttgctaaccataaggccatctggttcccttacaacatggactggcgcggtcgtgtttacgctgtgtcaatgttcaacccgcaag
gtaacgatatgaccaaaggactgcttacgctggcgaaaggtaaaccaatcggtaaggaaggttactactggctgaaaatccacggtgcaaactgtgcgggtgtcgata
aggttccgttccctgagcgcatcaagttcattgaggaaaaccacgagaacatcatggcttgcgctaagtctccactggagaacacttggtgggctgagcaagattctcc
gttctgcttccttgcgttctgctttgagtacgctggggtacagcaccacggcctgagctataactgctcccttccgctggcgtttgacgggtcttgctctggcatccagcac
ttctccgcgatgctccgagatgaggtaggtggtcgcgcggttaacttgcttcctagtgaaaccgttcaggacatctacgggattgttgctaagaaagtcaacgagattcta
caagcagacgcaatcaatgggaccgataacgaagtagttaccgtgaccgatgagaacactggtgaaatctctgagaaagtcaagctgggcactaaggcactggctg
gtcaatggctggcttacggtgttactcgcagtgtgactaagcgttcagtcatgacgctggcttacgggtccaaagagttcggcttccgtcaacaagtgctggaagatacc
attcagccagctattgattccggcaagggtctgatgttcactcagccgaatcaggctgctggatacatggctaagctgatttgggaatctgtgagcgtgacggtggtagc
tgcggttgaagcaatgaactggcttaagtctgctgctaagctgctggctgctgaggtcaaagataagaagactggagagattcttcgcaagcgttgcgctgtgcattgg
gtaactcctgatggtttccctgtgtggcaggaatacaagaagcctattcagacgcgcttgaacctgatgttcctcggtcagttccgcttacagcctaccattaacaccaac
aaagatagcgagattgatgcacacaaacaggagtctggtatcgctcctaactttgtacacagccaagacggtagccaccttcgtaagactgtagtgtgggcacacgag
aagtacggaatcgaatcttttgcactgattcacgactccttcggtaccattccggctgacgctgcgaacctgttcaaagcagtgcgcgaaactatggttgacacatatgag
tcttgtgatgtactggctgatttctacgaccagttcgctgaccagttgcacgagtctcaattggacaaaatgccagcacttccggctaaaggtaacttgaacctccgtgac
atcttagagtcggacttcgcgttcgcgtaa (SEQ ID NO 32)

Fig. 3A

MNTINIAKNDFSDIELAAIPFNTLADHYGERLAREQLALEHESYEMGEARFRKMFERQLKAGEVADNAAAKP
LITTLLPKMIARINDWFEEVKAKRGKRPTAFQFLQEIKPEA VAYITIKTTLACLTSADNTTVQAVASAIGRAIED
EARFGRIRDLEAKHFKKNVEEQLNKRVGHVYKKAFMQVVEADMLSKGLLGGEAWSSWHKEDSIHVGVRCI
EMLIESTGMVSLHRQNAGVVGQDSETIELAPEYAEAIATRAGALAGISPMFQPCVVPPKPWTGITGGGYWAN
GRRPLALVRTHSKKALMRYEDVYMPEVYKAINIAQNTAWKINKKVLAVANVITKWKHCPVEDIPAIEREELP
MKPEDIDMNPEALTAWKRAAAAVYRKDKARKSRRISLEFMLEQANKFANHKAIWFPYNMDWRGRVYAVS
MFNPQGNDMTKGLLTLAKGKPIGKEGYYWLKIHGANCAGVDKVPFPERIKFIEENHENIMACAKSPLENTW
WAEQDSPFCFLAFCFEYAGVQHHGLSYNCSLPLAFDGSCSGIQHFSAMLRDEVGGRAVNLLPSETVQDIYGIV
AKKVNEILQADAINGTDNEVVTVTDENTGEISEKVKLGTKALAGQWLAYGVTRSVTKRSVMTLAYGSKEFG
FRQQVLEDTIQPAIDSGKGLMFTQPNQAAGYMAKLIWESVSVTVVAAVEAMNWLKSAAKLLAAEVKDKKT
GEILRKRCAVHWVTPDGFPVWQEYKKPIQTRLNLMFLGQFRLQPTINTNKDSEIDAHKQESGIAPNFVHSQDG
SHLRKTVVWAHEKYGIESFALIHDSFGTIPADAANLFKAVRETMVDTYESCDVLADFYDQFADQLHESQLDK
MPALPAKGNLNLRDILESDFAFA (SEQ ID NO 33)

Fig. 3B atgaacacgattaacatcgctaagaacgacttctctgacatcgaactggctgctatcccgttcaacactctggctgaccattacggtgagcgtttagctcgcgaacagttg
gcccttgagcatgagtcttacgagatgggtgaagcacgcttccgcaagatgtttgagcgtcaacttaaagctggtgaggttgcggataacgctgccgccaagcctctca
tcactaccctactccctaagatgattgcacgcatcaacgactggtttgaggaagtgaaagctaagcgcggcaagcgcccgacagccttccagttcctgcaagaaatca
agccggaagccgtagcgtacatcaccattaagaccactctggcttgcctaaccagtgctgacaatacaaccgttcaggctgtagcaagcgcaatcggtcgggccattg
aggacgaggctcgcttcggtcgtatccgtgaccttgaagctaagcacttcaagaaaaacgttgaggaacaactcaacaagcgcgtagggcacgtctacaagaaagca
tttatgcaagttgtcgaggctgacatgctctctaagggtctactcggtggcgaggcgtggtcttcgtggcataaggaagactctattcatgtaggagtacgctgcatcga
gatgctcattgagtcaaccggaatggttagcttacaccgccaaaatgctggcgtagtaggtcaagactctgagactatcgaactcgcacctgaatacgctgaggctatc
gcaacccgtgcaggtgcgctggctggcatctctccgatgttccaaccttgcgtagttcctcctaagccgtggactggcattactggtggtggctattgggctaacggtcg
tcgtcctctggcgctggtgcgtactcacagtaagaaagcactgatgcgctacgaagacgtttacatgcctgaggtgtacaaagcgattaacattgcgcaaaacaccgca
tggaaaatcaacaagaaagtcctagcggtcgccaacgtaatcaccaagtggaagcattgtccggtcgaggacatccctgcgattgagcgtgaagaactcccgatgaa
accggaagacatcgacatgaatcctgaggctctcaccgcgtggaaacgtgctgccgctgctgtgtaccgcaaggacaaggctcgcaagtctcgccgtatcagccttg
agttcatgcttgagcaagccaataagtttgctaaccataaggccatctggttcccttacaacatggactggcgcggtcgtgtttacgctgtgtcaatgttcaacccgcaag
gtaacgatatgaccaaaggactgcttacgctggcgaaaggtaaaccaatcggtaaggaaggttactactggctgaaaatccacggtgcaaactgtgcgggtgtcgata
aggttccgttccctgagcgcatcaagttcattgaggaaaaccacgagaacatcatggcttgcgctaagtctccactggagaacacttggtgggctgagcaagattctcc
gttctgcttccttgcgttctgctttgagtacgctggggtacagcaccacggcctgagctataactgctcccttccgctggcgtttgacgggtcttgctctggcatccagcac
ttctccgcgatgctccgagatgaggtaggtggtcgcgcggttaacttgcttcctagtgaaaccgttcaggacatctacgggattgttgctaagaaagtcaacgagattcta
caagcagacgcaatcaatgggaccgataacgaagtagttaccgtgaccgatgagaacactggtgaaatctctgagaaagtcaagctgggcactaaggcactggctg
gtcaatggctggcttacggtgttactcgcagtgtgactaagcgttcagtcatgacgctggctCTGgggtccaaagagttcggcttccgtcaacaagtgctggaagata
ccattcagccagctattgattccggcaagggtctgatgttcactcagccgaatcaggctgctggatacatggctaagctgatttgggaatctgtgagcgtgacggtggta
gctgcggttgaagcaatgaactggcttaagtctgctgctaagctgctggctgctgaggtcaaagataagaagactggagagattcttcgcaagcgttgcgctgtgcatt
gggtaactcctgatggtttccctgtgtggcaggaatacaagaagcctattcagacgcgcttgaacctgatgttcctcggtcagttccgcttacagcctaccattaacacca
acaaagatagcgagattgatgcacacaaacaggagtctggtatcgctcctaactttgtaGCcagccaagacggtagccaccttcgtaagactgtagtgtgggcacac
gagaagtacggaatcgaatcttttgcactgattcacgactccttcggtaccattccggctgacgctgcgaacctgttcaaagcagtgcgcgaaactatggttgacacatat
gagtcttgtgatgtactggctgatttctacgaccagttcgctgaccagttgcacgagtctcaattggacaaaatgccagcacttccggctaaaggtaacttgaacctccgt
gacatcttagagtcggacttcgcgttcgcgtaa (SEQ ID NO 34)

Fig. 4A 1 atgaacacga ttaacatcgc taagaacgac ttctctgaca tcgaactggc tgctatcccg
61 ttcaacactc tggctgacca ttacggtgag cgtttagctc gcgaacagtt ggcccttgag
121 catgagtctt acgagatggg tgaagcacgc ttccgcaaga tgtttgagcg tcaacttaaa
181 gctggtgagg ttgcggataa cgctgccgcc aagcctctca tcactaccct actccctaag
241 atgattgcac gcatcaacga ctggtttgag gaagtgaaag ctaagcgcgg caagcgcccg
301 acagccttcc agttcctgca agaaatcaag ccggaagccg tagcgtacat caccattaag
361 accactctgg cttgcctaac cagtgctgac aatacaaccg ttcaggctgt agcaagcgca
421 atcggtcggg ccattgagga cgaggctcgc ttcggtcgta tccgtgacct tgaagctaag
481 cacttcaaga aaaacgttga ggaacaactc aacaagcgcg tagggcacgt ctacaagaaa
541 gcatttatgc aagttgtcga ggctgacatg ctctctaagg gtctactcgg tggcgaggcg
601 tggtcttcgt ggcataagga agactctatt catgtaggag tacgctgcat cgagatgctc
661 attgagtcaa ccggaatggt tagcttacac cgccaaaatg ctggcgtagt aggtcaagac
721 tctgagacta tcgaactcgc acctgaatac gctgaggcta tcgcaacccg tgcaggtgcg
781 ctggctggca tctctccgat gttccaacct tgcgtagttc ctcctaagcc gtggactggc
841 attactggtg gtggctattg ggctaacggt cgtcgtcctc tggcgctggt gcgtactcac
901 agtaagaaag cactgatgcg ctacgaagac gtttacatgc ctgaggtgta caaagcgatt
961 aacattgcgc aaaacaccgc atggaaaatc aacaagaaag tcctagcggt cgccaacgta
1021 atcaccaagt ggaagcattg tccggtcgag gacatccctg cgattgagcg tgaagaactc
1081 ccgatgaaac cggaagacat cgacatgaat cctgaggctc tcaccgcgtg gaGacgtgct
1141 gccgctgctg tgtaccgcaa ggacaaggct cgcaagtctc gccgtatcag ccttgagttc
1201 atgcttgagc aagccaataa gtttgctaac cataaggcca tctggttccc ttacaacatg
1261 gactggcgcg gtcgtgttta cgctgtgtca atgttcaacc cgcaaggtaa cgatatgacc
1321 aaaggactgc ttacgctggc gaaaggtaaa ccaatcggta aggaaggtta ctactggctg
1381 aaaatccacg gtgcaaactg tgcgggtgtc gataaggttc cgttccctga gcgcatcaag
1441 ttcattgagg aaaaccacga gaacatcatg gcttgcgcta agtctccact ggagaacact
1501 tggtgggctg agcaagattc tccgttctgc ttccttgcgt tctgctttga gtacgctggg
1561 gtacagcacc acggcctgag ctataactgc tcccttccgc tggcgtttga cgggtcttgc
1621 tctggcatcc agcacttctc cgcgatgctc cgagatgagg taggtggtcg cgcggttaac
1681 ttgcttccta gtgaaaccgt tcaggacatc tacgggattg ttgctaagaa agtcaacgag
1741 attctacaag cagacgcaat caatgggacc gataacgaag tagttaccgt gaccgatgag
1801 aacactggtg aaatctctga gaaagtcaag ctgggcacta aggcactggc tggtcaatgg
1861 ctggcttacg gtgttactcg cagtgtgact aagcgttcag tcatgacgct ggctCTGggg
1921 tccaaagagt tcggcttccg tcaacaagtg ctggaagata ccattcagcc agctattgat
1981 tccggcaagg gtctgatgtt cactcagccg aatcaggctg ctggatacat ggctaagctg
2041 atttgggaat ctgtgagcgt gacggtggta gctgcggttg aagcaatgaa ctggcttaag
2101 tctgctgcta agctgctggc tgctgaggtc aaagataaga agactggaga gattcttcgc
2161 aagcgttgcg ctgtgcattg ggtaactcct gatggtttcc ctgtgtggca ggaatacaag
2221 aagcctattc agacgcgctt gaacctgatg ttcctcggtc agttccgctt acagcctacc
2281 attaacacca acaaagatag cgagattgat gcacacaaac aggagtctgg tatcgctcct
2341 aactttgtaG Ccagccaaga cggtagccac cttcgtaaga ctgtagtgtg ggcacacgag
2401 aagtacggaa tcgaatcttt tgcactgatt cacgactcct tcggtaccat tccggctgac
2461 gctgcgaacc tgttcaaagc agtgcgcgaa actatggttg acacatatga gtcttgtgat
2521 gtactggctg atttctacga ccagttcgct gaccagttgc acgagtctca attggacaaa
2581 atgccagcac ttccggctaa aggtaacttg aacctccgtg acatcttaga gtcggacttc
2641 gcgttcgcgt aa (SEQ ID NO 35)

Fig. 4B atgaacacgattaacatcgctaagaacgacttctctgacatcgaactggctgctatcccgttcaacactctggctgaccattacggtgagcgtttagctcgcgaacagttggccc
ttgagcatgagtcttacgagatgggtgaagcacgcttccgcaagatgtttgagcgtcaacttaaagctggtgaggttgcggataacgctgccgccaagcctctcatcactaccc
tactccctaagatgattgcacgcatcaacgactggtttgaggaagtgaaagctaagcgcggcaagcgcccgacagccttccagttcctgcaagaaatcaagccggaagccg
tagcgtacatcaccattaagaccactctggcttgcctaaccagtgctgacaatacaaccgttcaggctgtagcaagcgcaatcggtcgggccattgaggacgaggctcgcttc
ggtcgtatccgtgaccttgaagctaagcacttcaagaaaaacgttgaggaacaactcaacaagcgcgtagggcacgtctacaagaaagcatttatgcaagttgtcgaggctg
acatgctctctaagggtctactcggtggcgaggcgtggtcttcgtggcataaggaagactctattcatgtaggagtacgctgcatcgagatgctcattgagtcaaccggaatgg
ttagcttacaccgccaaaatgctggcgtagtaggtcaagactctgagactatcgaactcgcacctgaatacgctgaggctatcgcaacccgtgcaggtgcgctggctggcatc
tctcTgatgttccaaccttgcgtagttcctcctaagccgtggactggcattactggtggtggctattgggctaacggtcgtcgtcctctggcgctggtgcgtactcacagtaaga
aagcactgatgcgctacgaagacgtttacatgcctgaggtgtacaaagcgattaacattgcgcaaaacaccgcatggaaaatcaacaagaaagtcctagcggtcgccaacgt
aatcaccaagtggaagcattgtccggtcgaggacatccctgcgattgagcgtgaagaactcccgatgaaaccggaagacatcgacatgaatcctgaggctctcaccgcgtg
gaaacgtgctgccgctgctgtgtaccgcaaggacaaggctcgcaagtctcgccgtatcagccttgagttcatgcttgagcaagccaataagtttgctaaccataaggccatct
ggttcccttacaacatggactggcgcggtcgtgtttacgctgtgtcaatgttcaacccgcaaggtaacgatatgaccaaaggactgcttacgctggcgaaaggtaaaccaatc
ggtaaggaaggttactactggctgaaaatccacggtgcaaactgtgcgggtgtcgataaggttccgttccctgagcgcatcaagttcattgaggaaaaccacgagaacatcat
ggcttgcgctaagtctccactggagaacacttggtgggctgagcaagattctccgttctgcttccttgcgttctgctttgagtacgctggggtacagcaccacggcctgagctat
aactgctcccttccgctggcgtttgacgggtcttgctctggcatccagcacttctccgcgatgctccgagatgaggtaggtggtcgcgcggttaacttgcttcctagtgaaaccg
ttcaggacatctacgggattgttgctaagaaagtcaacgagattctacaagcagacgcaatcaatgggaccgataacgaagtagttaccgtgaccgatgagaacactggtga
aatctctgagaaagtcaagctgggcactaaggcactggctggtcaatggctggcttacggtgttactcgcagtgtgactaagcgttcagtcatgacgctggctCTGgggtcc
aaagagttcggcttccgtcaacaagtgctggaagataccattcagccagctattgattccggcaagggtctgatgttcactcagccgaatcaggctgctggatacatggctaag
ctgatttgggaatctgtgagcgtgacggtggtagctgcggttgaagcaatgaactggcttaagtctgctgctaagctgctggctgctgaggtcaaagataagaagactggaga
gattcttcgcaagcgttgcgctgtgcattgggtaactcctgatggtttccctgtgtggcaggaatacaagaagcctattcagacgcgcttgaacctgatgttcctcggtcagttcc
gcttacagcctaccattaacaccaacaaagatagcgagattgatgcacacaaacaggagtctggtatcgctcctaactttgtaGCcagccaagacggtagccaccttcgtaa
gactgtagtgtgggcacacgagaagtacggaatcgaatcttttgcactgattcacgactccttcggtaccattccggctgacgctgcgaacctgttcaaagcagtgcgcgaaa
ctatggttgacacatatgagtcttgtgatgtactggctgatttctacgaccagttcgctgaccagttgcacgagtctcaattggacaaaatgccagcacttccggctaaaggtaac
ttgaacctccgtgacatcttagagtcggacttcgcgttcgcgtaa (SEQ ID NO 36)

Fig. 4C atgaacacgattaacatcgctaagaacgacttctctgacatcgaactggctgctatcccgttcaacactctggctgaccattacggtgagcgtttagctcgcgaacagttg
gcccttgagcatgagtcttacgagatgggtgaagcacgcttccgcaagatgtttgagcgtcaacttaaagctggtgaggttgcggataacgctgccgccaagcctctca
tcactaccctactccctaagatgattgcacgcatcaacgactggtttgaggaagtgaaagctaagcgcggcaagcgcccgacagccttccagttcctgcaagaaatca
agccggaagccgtagcgtacatcaccattaagaccactctggcttgcctaaccagtgctgacaatacaaccgttcaggctgtagcaagcgcaatcggtcgggccattg
aggacgaggctcgcttcggtcgtatccgtgaccttgaagctaagcacttcaagaaaaacgttgaggaacaactcaacaagcgcgtagggcacgtctacaagaaagca
tttatgcaagttgtcgaggctgacatgctctctaagggtctactcggtggcgaggcgtggtcttcgtggcataaggaagactctattcatgtaggagtacgctgcatcga
gatgctcattgagtcaaccggaatggttagcttacaccgccaaaatgctggcgtagtaggtcaagactctgagactatcgaactcgcacctgaatacgctgaggctatc
gcaacccgtgcaggtgcgctggctggcatctctcTgatgttccaaccttgcgtagttcctcctaagccgtggactggcattactggtggtggctattgggctaacggtc
gtcgtcctctggcgctggtgcgtactcacagtaagaaagcactgatgcgctacgaagacgtttacatgcctgaggtgtacaaagcgattaacattgcgcaaaacaccg
catggaaaatcaacaagaaagtcctagcggtcgccaacgtaatcaccaagtggaagcattgtccggtcgaggacatccctgcgattgagcgtgaagaactcccgatg
aaaccggaagacatcgacatgaatcctgaggctctcaccgcgtggaGacgtgctgccgctgctgtgtaccgcaaggacaaggctcgcaagtctcgccgtatcagcc
ttgagttcatgcttgagcaagccaataagtttgctaaccataaggccatctggttcccttacaacatggactggcgcggtcgtgtttacgctgtgtcaatgttcaacccgca
aggtaacgatatgaccaaaggactgcttacgctggcgaaaggtaaaccaatcggtaaggaaggttactactggctgaaaatccacggtgcaaactgtgcgggtgtcg
ataaggttccgttccctgagcgcatcaagttcattgaggaaaaccacgagaacatcatggcttgcgctaagtctccactggagaacacttggtgggctgagcaagattct
ccgttctgcttccttgcgttctgctttgagtacgctggggtacagcaccacggcctgagctataactgctcccttccgctggcgtttgacgggtcttgctctggcatccagc
acttctccgcgatgctccgagatgaggtaggtggtcgcgcggttaacttgcttcctagtgaaaccgttcaggacatctacgggattgttgctaagaaagtcaacgagatt
ctacaagcagacgcaatcaatgggaccgataacgaagtagttaccgtgaccgatgagaacactggtgaaatctctgagaaagtcaagctgggcactaaggcactgg
ctggtcaatggctggcttacggtgttactcgcagtgtgactaagcgttcagtcatgacgctggctCTGgggtccaaagagttcggcttccgtcaacaagtgctggaag
ataccattcagccagctattgattccggcaagggtctgatgttcactcagccgaatcaggctgctggatacatggctaagctgatttgggaatctgtgagcgtgacggtg
gtagctgcggttgaagcaatgaactggcttaagtctgctgctaagctgctggctgctgaggtcaaagataagaagactggagagattcttcgcaagcgttgcgctgtgc
attgggtaactcctgatggtttccctgtgtggcaggaatacaagaagcctattcagacgcgcttgaacctgatgttcctcggtcagttccgcttacagcctaccattaacac
caacaaagatagcgagattgatgcacacaaacaggagtctggtatcgctcctaactttgtaGCcagccaagacggtagccaccttcgtaagactgtagtgtgggcac
acgagaagtacggaatcgaatcttttgcactgattcacgactccttcggtaccattccggctgacgctgcgaacctgttcaaagcagtgcgcgaaactatggttgacaca
tatgagtcttgtgatgtactggctgatttctacgaccagttcgctgaccagttgcacgagtctcaattggacaaaatgccagcacttccggctaaaggtaacttgaacctcc
gtgacatcttagagtcggacttcgcgttcgcgtaa (SEQ ID NO 37)

Fig. 4D

| RELATIVE TRANSCRIPT YIELDS* | ARC2118 | ARC2119 |
|---|---|---|
| [rGTP] 0uM | 40 | 49 |
| [rGTP] 5uM | 74 | 62 |
| [rGTP] 10uM | 94 | 21 |
| [rGTP] 20uM | 100 | 30 |
| [rGTP] 40uM | 95 | 36 |
| [rGTP] 80uM | 93 | 41 |
| [rGTP] 160uM | 95 | 32 |

Fig. 5

| TRANSCRIPTION COMPONENT CONCENTRATION | TRANSCRIPTION CONDITIONS 1 | TRANSCRIPTION CONDITIONS 2 | TRANSCRIPTION CONDITIONS 3 | TRANSCRIPTION CONDITIONS 4 |
|---|---|---|---|---|
| [MgCl2] | 5mM | 6.5mM | 8mM | 9.5mM |
| [MnCl2] | 1.5mM | 2mM | 2.5mM | 3mM |
| [2'-OMe NTP] (each) | 0.5mM | 1mM | 1.5mM | 2mM |
| RELATIVE YIELD | 0.8 | 1.0 | 1.5 | 1.6 |

Fig. 6

| | DELETIONS | INSERTIONS | SUBSTITUTIONS | PERFECT N30 | N |
|---|---|---|---|---|---|
| 2'-OH RNA[1] | 0.7% | 0.0% | 0.3% | 74% | 1936 |
| 2'-OMe RNA[1] | 0.6% | 0.6% | 1.2% | 49% | 1584 |
| 2'-OMe RNA[2] | 0.0% | 0.0% | 0.23% | 93% | 1300 |

Fig. 7

| | TOTAL | A | G | C | T | N |
|---|---|---|---|---|---|---|
| STARTING LIBRARY | 1206 | 21.9% | 28.3% | 24.1% | 25.0% | 0.66% |
| LIBRARY AFTER TRANSCRIPTION | 1386 | 25% | 25.3% | 21.5% | 28.1% | 0.0% |

Fig. 8

SEQUENCE LISTING

```
<160> NUMBER OF SEQ ID NOS: 37

<210> SEQ ID NO 1
<211> LENGTH: 883
<212> TYPE: PRT
<213> ORGANISM: artificial sequence
<220> FEATURE:
<223> OTHER INFORMATION: chemically synthesized modified T7 polymerase
      Y639/H784A

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60
```

```
Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

```
Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val Ala
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 2
<211> LENGTH: 883
<212> TYPE: PRT
<213> ORGANISM: artificial sequence
<220> FEATURE:
<223> OTHER INFORMATION: chemically synthesized modified T7 polymerase Y639L/H784A/K378R

<400> SEQUENCE: 2

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Arg Arg Ala Ala Ala Ala Val
    370                 375                 380

Tyr Arg Lys Asp Lys Ala Arg Lys Ser Arg Arg Ile Ser Leu Glu Phe
385                 390                 395                 400
```

-continued

```
Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val Ala
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
```

```
          820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 3
<211> LENGTH: 883
<212> TYPE: PRT
<213> ORGANISM: artificial sequence
<220> FEATURE:
<223> OTHER INFORMATION: chemically synthesized modified T7 polymerase
      Y639L

<400> SEQUENCE: 3

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300
```

```
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
```

```
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 4
<211> LENGTH: 883
<212> TYPE: PRT
<213> ORGANISM: artificial sequence
<220> FEATURE:
<223> OTHER INFORMATION: chemically synthesized modified T7 polymerase
      Y639L/K378R

<400> SEQUENCE: 4

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205
```

-continued

```
Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Arg Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Leu Gly
```

-continued

```
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 5
<211> LENGTH: 883
<212> TYPE: PRT
<213> ORGANISM: artificial sequence
<220> FEATURE:
<223> OTHER INFORMATION: chemically synthesized modified T7 polymerase
      P266L/Y639L/H784A

<400> SEQUENCE: 5

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110
```

```
Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Leu Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
```

530 535 540

His Phe Ser Ala Met Leu Arg Asp Glu Val Gly Gly Arg Ala Val Asn
545 550 555 560

Leu Leu Pro Ser Glu Thr Val Gln Asp Ile Tyr Gly Ile Val Ala Lys
565 570 575

Lys Val Asn Glu Ile Leu Gln Ala Asp Ala Ile Asn Gly Thr Asp Asn
580 585 590

Glu Val Val Thr Val Thr Asp Glu Asn Thr Gly Glu Ile Ser Glu Lys
595 600 605

Val Lys Leu Gly Thr Lys Ala Leu Ala Gly Gln Trp Leu Ala Tyr Gly
610 615 620

Val Thr Arg Ser Val Thr Lys Arg Ser Val Met Thr Leu Ala Leu Gly
625 630 635 640

Ser Lys Glu Phe Gly Phe Arg Gln Gln Val Leu Glu Asp Thr Ile Gln
645 650 655

Pro Ala Ile Asp Ser Gly Lys Gly Leu Met Phe Thr Gln Pro Asn Gln
660 665 670

Ala Ala Gly Tyr Met Ala Lys Leu Ile Trp Glu Ser Val Ser Val Thr
675 680 685

Val Val Ala Ala Val Glu Ala Met Asn Trp Leu Lys Ser Ala Ala Lys
690 695 700

Leu Leu Ala Ala Glu Val Lys Asp Lys Lys Thr Gly Glu Ile Leu Arg
705 710 715 720

Lys Arg Cys Ala Val His Trp Val Thr Pro Asp Gly Phe Pro Val Trp
725 730 735

Gln Glu Tyr Lys Lys Pro Ile Gln Thr Arg Leu Asn Leu Met Phe Leu
740 745 750

Gly Gln Phe Arg Leu Gln Pro Thr Ile Asn Thr Asn Lys Asp Ser Glu
755 760 765

Ile Asp Ala His Lys Gln Glu Ser Gly Ile Ala Pro Asn Phe Val Ala
770 775 780

Ser Gln Asp Gly Ser His Leu Arg Lys Thr Val Val Trp Ala His Glu
785 790 795 800

Lys Tyr Gly Ile Glu Ser Phe Ala Leu Ile His Asp Ser Phe Gly Thr
805 810 815

Ile Pro Ala Asp Ala Ala Asn Leu Phe Lys Ala Val Arg Glu Thr Met
820 825 830

Val Asp Thr Tyr Glu Ser Cys Asp Val Leu Ala Asp Phe Tyr Asp Gln
835 840 845

Phe Ala Asp Gln Leu His Glu Ser Gln Leu Asp Lys Met Pro Ala Leu
850 855 860

Pro Ala Lys Gly Asn Leu Asn Leu Arg Asp Ile Leu Glu Ser Asp Phe
865 870 875 880

Ala Phe Ala

<210> SEQ ID NO 6
<211> LENGTH: 883
<212> TYPE: PRT
<213> ORGANISM: artificial sequence
<220> FEATURE:
<223> OTHER INFORMATION: chemically synthesized modified T7 polymerase
P266L/Y639L/H784A/K378R

<400> SEQUENCE: 6

Met Asn Thr Ile Asn Ile Ala Lys Asn Asp Phe Ser Asp Ile Glu Leu
1 5 10 15

```
Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Leu Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Arg Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
```

```
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val Ala
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860
```

Pro Ala Lys Gly Asn Leu Asn Leu Arg Asp Ile Leu Glu Ser Asp Phe
865 870 875 880

Ala Phe Ala

<210> SEQ ID NO 7
<211> LENGTH: 93
<212> TYPE: DNA
<213> ORGANISM: artificial sequence
<220> FEATURE:
<223> OTHER INFORMATION: chemically synthesized DNA transcription template ARC 2118
<220> FEATURE:
<221> NAME/KEY: misc_feature
<222> LOCATION: (40)..(69)
<223> OTHER INFORMATION: n is a, t, c, or g

<400> SEQUENCE: 7
taatacgact cactataggg gagtacaata acgttctcgn nnnnnnnnnn nnnnnnnnnn 60
nnnnnnnnng gatcgttacg actagcatcg atg 93

<210> SEQ ID NO 8
<211> LENGTH: 10
<212> TYPE: DNA
<213> ORGANISM: artificial sequence
<220> FEATURE:
<223> OTHER INFORMATION: chemically synthesized immunostimulatory motif

<400> SEQUENCE: 8
aacgttcgag 10

<210> SEQ ID NO 9
<211> LENGTH: 35
<212> TYPE: DNA
<213> ORGANISM: artificial sequence
<220> FEATURE:
<223> OTHER INFORMATION: chemically synthesized sequence

<400> SEQUENCE: 9
agtcatgacg ctggctctgg ggtccaaaga gttcg 35

<210> SEQ ID NO 10
<211> LENGTH: 34
<212> TYPE: DNA
<213> ORGANISM: artificial sequence
<220> FEATURE:
<223> OTHER INFORMATION: chemically synthesized sequence

<400> SEQUENCE: 10
gaactctttg gaccccagag ccagcgtcat gact 34

<210> SEQ ID NO 11
<211> LENGTH: 31
<212> TYPE: DNA
<213> ORGANISM: artificial sequence
<220> FEATURE:
<223> OTHER INFORMATION: chemically synthesized sequence

<400> SEQUENCE: 11
ggctggcatc tctctgatgt tccaaccttg c 31

<210> SEQ ID NO 12
<211> LENGTH: 31
<212> TYPE: DNA
<213> ORGANISM: artificial sequence
<220> FEATURE:
<223> OTHER INFORMATION: chemically synthesized sequence

<400> SEQUENCE: 12
gcaaggttgg aacatcagag agatgccagc c 31

<210> SEQ ID NO 13
<211> LENGTH: 34
<212> TYPE: DNA
<213> ORGANISM: artificial sequence
<220> FEATURE:
<223> OTHER INFORMATION: chemically synthesized sequence

<400> SEQUENCE: 13
cgctcctaac tttgtagcca gccaagacgg tagc 34

<210> SEQ ID NO 14
<211> LENGTH: 34
<212> TYPE: DNA
<213> ORGANISM: artificial sequence
<220> FEATURE:
<223> OTHER INFORMATION: chemically synthesized sequence

<400> SEQUENCE: 14
gctaccgtct tggctggcta caaagttagg agcg 34

<210> SEQ ID NO 15
<211> LENGTH: 33
<212> TYPE: DNA
<213> ORGANISM: artificial sequence
<220> FEATURE:
<223> OTHER INFORMATION: chemically synthesized sequence

<400> SEQUENCE: 15
gctctcaccg cgtggagacg tgctgccgct gct 33

<210> SEQ ID NO 16
<211> LENGTH: 33
<212> TYPE: DNA
<213> ORGANISM: artificial sequence
<220> FEATURE:
<223> OTHER INFORMATION: chemically synthesized sequence

<400> SEQUENCE: 16
agcagcggca gcacgtctcc acgcggtgag agc 33

<210> SEQ ID NO 17
<211> LENGTH: 66
<212> TYPE: DNA
<213> ORGANISM: artificial sequence
<220> FEATURE:
<223> OTHER INFORMATION: chemically synthesized 5'-primer

<400> SEQUENCE: 17
aaaaaaaaaa aaaaaaaaaa aaaaaaataa tacgactcac tataggggag tacaataacg 60
ttctcg 66

<210> SEQ ID NO 18
<211> LENGTH: 20
<212> TYPE: DNA
<213> ORGANISM: artificial sequence
<220> FEATURE:
<223> OTHER INFORMATION: chemically synthesized 3'-primer

<400> SEQUENCE: 18
catcgatgct agtcgtaacg 20

<210> SEQ ID NO 19

<211> LENGTH: 89
<212> TYPE: DNA
<213> ORGANISM: artificial sequence
<220> FEATURE:
<223> OTHER INFORMATION: chemically synthesized DNA transcription
template
<220> FEATURE:
<221> NAME/KEY: misc_feature
<222> LOCATION: (24)..(63)
<223> OTHER INFORMATION: n is a, t, c or g

<400> SEQUENCE: 19
gggagaattc cgaccagaag cttnnnnnnn nnnnnnnnnn nnnnnnnnnn nnnnnnnnnn 60
nnncatatgt gcgtctacat ggatcctca 89

<210> SEQ ID NO 20
<211> LENGTH: 94
<212> TYPE: DNA
<213> ORGANISM: artificial sequence
<220> FEATURE:
<223> OTHER INFORMATION: chemically synthesized DNA transcription
template
<220> FEATURE:
<221> NAME/KEY: misc_feature
<222> LOCATION: (21)..(60)
<223> OTHER INFORMATION: n is a, t, c or g

<400> SEQUENCE: 20
gggagagaca agcttgggtc nnnnnnnnnn nnnnnnnnnn nnnnnnnnnn nnnnnnnnnn 60
agaagagaaa gagaagttaa ttaaggatcc tcag 94

<210> SEQ ID NO 21
<211> LENGTH: 40
<212> TYPE: DNA
<213> ORGANISM: artificial sequence
<220> FEATURE:
<223> OTHER INFORMATION: chemically synthesized 5' primer sequence

<400> SEQUENCE: 21
taatacgact cactataggg agaattccga ccagaagctt 40

<210> SEQ ID NO 22
<211> LENGTH: 26
<212> TYPE: DNA
<213> ORGANISM: artificial sequence
<220> FEATURE:
<223> OTHER INFORMATION: chemically synthesized 3' primer sequence

<400> SEQUENCE: 22
tgaggatcca tgtagacgca catatg 26

<210> SEQ ID NO 23
<211> LENGTH: 37
<212> TYPE: DNA
<213> ORGANISM: artificial sequence
<220> FEATURE:
<223> OTHER INFORMATION: chemically synthesized 5' primer sequence

<400> SEQUENCE: 23
taatacgact cactataggg agagacaagc ttgggtc 37

<210> SEQ ID NO 24
<211> LENGTH: 34
<212> TYPE: DNA
<213> ORGANISM: artificial sequence
<220> FEATURE:
<223> OTHER INFORMATION: chemically synthesized 3' primer sequence

<400> SEQUENCE: 24
ctgaggatcc ttaattaact tctctttctc ttct 34

<210> SEQ ID NO 25

<400> SEQUENCE: 25

000

<210> SEQ ID NO 26
<211> LENGTH: 59
<212> TYPE: DNA
<213> ORGANISM: artificial sequence
<220> FEATURE:
<223> OTHER INFORMATION: chemically synthesized sequence

<400> SEQUENCE: 26
gatcgatcga tcgatcgatc taatacgact cactataggg gagtacaata acgttctcg 59

<210> SEQ ID NO 27
<211> LENGTH: 24
<212> TYPE: DNA
<213> ORGANISM: artificial sequence
<220> FEATURE:
<223> OTHER INFORMATION: chemically synthesized sequence

<400> SEQUENCE: 27
catcgatgct agtcgtaacg atcc 24

<210> SEQ ID NO 28
<211> LENGTH: 86
<212> TYPE: DNA
<213> ORGANISM: artificial sequence
<220> FEATURE:
<223> OTHER INFORMATION: chemically synthesized DNA transcription template
<220> FEATURE:
<221> NAME/KEY: misc_feature
<222> LOCATION: (21)..(60)
<223> OTHER INFORMATION: n is a, t, c, or g

<400> SEQUENCE: 28
gggagaattc cgaccacaag nnnnnnnnnn nnnnnnnnnn nnnnnnnnnn nnnnnnnnnn 60
catatgtgcg tctacatgga tcctca 86

<210> SEQ ID NO 29
<211> LENGTH: 37
<212> TYPE: DNA
<213> ORGANISM: artificial sequence
<220> FEATURE:
<223> OTHER INFORMATION: chemically synthesized 5' primer sequence

<400> SEQUENCE: 29
taatacgact cactataggg agaattccga ccacaag 37

<210> SEQ ID NO 30
<211> LENGTH: 26
<212> TYPE: DNA
<213> ORGANISM: artificial sequence
<220> FEATURE:
<223> OTHER INFORMATION: chemically synthesized 3' primer sequence

<400> SEQUENCE: 30
tgaggatcca tgtagacgca catatg 26

<210> SEQ ID NO 31

<211> LENGTH: 93
<212> TYPE: DNA
<213> ORGANISM: artificial sequence
<220> FEATURE:
<223> OTHER INFORMATION: chemically synthesized DNA transcription
      template ARC 2119
<220> FEATURE:
<221> NAME/KEY: misc_feature
<222> LOCATION: (40)..(69)
<223> OTHER INFORMATION: n is a, t, c, or g

<400> SEQUENCE: 31
taatacgact cactataggg ggtgatattg acgttctcgn nnnnnnnnnn nnnnnnnnnn 60
nnnnnnnnng gatcgttacg actagcatcg atg 93

<210> SEQ ID NO 32
<211> LENGTH: 2652
<212> TYPE: DNA
<213> ORGANISM: artificial sequence
<220> FEATURE:
<223> OTHER INFORMATION: chemically synthesized wild type T7 RNA
      polymerase

<400> SEQUENCE: 32
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560

```
gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 33
<211> LENGTH: 883
<212> TYPE: PRT
<213> ORGANISM: artificial sequence
<220> FEATURE:
<223> OTHER INFORMATION: chemically synthesized wild type T7 RNA polymerase

<400> SEQUENCE: 33

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
```

-continued

```
                165                 170                 175
Val Tyr Lys Lys Ala Phe Met Gln Val Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Gly Tyr Trp Ala
        275                 280                 285
Asn Gly Arg Arg Pro Leu Ala Leu Val Arg Thr His Ser Lys Lys Ala
    290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
        355                 360                 365
Met Asn Pro Glu Ala Leu Thr Ala Trp Lys Arg Ala Ala Ala Ala Val
    370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
```

```
Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 34
<211> LENGTH: 2652
<212> TYPE: DNA
<213> ORGANISM: artificial sequence
<220> FEATURE:
<223> OTHER INFORMATION: chemically synthesized mutant T7 RNA polymerase
      Y639L/H784A

<400> SEQUENCE: 34

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac gcatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420
```

-continued

```
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggctctgggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtag ccagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

<210> SEQ ID NO 35
<211> LENGTH: 2652

<212> TYPE: DNA
<213> ORGANISM: artificial sequence
<220> FEATURE:
<223> OTHER INFORMATION: chemically synthesized mutant T7 RNA polymerase
Y639L/H784A/K378R
sequence

<400> SEQUENCE: 35

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gagacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggctctgggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
```

aagcgttgcg ctgtgcattg ggtaactcct gatggtttcc ctgtgtggca ggaatacaag 2220
aagcctattc agacgcgctt gaacctgatg ttcctcggtc agttccgctt acagcctacc 2280
attaacacca acaaagatag cgagattgat gcacacaaac aggagtctgg tatcgctcct 2340
aactttgtag ccagccaaga cggtagccac cttcgtaaga ctgtagtgtg ggcacacgag 2400
aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 36
<211> LENGTH: 2652
<212> TYPE: DNA
<213> ORGANISM: artificial sequence
<220> FEATURE:
<223> OTHER INFORMATION: chemically synthesized mutant T7 RNA polymerase P266L/Y639L/H784A sequence

<400> SEQUENCE: 36
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctctgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500

```
tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggctctgggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtag ccagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 37
<211> LENGTH: 2652
<212> TYPE: DNA
<213> ORGANISM: artificial sequence
<220> FEATURE:
<223> OTHER INFORMATION: chemically synthesized mutant T7 RNA polymerase P266L/Y639L/H784A/K378R sequence

<400> SEQUENCE: 37

```
atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac gcatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctctgat gttccaacct tgcgtagttc ctcctaagcc gtggactggc    840

attactggtg gtggctattg ggctaacggt cgtcgtcctc tggcgctggt gcgtactcac    900
```

-continued

```
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gagacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggctctgggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtag ccagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

MATERIALS AND METHODS FOR THE GENERATION OF TRANSCRIPTS COMPRISING MODIFIED NUCLEOTIDES

REFERENCE TO RELATED APPLICATIONS

This non-provisional patent application is a continuation-in-part of U.S. patent application Ser. No. 11/480,188, filed Jun. 30, 2006, which claims the benefit under 35 U.S.C. §119(e) to U.S. Provisional application 60/696,292, filed Jun. 30, 2005, and this non-provisional patent application claims the benefit under 35 U.S.C. §119(e) to the following provisional applications: U.S. Provisional Patent Application Ser. No. 60/876,780, filed Dec. 22, 2006 and U.S. Provisional Patent Application Ser. No. 60/879,830, filed Jan. 10, 2007, each of which is herein incorporated by reference in its entirety.

FIELD OF INVENTION

The invention relates to materials and methods for transcribing nucleic acids, particularly modified enzymes and materials and methods for using the modified enzymes in template directed polymerization to increase the incorporation of modified nucleotides into nucleic acids, particularly aptamers.

BACKGROUND OF THE INVENTION

An aptamer by definition is an isolated nucleic acid molecule which binds with high specificity and affinity to some target such as a protein through interactions other than Watson-Crick base pairing. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the high specificity binding of a target molecule, is not dependent on a conserved linear base sequence, but rather a particular secondary/tertiary structure. That is, aptamers are non-coding sequences. Any coding potential that an aptamer may possess is entirely fortuitous and plays no role whatsoever in the binding of an aptamer to its cognate target. Thus, while it may be that aptamers that bind to the same target, and even to the same site on that target, share a similar linear base sequence, most do not.

Aptamers must also be differentiated from the naturally occurring nucleic acid sequences that bind to certain proteins. These latter sequences are naturally occurring sequences embedded within the genome of the organism that bind to a specialized sub-group of proteins that are involved in the transcription, translation and transportation of naturally occurring nucleic acids, i.e., nucleic acid binding proteins. Aptamers on the other hand are short, isolated, non-naturally occurring nucleic acid molecules. While aptamers can be identified that bind nucleic acid binding proteins, in most cases such aptamers have little or no sequence identity to the sequences recognized by the nucleic acid binding proteins in nature. More importantly, aptamers can bind virtually any protein (not just nucleic acid binding proteins) as well as almost any target of interest including small molecules, carbohydrates, peptides, etc. For most targets, even proteins, a naturally occurring nucleic acid sequence to which it binds does not exist. For those targets that do have such a sequence, i.e., nucleic acid binding proteins, such sequences will differ from aptamers as a result of the relatively low binding affinity used in nature as compared to tightly binding aptamers.

Aptamers, like peptides generated by phage display or antibodies, are capable of binding to selected targets with high specificity and modulating the target's activity or binding interactions, e.g., through binding aptamers may block their target's ability to function. As with antibodies, this functional property of high specificity binding to a target is an inherent property. Also as with antibodies, although the skilled person may not know what precise structural characteristics an aptamer to a target will have, the skilled person knows how to identify, make and use such a molecule in the absence of a precise structural definition.

Aptamers also are analogous to small molecule therapeutics in that a single structural change, however seemingly minor, can dramatically effect (by several orders of magnitude) the binding and/or other activity (or activities) of the aptamer. On the other hand, some structural changes will have little or no effect whatsoever. This results from the importance of the secondary/tertiary structure of aptamers. In other words, an aptamer is a three dimensional structure held in a fixed conformation that provides chemical contacts to bind its given target with high specificity. Consequently: (1) some areas or particular sequences are essential as (a) specific points of contact with target, and/or as (b) sequences that position the molecules in contact with the target; (2) some areas or particular sequences have a range of variability, e.g., nucleotide X must be a pyrimidine, or nucleotide Y must be a purine, or nucleotides X and Y must be complementary; and (3) some areas or particular sequences can be anything, i.e., they are essentially spacing elements, e.g., they could be any string of nucleotides of a given length or even an non-nucleotide spacer such as a PEG molecule.

Discovered by an in vitro selection process from pools of random sequence oligonucleotides, aptamers have been generated for over 130 proteins including growth factors, transcription factors, enzymes, immunoglobulins, and receptors. A typical aptamer is 10-15 kDa in size (20-45 nucleotides), binds its target with nanomolar to sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

Aptamers have a number of desirable characteristics for use as therapeutics and in affinity purification, detection and diagnostics including, depending on the intended use, high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated therapeutically acceptable toxicity or lack of immunogenicity. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers, allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders. In contrast, antibodies must be stored refrigerated.

In addition to the intrinsic stability of aptamers, incorporation of modified nucleotides (e.g., 2'-modified nucleotides) into aptamers, can increase resistance to enzymatic, chemical, thermal, and physical degradation. While incorporation of modified nucleotides during SELEX™ process is oftentimes preferable to incorporation of modified nucleotides after identification of aptamers, it has been historically difficult because of low transcription yields. Furthermore, it would be beneficial to increase the chemical and structural diversity of the pools or libraries from which aptamers are selected. The present invention provides improved materials and methods to meet this and other needs.

SUMMARY OF THE INVENTION

The present relates to T7 RNA polymerases, which may be purified, isolated and/or recombinant. As used herein the term isolated encompasses polymerases of the invention when recombinantly expressed in a cell or tissue. As used herein the term isolated encompasses nucleic acid sequences of the invention when engineered into a cell or tissue In one embodiment, a T7 RNA polymerase comprising an altered amino acid, at position 639 and position 784 wherein the altered amino acid at position 639 is not a phenylalanine when the altered amino acid at position 784 is an alanine is provided. In another embodiment, the above described T7 RNA polymerase further comprising an altered amino acid at position 378 is provided. In another embodiment, the above described T7 RNA polymerases further comprising an altered amino acid at position 266 is provided. In a particular embodiment the altered amino acid at position 639 is a leucine and the altered amino acid at position 784 is an alanine. In a further embodiment, the altered amino acid at position 266 is a leucine. In a further embodiment, the altered amino acid at position 378 is an arginine. The term "altered amino acids" as used herein are altered relative to the corresponding wild type amino acid at the indicated position.

In preferred embodiments, the altered amino acids increase the transcriptional yield of nucleic acids comprising 2'-OMe modifications by the polymerase in a transcription reaction comprising nucleotide triphosphates wherein the guanidine triphosphate is 2'-OMe guanidine triphosphate, preferably wherein all the nucleotides triphosphates are 2'-OMe nucleotide triphosphates. In a particular embodiment the increase in transcription yield is relative to a T7 RNA polymerase lacking the altered amino acids when transcription is carried out for both the altered amino acid T7 RNA polymerase and the T7 RNA polymerase lacking the altered amino acids under identical transcription conditions. In another embodiment, the altered amino acids decrease discrimination against 2'-OMe nucleotide triphosphates, particularly 2'-OMe guanidine triphosphate. In a particular embodiment, the decreased discrimination against 2'-OMe nucleotide triphosphates is relative to a T7 RNA polymerase lacking the altered amino acids when both polymerases are used under identical transcription conditions, particularly relative to wild type T7 RNA polymerase. In particular embodiments of this aspect, the T7 RNA polymerase lacking the altered amino acids is the wild type T7 RNA polymerase except that it comprises an amino acid at position 639 altered to a phenylalanine and an amino acid at position 784 altered to alanine or a mutant polymerase having the wild type amino acid sequence except that a phenylalanine has been substituted for the tyrosine at position 639, and an alanine has been substituted for the histidine at position 784 and an arginine residue substituted for the lysine residue at position 378 (Y639F/H784A/K378R).

In a particular embodiment, an isolated polypeptide comprising an amino acid selected from the group consisting of: SEQ ID NO 1, SEQ ID NO 2, SEQ ID NO 5 and SEQ ID NO 6. In a particular embodiment, a kit comprising a container containing a T7 RNA polymerase of the invention is provided.

In some embodiments, a method of transcribing a single stranded nucleic acid comprising incubating a mutant T7 RNA polymerase of the invention with a template nucleic acid under reaction conditions sufficient to result in transcription is provided. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In another embodiment, an isolated nucleic acid encoding a polypeptide of the invention is provided. In a particular embodiment a nucleic acid encoding a polypeptide comprising an amino acid selected from the group consisting of: SEQ ID NO 1, SEQ ID NO 2, SEQ ID NO 5 and SEQ ID NO 6 is provided. In a particular embodiment a nucleic acid sequence, selected from the group consisting of: SEQ ID NO 34, SEQ ID NO 35, SEQ ID NO 36 and SEQ ID NO 37 is provided. In some embodiments, a vector comprising an isolated nucleic acid sequence of the invention is provided. In a particular embodiment, an expression vector comprising a nucleic acid of the invention operably linked to a promoter is provided. In another embodiment of the invention, a cell comprising the expression vector of the invention is provided.

In a particular embodiment, a cell wherein the mutant T7 RNA polymerase of the invention is expressed by the cell is provided. In some embodiments, a kit comprising a container containing a nucleic acid encoding a T7 RNA polymerase of the invention is provided. In some embodiments, a method of manufacturing a mutant T7 polymerase of the invention, e.g., a polymerase comprising an amino acid selected from the group consisting of: SEQ ID NO 1, SEQ ID NO 2, SEQ ID NO 5 and SEQ ID NO 6, is provided. In some embodiments, the method of manufacture comprises expressing the expression vector encoding the mutant T7 polymerase of the invention in a cell. In some embodiments the method of manufacture further comprises purifying the expression the mutant T7 polymerase of the invention.

In another embodiment, a method of transcribing a fully 2'-OMe nucleic acid comprising the steps of a) incubating a template nucleic acid in a reaction mixture under conditions comprising a mutant RNA polymerase, a nucleic acid transcription template and nucleoside triphosphates, wherein the nucleoside triphosphates are 2'-OMe, and b) transcribing the transcription reaction mixture to result in single stranded nucleic acid, wherein all of the nucleotides of the single stranded nucleic acids are 2'-OMe modified except that the first nucleotide of the transcripts (i.e., the 5' terminal nucleotide) can be 2' unmodified, is provided. In some embodiments, the first nucleoside of the transcript may be 2'-OH guanidine. In some embodiments of the method, the mutant RNA polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine of the polymerase for use in the methods of the invention. In a further embodiment, the altered amino acid at position 378 is an arginine in the polymerase for use in the methods of the invention. In a particular embodiment, an isolated polypeptide comprising an amino acid selected from the group consisting of: SEQ ID NO 1, SEQ ID NO 2, SEQ ID NO 5 and SEQ ID NO 6 is provided. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In some embodiments of the method of the invention, the transcription reaction further comprises magnesium ions. In another embodiment, the transcription reaction further comprises manganese ions. In some embodiments, the transcription reaction further comprises both magnesium and manganese ions. In another embodiment, the magnesium ions are present in the transcription reaction at a concentration that is between 3.0 to 3.5 times greater than the manganese ions. In another embodiment, wherein each nucleotide triphosphate is present in the transcription reaction at a concentration of 1.0 mM, the concentration of magnesium ions is 6.5 mM, and the concentration of manganese ions is 2.0 mM. In another embodiment, wherein each nucleotide triphosphate is present in the transcription reaction at a concentration of 1.5 mM, the concentration of magnesium ions 8 mM, and the concentration of manganese ions is 2.5 mM. In another embodiment, wherein each nucleotide triphosphate is present in the transcription reaction at a concentration of 2.0 mM, the concentration of magnesium ions 9.5 mM and concentration of manganese ions is 3.0 mM.

In another embodiment, the transcription reaction further comprises a non 2'-OMe guanosine non-triphosphate residue, particularly wherein the non 2'-OMe guanosine non-triphosphate residue selected from the group consisting of: guanosine monophosphate, guanosine diphosphate, 2' fluoro guanosine monophosphate, 2' fluoro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase.

In another aspect of the invention a method for identifying aptamers is provided. In one embodiment, a method for identifying an aptamer, comprising: a) preparing a transcription reaction mixture comprising a mutant polymerase of the invention, and one or more nucleic acid transcription templates) transcribing the transcription reaction mixture to result in a candidate mixture of single stranded nucleic acids, wherein all but optionally one of the nucleotides of the single stranded nucleic acids are 2'-modified, c) contacting the candidate mixture with the target molecule, d) partitioning the nucleic acids having an increased affinity for the target molecule, relative to an affinity of the candidate mixture, from the candidate mixture, and e) amplifying the increased affinity nucleic acids to yield an aptamer enriched mixture, whereby aptamers to the target molecule comprise all 2'-modified nucleotide except that the first nucleotide of the aptamers can be 2'-unmodified are identified, is provided. In some embodiments, the amplifying step f) comprises (i) optionally dissociating the increased affinity nucleic acids from the target, ii) reverse transcribing the increased affinity nucleic acids dissociated from the nucleic acid-target complexes, iii) amplifying the reverse transcribed increased affinity nucleic acids; and (ii) preparing a transcription reaction mixture comprising the amplified reverse transcribed increased affinity nucleic acids as the transcription template and transcribing the transcription mixture.

In some embodiments of the aptamer identification methods of the invention, the mutant RNA polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine of the polymerase for use in the methods of the invention. In a further embodiment, the altered amino acid at position 378 is an arginine in the polymerase for use in the methods of the invention. In a particular embodiment, an isolated polypeptide comprising an amino acid selected from the group consisting of: SEQ ID NO 1, SEQ ID NO 2, SEQ ID NO 5 and SEQ ID NO 6 is used in the aptamer identification method of the invention. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In some embodiments, all the nucleotide triphosphates in the transcription reaction are 2'-OMe modified. In one embodiment, the one or more nucleic acid transcription template comprises a T7 RNA polymerase promoter and a leader sequence immediately 3' to the T7 RNA polymerase promoter. In some embodiments of this aspect, the method comprises repeating steps a) to e) iteratively.

In some embodiments, the transcription reaction further comprises magnesium ions. In another embodiment, the transcription reaction further comprises manganese ions. In another embodiment, the magnesium ions are present in the transcription reaction at a concentration that is between 3.0 to 3.5 times greater than the manganese ions. In another embodiment, wherein each nucleotide triphosphate is present in the transcription reaction at a concentration of 1.0 mM, the concentration of magnesium ions is 6.5 mM, and the concentration of manganese ions is 2.0 mM. In another embodiment, wherein each nucleotide triphosphate is present in the transcription reaction at a concentration of 1.5 mM, the concentration of magnesium ions 8 mM, and the concentration of manganese ions is 2.5 mM. In another embodiment, wherein each nucleotide triphosphate is present in the transcription reaction at a concentration of 2.0 mM, the concentration of magnesium ions 9.5 mM and concentration of manganese ions is 3.0 mM.

In another embodiment of this aspect, the transcription reaction for use in the aptamer identification method of the invention further comprises a non 2'-OMe guanosine non-triphosphate residue, particularly wherein the non 2'-OMe guanosine non-triphosphate residue selected from the group consisting of: guanosine monophosphate, guanosine diphosphate, fluoro guanosine monophosphate, 2' fluoro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase. In some embodiments, the transcription reaction further comprises both magnesium and manganese ions.

In another embodiment, a method of transcribing a nucleic acid comprising the steps of: a) incubating a template nucleic acid in a reaction mixture comprising a mutant polymerase, a nucleic acid transcription template and nucleoside triphosphates, wherein the guanidine triphosphates are 2'-OMe, and b) transcribing the transcription reaction mixture under conditions that result in single stranded nucleic acid, wherein all of the guanidine nucleotides of the resulting single stranded nucleic acid, except for the first nucleotide of the transcript, are 2'-OMe modified is provided.

In some embodiments of the method, the mutant RNA polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine. In a further embodiment, the altered amino acid at position 378 is an arginine in the polymerase for use in the methods of the invention. In a particular embodiment, the transcription methods of the invention use an isolated polypeptide comprising an amino acid selected from the group consisting of: SEQ ID NO 1, SEQ ID NO 2, SEQ ID NO 5 and SEQ ID NO 6. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In some embodiments of the transcription methods in which all the guanidine triphosphates are 2'-OMe in the reaction mixture, the cytidines triphosphates in reaction mixture are 2' deoxy. In some embodiments of the method in which all the guanidine triphosphates are 2'-OMe in the reaction mixture, the thymidine triphosphates in the reaction mixture are 2' deoxy. In some embodiments of the method in which all the guanidine triphosphates are 2'-OMe in the reaction mixture, the uridine triphosphates in the reaction mixture are 2'-OH. In some embodiments of the method in which all the guanidine triphosphates are 2'-OMe in the reaction mixture the uridine triphosphates in the reaction mixture are 2'-deoxy. In some embodiments of the method in which all the guanidine triphosphates are 2'-OMe in the reaction mixture, the cytidine triphosphates are 2'-deoxy and the thymidine and adenosine triphosphates are 2'-OMe. In some embodiments of the method in which all the guanidine triphosphates are 2'-OMe in the reaction mixture, the cytidine triphosphates are 2'-deoxy and the uridine and adenosine triphosphates are 2'-OMe. In some embodiments of the method in which all the guanidine triphosphates are 2'-OMe in the reaction mixture, the thymidine triphosphates 2'-deoxy and the uridine and adenosine triphosphates are 2'-OMe. In some embodiments of the method in which all the guanidine triphosphates are 2'-OMe in the reaction mixture, the uridine triphosphates are 2'-deoxy and the uridine and adenosine triphosphates are 2'-OMe. In some embodiments of the method in which all the guanidine triphosphates are 2'-OMe in the reaction mixture, the uridine triphosphates are 2'-OH and the uridine and adenosine triphosphates are 2'-OMe.

In some embodiments of the transcription methods of the invention, the transcription reaction mixture further comprises magnesium ions. In another embodiment, the transcription reaction further comprises manganese ions. In some embodiments, the transcription reaction further comprises both magnesium and manganese ions. In another embodiment, the magnesium ions are present in the transcription reaction mixture at a concentration that is between 3.0 to 3.5 times greater than the manganese ions. In another embodiment, wherein each nucleotide triphosphate is present in the transcription reaction mixture at a concentration of 1.0 mM, the concentration of magnesium ions is 6.5 mM, and the concentration of manganese ions is 2.0 mM. In another embodiment, wherein each nucleotide triphosphate is present in the transcription reaction mixture at a concentration of 1.5 mM, the concentration of magnesium ions 8 mM, and the concentration of manganese ions is 2.5 mM. In another embodiment, wherein each nucleotide triphosphate is present in the transcription reaction mixture at a concentration of 2.0 mM, the concentration of magnesium ions 9.5 mM and concentration of manganese ions is 3.0 mM.

In another embodiment, the transcription reaction mixture comprises a non 2'-OMe guanosine non-triphosphate residue, particularly wherein the non 2'-OMe guanosine non-triphosphate residue selected from the group consisting of: guanosine monophosphate, guanosine diphosphate, 2' fluoro guanosine monophosphate, 2' fluoro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase. In some embodiments, the transcription reaction further comprises both magnesium and manganese ions.

In another embodiment, a method for identifying an aptamer, comprising: a) preparing a transcription reaction mixture comprising a mutant polymerase, one or more nucleic acid transcription templates and nucleoside triphosphates, wherein the guanidine triphosphates are 2'-OMe, and b) transcribing the transcription reaction mixture under conditions that result in a candidate mixture of single stranded nucleic acids, wherein all but optionally one of the guanosine nucleotides of the single stranded nucleic acids are 2'-modified, c) contacting the candidate mixture with the target molecule, d) partitioning the nucleic acids having an increased affinity for a target molecule, relative to an affinity of the candidate mixture, from the candidate mixture, and e) amplifying the increased affinity nucleic acids to yield an aptamer enriched mixture, whereby an aptamer to the target molecule comprising all 2'-modified guanidine nucleotides, except that the first nucleotide of the aptamer, is identified, is provided. In one embodiment, the amplifying step comprises (i) optionally dissociating the increased affinity nucleic acids from the target, ii) reverse transcribing the increased affinity nucleic acids dissociated from the nucleic acid-target complexes, iii) amplifying the reverse transcribed increased affinity nucleic acids; and (ii) preparing a transcription reaction mixture comprising the amplified reverse transcribed increased affinity nucleic acids as the transcription template and transcribing the transcription mixture.

In some embodiments of the aptamer identification methods of the invention, the mutant polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine. In a further embodiment, the altered amino acid at position 378 is an arginine. In a particular embodiment, the aptamer identification methods of the invention use a polymerase comprising an amino acid selected from the group consisting of: SEQ ID NO 1, SEQ ID NO 2. SEQ ID NO 5 and SEQ ID NO 6. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In some embodiments of the aptamer identification methods in which all the guanidine triphosphates are 2'-OMe in the reaction mixture, the cytidines triphosphates in reaction mixture are 2' deoxy. In some embodiments of the method in which all the guanidine triphosphates are 2'-OMe in the reaction mixture, the thymidine triphosphates in the reaction mixture are 2' deoxy. In some embodiments of the method in which all the guanidine triphosphates are 2'-OMe in the reaction mixture, the uridine triphosphates in the reaction mixture are 2'-OH. In some embodiments of the method in which all the guanidine triphosphates are 2'-OMe in the reaction mixture, the uridine triphosphates in the reaction mixture are 2'-deoxy. In some embodiments of the method in which all the guanidine triphosphates are 2'-OMe in the reaction mixture, the cytidine triphosphates are 2'-deoxy and the thymidine and adenosine triphosphates are 2'-OMe. In some embodiments of the method in which all the guanidine triphosphates are 2'-OMe in the reaction mixture, the cytidine triphosphates are 2'-deoxy and the uridine and adenosine triphosphates are 2'-OMe. In some embodiments of the method in which all the guanidine triphosphates are 2'-OMe in the reaction mixture, the thymidine triphosphates 2'-deoxy and the uridine and adenosine triphosphates are 2'-OMe: In some embodiments of the method in which all the guanidine triphosphates are 2'-OMe in the reaction mixture, the uridine triphosphates are 2'-deoxy and the uridine and adenosine triphosphates are 2'-OMe. In some embodiments of the method in which all the guanidine triphosphates are 2'-OMe in the reaction mixture, the uridine triphosphates are 2'-OH and the uridine and adenosine triphosphates are 2-OMe.

In some embodiments of the aptamer identification methods of the invention, the transcription reaction mixture further comprises magnesium ions. In another embodiment, the transcription reaction further comprises manganese ions. In some embodiments, the transcription reaction further comprises both magnesium and manganese ions. In another embodiment, the magnesium ions are present in the transcription reaction mixture at a concentration that is between 3.0 to 3.5 times greater than the manganese ions. In another embodiment, wherein each nucleotide triphosphate is present in the transcription reaction mixture at a concentration of 1.0 mM, the concentration of magnesium ions is 6.5 mM, and the concentration of manganese ions is 2.0 mM. In another embodiment, wherein each nucleotide triphosphate is present in the transcription reaction mixture at a concentration of 1.5 mM, the concentration of magnesium ions 8 mM, and the concentration of manganese ions is 2.5 mM. In another embodiment, wherein each nucleotide triphosphate is present in the transcription reaction mixture at a concentration of 2.0 mM, the concentration of magnesium ions 9.5 mM and concentration of manganese ions is 3.0 mM.

In another embodiment, the transcription reaction mixture comprises a non 2'-OMe guanosine non-triphosphate residue, particularly wherein the non 2'-OMe guanosine non-triphosphate residue selected from the group consisting of: guanosine monophosphate, guanosine diphosphate, 2' fluoro guanosine monophosphate, 2' fluoro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase. In some embodiments, the transcription reaction further comprises both magnesium and manganese ions.

In another embodiment, a method of transcribing a nucleic acid comprising the steps of: a) preparing a transcription reaction mixture comprising a mutant T7 RNA polymerase, at least one nucleic acid transcription template and nucleotide triphosphates, wherein the nucleotide triphosphates comprise guanidine triphosphates and wherein all of the guanidine triphosphates are 2'-OMe modified; and b) transcribing the transcription reaction mixture under conditions that result in a single stranded nucleic acid, wherein all of the guanidine nucleotides of the resulting single stranded nucleic acid, except optionally one, are 2'-OMe modified is provided. In another embodiment, a method for identifying an aptamer, comprising: a) preparing a transcription reaction mixture comprising a mutant T7 RNA polymerase, at least one nucleic acid transcription template and nucleotide triphosphates, wherein the nucleotide triphosphates comprise guanidine triphosphates and wherein all of the guanidine triphosphates are 2'-OMe modified; b) transcribing the transcription reaction mixture under conditions that result in a candidate mixture of single stranded nucleic acids, wherein all but optionally one of the guanidine nucleotides of the single stranded nucleic acids are 2'-OMe modified; c) contacting the candidate mixture with the target molecule; d) partitioning the nucleic acids having an increased affinity for a target molecule, relative to an affinity of the candidate mixture, from the candidate mixture; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified is provided. In some embodiments, the amplifying step further comprises (i) optionally dissociating the increased affinity nucleic acids from the target, ii) reverse transcribing the increased affinity nucleic acids dissociated from the nucleic acid-target complexes, iii) amplifying the reverse transcribed increased affinity nucleic acids; and (ii) preparing a transcription reaction mixture comprising the amplified reverse transcribed increased affinity nucleic acids as the transcription template and transcribing the transcription mixture. In some embodiments, the method further comprises repeating steps a) through e) iteratively.

In some embodiments of this aspect of the method of the invention, the mutant T7 RNA polymerase comprises an altered amino acid at position 639 and at position 784 relative to wild type T7 polymerase, wherein altered amino acid at position 639 is not phenylalanine when the altered amino acid at position 784 is alanine, particularly where the mutant T7 RNA polymerase comprises a leucine at position 639 and an alanine at position 784. In some embodiments, the mutant T7 RNA polymerase further comprises an altered amino acid, relative to wild type, at position 378 and/or position 266. In a further embodiment, the altered amino acid at position 266 is a leucine. In a further embodiment, the altered amino acid at position 378 is an arginine. In a particular embodiment, an isolated polypeptide comprising an amino acid selected from the group consisting of: SEQ ID NO 1, SEQ ID NO 2, SEQ ID NO 5 and SEQ ID NO 6 is used in the method of the invention. In some embodiments, the template nucleic acid, also referred to an oligonucleotide transcription template, is at least partially double-stranded. For example, the template nucleic acid is at least 10%, 25%, 50%, 60%, 70%, 75%, 80%, 85%, 90%, 91%, 92%, 93%, 94%, 95%, 96%, 97%, 98%, or 99% double-stranded across the length of the template. In some embodiments, the template nucleic acid is fully double-stranded across the length of the template.

In some embodiments, the transcription reaction mixture further comprises at least two additional different kinds of nucleotide triphosphates selected from the group consisting of cytidine triphosphates, uridine triphosphates, thymidine triphosphates and adenosine triphosphates, particularly where at least two additional different kinds of nucleotide triphosphates are 2'-OMe modified, more particularly where all of the different kinds of nucleotide triphosphates comprised in the transcription reaction mixture are 2'-OMe modified.

In some embodiments of this aspect of the method of the invention, at least one kind of the nucleotide triphosphates comprises a nucleobase modified with a side chain. A side chain as used herein encompasses an organic side chain comprising at least two atoms wherein at least one atom is carbon and at least one other atom is not monovalent. In one embodiment, the nucleobase is modified at a position selected from the group consisting of: the 5- and 6-positions of uridine, the 5- and 6-positions of thymidine, the 5 and 6-positions and the exocyclic amine of cytidine, the 2-, 7- and 8-positions and the exocyclic amine of adenosine, the 7- and 8-positions and the exocyclic amine of guanosine, particularly where nucleo base, e.g. pyrimidine, is modified at position 5, more particularly where the modified nucleobase is a uracil or cytosine. In some embodiments, the side chain is a hydrophobic and/or aromatic side chain, particularly a benzyl or indolyl side chain.

In some embodiments, the nucleobase is modified directly with the side chain while in some embodiments the nucleobase is modified with a linker covalently attached to the side chain, wherein the linker is selected from the group consisting of: —O—, —NH—, —CO— (carboxy) and $—CH_2—$, —CO—O— and —CO—NH— and $—CH_2—CO—NH—(CH_2)_n—NH—$ wherein n is 1 to 6, particularly where the linker is selected from the group consisting of: —CO— (carboxy) and $—CH_2—$ and —CO—NH—.

In some embodiments, the nucleotide comprising the modified nucleobase is 2'-OMe. In particular embodiments, all the different kinds of nucleotide triphosphates comprised in the transcription reaction mixture are 2'-OMe modified including the kind of nucleotide comprising the modified nucleobase. In a particular embodiment, the nucleotide comprising the modified nucleobase is 2'-O-methyl-5-indolylmethylene U or 2'-O-methyl-5-benzyl U. In other embodiments, the nucleotide comprising the modified nucleobase is 2'-deoxy or 2'-OH.

In some embodiments, the transcription reaction further comprises magnesium ions. In another embodiment, the transcription reaction further comprises manganese ions. In some embodiments, the transcription reaction further comprises both magnesium and manganese ions. In another embodiment, the magnesium ions are present in the transcription reaction at a concentration that is between 3.0 to 3.5 times greater than the manganese ions. In another embodiment, wherein each nucleotide triphosphate is present in the transcription reaction at a concentration of 1.0 mM, the concentration of magnesium ions is 6.5 mM, and the concentration of manganese ions is 2.0 mM. In another embodiment, wherein each nucleotide triphosphate is present in the transcription reaction at a concentration of 1.5 mM, the concentration of magnesium ions 8 mM, and the concentration of manganese ions is 2.5 mM. In another embodiment, wherein each nucleotide triphosphate is present in the transcription reaction at a concentration of 2.0 mM, the concentration of magnesium ions 9.5 mM and concentration of manganese ions is 3.0 mM.

In some embodiments, the transcription reaction mixture comprises a non 2'-OMe guanosine non-triphosphate residue, particularly wherein the non 2'-OMe guanosine non-triphosphate residue selected from the group consisting of: guanosine monophosphate, guanosine diphosphate, 2' fluoro guanosine monophosphate, 2' fluoro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In some embodiments, the nucleic acid transcription template comprised in the transcription reaction mixture, comprises a T7 RNA polymerase promoter and a leader sequence immediately 3' to the T7 RNA polymerase promoter. In another embodiment, the transcription reaction further comprises polyethylene glycol. In another embodiment, the transcription reaction further comprises inorganic pyrophosphatase. In some embodiments, the transcription reaction further comprises both magnesium and manganese ions.

In some embodiments of this aspect of the method of the invention, the transcribing step results in a transcriptional yield of single stranded nucleic acids, wherein the transcriptional yield is higher than that of an identical transcription reaction except that the identical transcription reaction comprises a wild type T7 RNA polymerase. Transcriptional yield is quantitated by electrophoresis and visualization and can be expressed by a transcript copy number and/or concentration, e.g. μM or μg/ml. In this aspect of the method of the invention, wild type T7 polymerase comprises an amino acid sequence according to SEQ ID NO 33.

BRIEF DESCRIPTION OF THE DRAWINGS

FIG. 3A shows the nucleic acid (SEQ ID NO 32) and FIG. 3B gives the amino acid sequence of the wild type T7 RNA polymerase (SEQ ID NO 33).

FIG. 4A shows the nucleic acid sequence (SEQ ID NO 34) of mutant T7 RNA polymerase Y639L/H784A. FIG. 4B shows the nucleic acid sequence (SEQ ID NO 35) of T7 mutant polymerase Y639L/H784A/K378R. FIG. 4C shows the nucleic acid sequence (SEQ ID NO 36) of mutant T7 polymerase P266L/Y639L/H784A. FIG. 4D shows the nucleic acid sequence (SEQ ID NO 37) of mutant T7 polymerase P266L/Y639L/H784A/K378R.

FIG. 5 shows the relative transcript yield quantitated from UV-shadowing of PAGE-gel analysis for ARC2118 and ARC2119 using the Y639L/H784A/K378R mutant T7 RNA polymerase with a titration of rGTP (2'-OH GTP) in the transcription mixture. * indicates that the given yields are relative to ARC2118 transcribed with 20 uM rGTP, which gave the highest quantitated yield by UV-shadow.

FIG. 6 shows the relative transcript yield quantitated from UV-shadowing of PAGE-gel analysis for ARC2119 using the Y639L/H784A/K378R mutant T7 RNA polymerase with a varying concentrations of 2'-OMe NTPs (2'-OMe ATP, 2'-OMe UTP, 2'-OMe CTP, and 2'-OMe GTP), $MgCl_2$ and $MnCl_2$ and no rGTP (2'-OH GTP) in the transcription mixture. The given yields are relative to the 1 mM each 2'-OMe NTP, 6.5 mM $MgCl_2$, and 2 mM $MnCl_2$ transcription condition.

FIG. 7 is a table that shows an analysis of the nucleotide insertions, deletions and substitutions of fully 2'-OMe transcription (100% 2'-OMe ATP, 2'-OMe UTP, 2'-OMe CTP, and 2'-OMe GTP) with the Y639L/H784A/K378R mutant T7 RNA polymerase, compared to the fidelity of all RNA or 2'-OMe transcription using the Y639F/K378R mutant T7 RNA polymerase. In the table, (1) indicates data from "Direct in Vitro Selection of a 2'-O-Methyl Aptamer to VEGF" Burmeister et. al., (2005) Chemistry and Biology, 12: 25-33 where transcriptions were done with FAR T7 mutant polymerase and (2) indicates that transcription was done with LAR T7 mutant polymerase.

FIG. 8 is a table that shows an analysis of the percent nucleotide composition of fully 2'-OMe transcripts (100% 2'-OMe ATP, 2'-OMe UTP, 2'-OMe CTP, and 2'-OMe GTP) before and after one round of fully 2'-OMe transcription using the Y639L/H784A/K378R mutant T7 RNA polymerase followed by DNase treatment, reverse transcription, splinted ligation, and PCR amplification.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

THE SELEX™ METHOD

Figure 1:
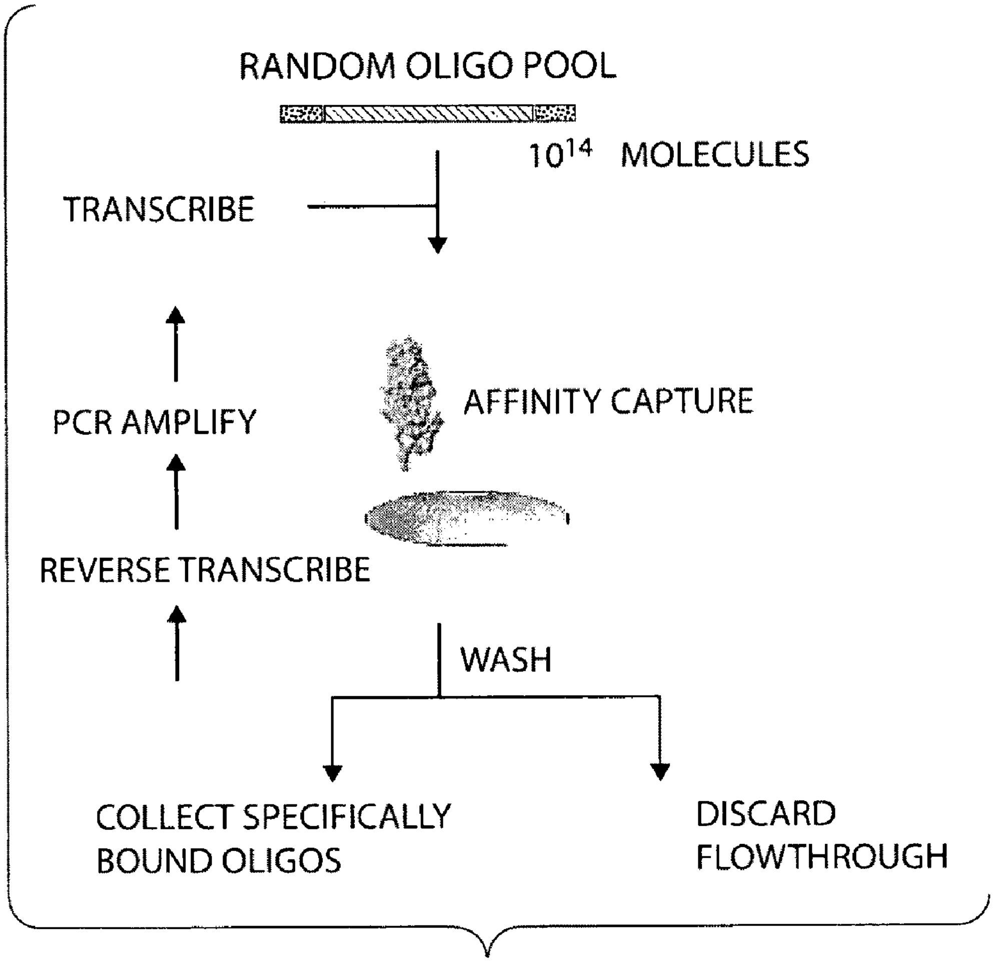
FIG. 1 is a schematic representation of the in vitro aptamer selection (SELEX™) process from pools of random sequence oligonucleotides.

The preferred method for generating an aptamer is with the process entitled "Systematic Evolution of Ligands by Exponential Enrichment" ("SELEX™") generally depicted in FIG. 1 and also referred to as in vitro selection. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". By performing iterative cycles of selection and amplification SELEX™ may be used to obtain aptamers, also referred to herein as "nucleic acid ligands" with any desired level of target binding affinity.

The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

The SELEX™ process is based on the ability to bind a target. Aptamers obtained through the SELEX™ procedure will thus have the property of target binding. Mere target binding, however provides no information on the functional effect, if any, which may be exerted on the target by the action of aptamer binding.

Alteration of a property of the target molecule requires the aptamer to bind at a certain location on the target in order to effect a change in a property of the target. In theory, the SELEX™ method may result in the identification of a large number of aptamers, where each aptamer binds at a different site on the target. In practice, aptamer-target binding interactions often occur at one or a relatively small number of preferred binding sites on the target which provide stable and accessible structural interfaces for the interaction. Furthermore, when the SELEX™ method is performed on a physiological target molecule the skilled person is generally not able to control the location of aptamer to the target. Accordingly, the location of the aptamer binding site on the target may or may not be at, or close to, one of potentially several binding sites that could lead to the desired effect, or may not have any effect on the target molecule.

Even where an aptamer, by virtue of its ability to bind the target, is found to have an effect there is no way of predicting the existence of that effect or of knowing in advance what the effect will be. In performing a SELEX™ experiment the skilled person can only know with any certainty that aptamers, to the extent it is possible to obtain an aptamer against a target, will have the property of target binding. One may perform a SELEX™ experiment in the hope that some of the aptamers identified will also have an effect on the target beyond binding to it, but this is uncertain.

The SELEX™ process relies as a starting point upon a large library or pool of single stranded oligonucleotides comprising randomized sequences. The oligonucleotides can be modified or unmodified DNA, RNA, or DNA/RNA hybrids. In some examples, the pool comprises 100% degenerate or partially degenerate oligonucleotides. In other examples, the pool comprises degenerate or partially degenerate oligonucleotides containing at least one fixed sequence and/or conserved sequence incorporated within randomized sequence. In other examples, the pool comprises degenerate or partially degenerate oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs described further below, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, leader sequences which promote transcription, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a degenerate sequence portion as well as fixed sequences necessary for efficient amplification. Typically the oligonucleotides of the starting pool contain fixed 5' and 3' terminal sequences which flank an internal region of 30-40 random nucleotides. The degenerate nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The degenerate sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Degenerate oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{16}$-$10^{17}$ individual molecules, a number sufficient for most SELEX™ experiments. Sufficiently large regions of degenerate sequence in the sequence design increases the likelihood that each synthesized molecule is likely to represent a unique sequence.

The starting library of oligonucleotides may be generated by automated chemical synthesis on a DNA synthesizer. To synthesize degenerate sequences, mixtures of all four nucleotides are added at each nucleotide addition step during the synthesis process, allowing for stochastic incorporation of nucleotides. As stated above, in one embodiment, random oligonucleotides comprise entirely degenerate sequences; however, in other embodiments, degenerate oligonucleotides can comprise stretches of nonrandom or partially random sequences. Partially random sequences can be created by adding the four nucleotides in different molar ratios at each addition step.

In those instances where an RNA library is to be used as the starting library it is typically generated by synthesizing a DNA library, optionally PCR amplifying, then transcribing the DNA library in vitro using T7 RNA polymerase or a modified T7 RNA polymerase, and purifying the transcribed library. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) optionally dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and/or 2) ability to effect target function Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of the SELEX™ method, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of the SELEX™ process until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 40 nucleotides.

The core SELEX™ method has been modified to achieve a number of specific objectives. For example, U.S. Pat. No. 5,707,796 describes the use of the SELEX™ process in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

The SELEX™ method can also be used to obtain nucleic acid ligands that bind to more than one site on the target molecule, and to obtain nucleic acid ligands that include non-nucleic acid species that bind to specific sites on the target. The SELEX™ method provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through the SELEX™ method which are capable of binding with high affinity to caffeine and the closely related analog, theophylline.

The Counter-SELEX™ process is a method for improving the specificity of nucleic acid ligands to a target molecule by eliminating nucleic acid ligand sequences with cross-reactivity to one or more non-target molecules. The Counter-SELEX™ process is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) optionally dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for the SELEX™ method, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the sugar and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2'-position of ribose, 5-position of pyrimidines, and 8-position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping. Modifications can also include 3' and 5' modifications such as capping, e.g., addition of a 3'-3'-dT cap to increase exonuclease resistance (see, e g. U.S. Pat. Nos. 5,674,685; 5,668,264; 6,207,816; and 6,229,002, each of which is incorporated by reference herein in its entirety).

In one embodiment, oligonucleotides are provided in which the P(O)O group is replaced by P(O)S ("thioate"), P(S)S ("dithioate"), P(O)$NR_2$ ("amidate"), P(O)R', P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both specificity for their SELEX™ target and improved stability, e.g., in vivo stability. Post-SELEX™ process modifications ((e.g., truncation, deletion, substitution or additional nucleotide modifications of previously identified ligands having nucleotides incorporated by pre-SELEX™ process modification) to nucleic acid ligands can result in improved stability, e.g., in vivo stability without adversely affecting the binding capacity of the nucleic acid ligand. Optionally, aptamers in which modified nucleotides have been incorporated by pre-SELEX™ process modification can be further modified by post-SELEX™ process modification (i.e., a post-SELEX™ modification process after SELEX).

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

As part of the SELEX™ process, the sequences selected to bind to the target are then optionally minimized to determine the minimal sequence having the desired binding affinity. The selected sequences and/or the minimized sequences are optionally modified by performing random or directed mutagenesis of the sequence to, e.g., increase binding affinity or alternatively to determine which positions in the sequence are essential for binding activity.

THE MODIFIED NUCLEOTIDE SELEX™ METHOD

In order for an aptamer to be suitable for use as a therapeutic and/or for particular types of diagnostics, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

Furthermore, incorporating chemical modifications into oligonucleotide libraries from which aptamers are selected increases the structural and chemical diversity of the oligonucleotide libraries potentially increasing the numbers of targets to which high affinity and highly specific aptamers having particularly desired characteristics may be obtained. For example, while for many applications it may be desirable to obtain fully 2'-OMe aptamers it may not always be possible to obtain such aptamers from a single pool composition, e.g. oligonucleotides in which all but the first nucleotide are 2'-OMe, that result in aptamers that modulate, e.g. inhibit, the function of the target to a sufficient degree for a given application. In this instance, it would be desirable select aptamers from other pool compositions such as a pool comprising oligonucleotides in which all but one nucleotide is 2'-OMe, such as a library obtained from a dCmD transcription composition. It may also be desirable and the in another embodiment the invention provides a method to select aptamers from a pool composition comprising oligonucleotides having 2'-OMe modifications as well as a side chain modification of a position on the nucleo base.

2'-fluoro and 2'-amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. SELEX™ methods used to generate 2'-modified aptamers are described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003, U.S. patent application Ser. No. 10/873,856, filed Jun. 21, 2004, entitled "Method for in vitro Selection of 2'-O-methyl Substituted Nucleic Acids," U.S. Provisional Patent Application No. 60/696,292, filed Jun. 30, 2005, entitled Materials and Methods for the Generation of Fully 2'-Modified Nucleic Acid Transcripts and U.S. patent application Ser. No. 11/480,188, filed Jun. 30, 2006, entitled Materials and Methods for the Generation of Fully 2'-Modified Nucleic Acid Transcripts, each of which is herein incorporated by reference in its entirety.

The present invention includes aptamers that bind to and modulate the function of the aptamer target and which contain modified nucleotides (e.g., nucleotides which have a modification at the 2'-position) to make the oligonucleotide more stable than the unmodified oligonucleotide to enzymatic and chemical degradation as well as thermal and physical degradation. The present invention also includes aptamers that bind to and modulate the function of an aptamer target and which contain nucleotides modified at the 2' position, e.g. 2'-OMe modified, and at a position on a nucleobase, e.g. side chain modification at position 5 of a pyrimidine. Although there are several examples of 2'-OMe containing aptamers in the literature (see, e.g., Ruckman et al., J. Biol. Chem., 1998 273, 20556-20567-695) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by the SELEX™ method (and/or any of its variations and improvements, including those described herein), the methods of the present invention eliminate the need for stabilizing the selected aptamer oligonucleotides by resynthesizing the aptamer oligonucleotides with 2'-OMe modified nucleotides.

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'—$NH_2$, and 2'-methoxyethyl modifications of the ATP, GTP, CTP, TTP, and UTP nucleotides. In a preferred embodiment, the present invention provides aptamers comprising all or substantially all 2'-OMe modified ATP, GTP, CTP, TTP, and/or UTP nucleotides. In another preferred embodiment, the present invention provides aptamers in which all the nucleotide triphosphates groups, ATP, GTP, CTP, TTP and/or UTP are 2'-OMe modified except for one. For example, aptamers comprising 2'-OMe ATP, GTP, TTP but in which the CTP is deoxy. The present invention further provides aptamers comprising nucleo base modification with a side chain in combination with any of the preceding 2' modified combinations.

In another preferred embodiment, the present invention provides aptamers comprising three 2'-OMe modified nucleotide triphosphate groups and one deoxy or 2'-OH nucleotide triphosphate group except that the starting nucleotide does not have to be 2' modified. In a particular embodiment, the aptamer comprises deoxy cytidine nucleotide triphosphates and the remaining nucleotide triphosphates are 2'-OMe modified except that the starting nucleotide does not have to be 2' modified. In another embodiment, the aptamer comprises deoxy thymidine nucleotide triphosphates and the remaining nucleotide triphosphates are 2'-OMe modified except that the starting nucleotide does not have to be 2' modified. In another embodiment, the aptamer comprises 2'-OH uridine nucleotide triphosphates and the remaining nucleotide triphosphates are 2'-OMe modified except that the starting nucleotide does not have to be 2' modified. In another embodiment, the aptamer comprises deoxy guanosine nucleotide triphosphates and the remaining nucleotides are 2'-OMe modified except that the starting nucleotide does not have to be 2' modified. In another embodiment, the aptamer comprises deoxy adenosine nucleotide triphosphates and the remaining nucleotides are 2'-OMe modified except that the starting nucleotide does not have to be 2' modified.

Modified Polymerases

2'-modified aptamers of the invention are created using modified polymerases, e.g., a mutated T7 polymerase, having a rate of incorporation of modified nucleotides having bulky substituents at the furanose 2' position that is higher than that of wild-type polymerases, e.g. wild type T7 polymerase. For example, a mutant T7 polymerase in which the tyrosine residue at position 639 has been changed to phenylalanine (Y639F) readily utilizes 2' deoxy, 2' amino-, and 2' fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-$N_3$) substituents. For incorporation of bulky 2' substituents, a mutant T7 polymerase having the histidine at position 784 changed to an alanine residue in addition to the Y639F mutation has been described (Y639F/H784A) and has been used in limited circumstances to incorporate modified pyrimidine NTPs. See Padilla, R. and Sousa, R., Nucleic Acids Res., 2002, 30 (24): 138. A mutant T7 RNA polymerase in which the tyrosine residue at position 639 has been changed to phenylalanine, the histidine residue at position 784 has been changed to an alanine, and the lysine residue at position 378 has been changed to arginine (Y639F/H784A/K378R) has been used in limited circumstances to incorporate modified purine and pyrimidine NTPs, e.g., 2'-OMe NTPs, but includes a spike of 2'-OH GTP for transcription. See Burmeister et. al., (2005)

Chemistry and Biology, 12: 25-33. The inclusion of a 2'-OH GTP spike for transcription may result in aptamers that are not fully 2'-OMe but rather may depend on the presence of 2'-OH GTPs.

A mutant T7 polymerase having the histidine at position 784 changed to an alanine residue (H784A) has also been described. Padilla et al., Nucleic Acids Research, 2002, 30: 138. In both the Y639F/H784A mutant and H784A mutant T7 polymerases, the change to a smaller amino acid residue such as alanine allows for the incorporation of bulkier nucleotide substrates, e.g., 2'-OMe substituted nucleotides. See Chellisery, K. and Ellington, A. D., (2004) Nature Biotech, 9:1155-60. Additional T7 RNA polymerases have been described with mutations in the active site of the T7 RNA polymerase which more readily incorporate bulky 2'-modified substrates, e.g., a mutant T7 RNA polymerase having the tyrosine residue at position 639 changed to a leucine (Y639L). However activity is often sacrificed for increased substrate specificity conferred by such mutations, leading to low transcript yields. See Padilla R and Sousa, R., (1999) Nucleic Acids Res., 27 (6): 1561. The T7 RNA polymerase mutant P266L has been described to facilitate promoter clearance (Guillerez et al. (2005) Proc. Nat. Acad. Sci. USA, 102 (17) 5958). The polymerase makes a transition from the initiation conformation, in which it is bound to the promoter, to the elongation conformation in which it is not. None of the above mutant polymerases were reported to result in fully 2'-OMe transcripts.

The present invention provides materials and methods for increasing the transcription yield of oligonucleotides. In one embodiment, the present invention provides methods and conditions for using modified T7 RNA polymerases (modification of T7 RNA polymerase is relative to wild type T7 RNA polymerase, SEQ ID NO 33) to enzymatically incorporate modified nucleotides into oligonucleotides. In a preferred embodiment, the mutated T7 RNA polymerase used with the transcription methods of the invention does not require the presence of 2'-OH GTP. In a preferred embodiment, the modified polymerase is a mutant T7 RNA polymerase having the tyrosine residue at position 639 changed to a leucine residue and the histidine residue at position 784 changed to an alanine residue (Y639L/H784A). In another preferred embodiment, the modified polymerase is a mutant T7 RNA polymerase having the tyrosine residue at position 639 changed to a leucine residue, the histidine residue at position 784 changed to an alanine residue, and the lysine residue at position 378 changed to an arginine residue (Y639L/H784A/K378R). In another embodiment, the modified polymerase for use in the methods of the invention is a mutant T7 RNA polymerase having the tyrosine residue at position 639 changed to a leucine (Y639L) while in yet another embodiment the mutant T7 RNA polymerase has the tyrosine residue at position 639 changed to a leucine residue and the lysine residue at position 378 changed to an arginine residue (Y639L/K378R). While not wishing to be bound by any theory, the K378R mutation is not near the active site of the polymerase and thus is believed to be a silent mutation. In another embodiment, the modified polymerase for use in the methods of the invention is a mutant T7 RNA polymerase having the proline residue at position 266 changed to a leucine, the tyrosine residue at position 639 changed to a leucine and the histidine residue at position 784 changed to an alanine residue, (P266L/Y639L/H784A) while in yet another embodiment the mutant T7 RNA polymerase has the proline residue at position 266 changed to a leucine, the tyrosine residue at position 639 changed to a leucine residue, the histidine residue at position 784 changed to an alanine residue and the lysine residue at position 378 changed to an arginine residue (P266L/Y639L/H784A/K378R).

The amino acid sequences of the mutant T7 RNA polymerases are shown below:

```
Y639L/H784A (SEQ ID NO 1):
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISPMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWKRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPLAFDGSCSGIQHFSAML
RDEVGGRAVNLLPSETVQDIYGIVAKKVNEILQADAINGTDNEVVTVTDE
NTGEISEKVKLGTKALAGQWLAYGVTRSVTKRSVMTLALGSKEFGFRQQV
LEDTIQPAIDSGKGLMFTQPNQAAGYMAKLIWESVSVTVVAAVEAMNWLK
SAAKLLAAEVKDKKTGEILRKRCAVHWVTPDGFPVWQEYKKPIQTRLNLM
FLGQFRLQPTINTNKDSEIDAHKQESGIAPNFVASQDGSHLRKTVVWAHE
KYGIESFALIHDSFGTIPADAANLFKAVRETMVDTYESCDVLADFYDQFA
DQLHESQLDKMPALPAKGNLNLRDILESDFAFA
```

```
Y639L/H784A/K378R (SEQ ID NO 2):
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISPMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWRRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPLAFDGSCSGIQHFSAML
RDEVGGRAVNLLPSETVQDIYGIVAKKVNEILQADAINGTDNEVVTVTDE
NTGEISEKVKLGTKALAGQWLAYGVTRSVTKRSVMTLALGSKEFGFRQQV
LEDTIQPAIDSGKGLMFTQPNQAAGYMAKLIWESVSVTVVAAVEAMNWLK
SAAKLLAAEVKDKKTGEILRKRCAVHWVTPDGFPVWQEYKKPIQTRLNLM
FLGQFRLQPTINTNKDSEIDAHKQESGIAPNFVASQDGSHLRKTVVWAHE
KYGIESFALIHDSFGTIPADAANLFKAVRETMVDTYESCDVLADFYDQFA
DQLHESQLDKMPALPAKGNLNLRDILESDFAFA
```

```
Y639L (SEQ ID NO 3):
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISPMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWKRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPLAFDGSCSGIQHFSAML
RDEVGGRAVNLLPSETVQDIYGIVAKKVNEILQADAINGTDNEVVTVTDE
NTGEISEKVKLGTKALAGQWLAYGVTRSVTKRSVMTLALGSKEFGFRQQV
LEDTIQPAIDSGKGLMFTQPNQAAGYMAKLIWESVSVTVVAAVEAMNWLK
SAAKLLAAEVKDKKTGEILRKRCAVHWVTPDGFPVWQEYKKPIQTRLNLM
FLGQFRLQPTINTNKDSEIDAHKQESGIAPNFVHSQDGSHLRKTVVWAHE
KYGIESFALIHDSFGTIPADAANLFKAVRETMVDTYESCDVLADFYDQFA
DQLHESQLDKMPALPAKGNLNLRDILESDFAFA
```

```
Y639L/K378R (SEQ ID NO 4):
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISPMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWRRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPLAFDGSCSGIQHFSAML
RDEVGGRAVNLLPSETVQDIYGIVAKKVNEILQADAINGTDNEVVTVTDE
NTGEISEKVKLGTKALAGQWLAYGVTRSVTKRSVMTLALGSKEFGFRQQV
LEDTIQPAIDSGKGLMFTQPNQAAGYMAKLIWESVSVTVVAAVEAMNWLK
SAAKLLAAEVKDKKTGEILRKRCAVHWVTPDGFPVWQEYKKPIQTRLNLM
FLGQFRLQPTINTNKDSEIDAHKQESGIAPNFVHSQDGSHLRKTVVWAHE
```

-continued

```
KYGIESFALIHDSFGTIPADAANLFKAVRETMVDTYESCDVLADFYDQFA
DQLHESQLDKMPALPAKGNLNLRDILESDFAFA

P266L/Y639L/H784A (SEQ ID NO 5)
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISLMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWKRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPLAFDGSCSGIQHFSAML
RDEVGGRAVNLLPSETVQDIYFIVAKKVNEILQADAINGTDNEVVTVTDE
NTGEISEKVKLGTKALAGQWLAYGVTRSVTKRSVMTLALGSKEFGFRQQV
LEDTIQPAIDSGKGLMFTQPNQAAGYMAKLIWESVSVTVVAAVEAMNWLK
SAAKLLAAEVKDKKTGEILRKRCAVHWVTPDGFPVWQEYKKPIQTRLNLM
FLGQFRLQPTINTNKDSEIDAHKQESGIAPNFVASQDGSHLRKTVVWAHE
KYGIESFALIHDSFGTIPADAANLFKAVRETMVDTYESCDVLADFYDQFA
DQLHESQLDKMPALPAKGNLNLRDILESDFAFA

P266L/Y639L/H784A/K378R (SEQ ID NO 6)
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYKKAFMQVVEADMLSKGLLGGEA
WSSWHKEDSIHVGVRCIEMLIESTGMVSLHRQNAGVVGQDSETIELAPEY
AEAIATRAGALAGISLMFQPCVVPPKPWTGITGGGYWANGRRPLALVRTH
SKKALMRYEDVYMPEVYKAINIAQNTAWKINKKVLAVANVITKWKHCPVE
DIPAIEREELPMKPEDIDMNPEALTAWRRAAAAVYRKDKARKSRRISLEF
MLEQANKFANHKAIWFPYNMDWRGRVYAVSMFNPQGNDMTKGLLTLAKGK
PIGKEGYYWLKIHGANCAGVDKVPFPERIKFIEENHENIMACAKSPLENT
WWAEQDSPFCFLAFCFEYAGVQHHGLSYNCSLPAFDGSCSGIQHFSAMLR
DEVGGRAVNLLPSETVQDIYGIVAKKVNEILQADAINGTDNEVVTVTDEN
TGEISEKVKLGTKALAGQWLAYGVTRSVTKRSVMTLALGSKEFGFRQQVL
EDTIQPAIDSGKGLMFTQPNQAAGYMAKLIWESVSVTVVAAVEAMNWLKS
AAKLLAAEVKDKKTGEILRKRCAVHWVTPDGFPVWQEYKKPIQTRLNLMF
LGQFRLQPTINTNKDSEIDAHKQESGIAPNFVASQDGSHLRKTVVWAHEK
YGIESFALIHDSFGTIPADAANLFKAVRETMVDTYESCDVLADFYDQFAD
QLHESQLDKMPALPAKGNLNLRDILESDFAFA
```

To generate pools of 2'-modified (e.g., 2'-OMe or 2'-OMe and nucleo base side chain modification) RNA transcripts, the Y639F, Y639F/K378R, Y639F/H784A, Y639F/H784A/K378R, Y639L/H784A, Y639L/H784A/K378R, Y639L, Y639L/K378R, P266L/Y639L/H784A or P266L/Y639L/H784A/K378R mutant T7 RNA polymerases under conditions in which the mutant polymerase accepts 2'-modified NTPs can be used. A preferred polymerase is the Y639L/H784A mutant T7 RNA polymerase. Another preferred polymerase is the Y639L/H784A/K378R mutant T7 RNA polymerase. Another preferred polymerase of the invention is the P266L/Y639L/H784A or P266L/Y639L/H784A/K378R mutant T7 RNA polymerase. Other T7 RNA polymerases, particularly those that exhibit a high tolerance for bulky 2'-substituents, may also be used in the methods of the present invention. When used in a template-directed polymerization using the conditions disclosed herein, the Y639L/H784A, the Y639L/H784A/K378R, P266L/Y639L/H784A or P266L/Y639L/H784A/K378R mutant T7 RNA polymerase can be used for the incorporation of all 2'-OMe NTPs, including 2'-OMe GTP, and including 2'-OMe NTPS also side chain modified at a position on the nucleo base with higher transcript yields than achieved by using the Y639F, Y639F/K378R, Y639F/H784A, Y639F/H784A/K378R, Y639L, or the Y639L/K378R mutant T7 RNA polymerases. The Y639L/H784A, Y639L/H784A/K378R, P266L/Y639L/H784A or P266L/Y639L/H784A/K378R mutant T7 RNA polymerases can be used with but does not require 2'-OH GTP to achieve high yields of 2'-modified, e.g., 2'-OMe containing oligonucleotides.

In a preferred embodiment, the Y639L/H784A or the Y639L/H784A/K378R mutant T7 RNA polymerases of the invention are used with an MNA transcription mixture to promote higher fully 2'-OMe transcript yields. In some embodiments, at least one oligonucleotide of the MNA transcription mixture also comprises a side chain modification at a position on the nucleo base. In another preferred embodiment, the Y639L/H784A or the Y639L/H784A/K378R mutant T7 RNA polymerases of the invention are used with a dCmD, dTmV, rTmV, rUmV or dUmV transcription mixture to promote higher transcript yield in which all the guanosine triphosphates except the first nucleotide of the transcript are 2'-OMe. In some embodiments, the Y639L/H784A or the Y639L/H784A/K378R mutant T7 RNA polymerases of the invention are used with a dCmD, dTmV, rTmV, rUmV or dUmV transcription mixture wherein at least one nucleotide type in the mixture also comprise a side chain modification at a position on its nucleobase to promote higher transcript yield in which all the guanosine triphosphates except the first nucleotide of the transcript are 2'-OMe and one nucleotide type also comprises side chain modification of the nucleobase. In some embodiments, Y639L/H784A or the Y639L/H784A/K378R mutant T7 RNA polymerases may be used with an rRmY, dRmY, rGmH, fGmH, dGmH, dAmB, rRdY, dRdY or rN transcription mixture. In some embodiments, any one of the Y639L/H784A, Y639L/H784A/K378R, P266L/Y639L/H784A or P266L/Y639L/H784A/K378R mutant T7 RNA polymerases can be used in a dCmD, dTmV, rUmV, dUmV, dGmH, rGmH, alternating mixture, fGmH, rAmB or dAmB transcription reaction mixture. In a particular embodiment any one of the Y639L/H784A, Y639L/H784A/K378R, P266L/Y639L/H784A or P266L/Y639L/H784A/K378R mutant T7 RNA polymerases can be used in a dCmD, dTmV, rUmV or dUmV transcription reaction mixture.

As used herein, a transcription mixture containing only 2'-OMe A, G, C, and U triphosphates (2'-OMe ATP, 2'-OMe UTP, 2'-OMe CTP, and 2'-OMe GTP) is referred to as an MNA mixture, and aptamers selected therefrom are referred to as MNA aptamers and contains only 2'-O-methyl nucleotides. A transcription mixture containing 2'-OMe C and U and 2'-OH A and G is referred to as an “rRmY” mixture and aptamers selected therefrom are referred to as “rRmY” aptamers. A transcription mixture containing deoxy A and G and 2'-OMe U and C is referred to as a “dRmY” mixture and aptamers selected therefrom are referred to as “dRmY” aptamers. A transcription mixture containing 2'-OMe A, C, and U, and 2'-OH G is referred to as a “rGmH” mixture and aptamers selected therefrom are referred to as “rGmH” aptamers. A transcription mixture alternately containing 2'-OMe A, C, U and G and 2'-OMe A, U and C and 2'-F G is referred to as an “alternating mixture” and aptamers selected therefrom are referred to as “alternating mixture” aptamers. A transcription mixture containing 2'-OMe A, U, and C, and 2'-F G is referred to as a “fGmH” mixture and aptamers selected therefrom are referred to as “fGmH” aptamers. A transcription mixture containing 2'-OMe A, U, and C, and deoxy G is referred to as a “dGmH” mixture and aptamers selected therefrom are referred to as “dGmH” aptamers. A transcription mixture containing deoxy A, and 2'-OMe C, G and U is referred to as a “dAmB” mixture and aptamers selected therefrom are referred to as “dAmB” aptamers. A transcription mixture containing 2'-OH A and 2'-OMe C, G and U is referred to as a “rAmB” mixture and aptamers selected therefrom are referred to as “rAmB” aptamers. A transcription mixture containing 2'-OH adenosine triphosphate and guanosine triphosphate and deoxy cytidine triphosphate and thymidine triphosphate is referred to as an rRdY mixture and aptamers selected therefrom are referred to as “rRdY' aptamers. A transcription mixture containing 2'-OMe A, U or T, and G, and deoxy C is referred to as a "dCmD" mixture and aptamers selected there from are referred to as "dCmD" aptamers. A transcription mixture containing 2'-OMe A, G, and C, and deoxy T is referred to as a "dTmV" mixture and aptamers selected there from are referred to as "dTmV" aptamers. A transcription mixture containing 2'-OMe A, C, and G, and 2'-OH U is referred to as a "rUmV" mixture and aptamers selected there from are referred to as "rUmV" aptamers. A transcription mixture containing 2'-OMe A, C, and G, and 2'-deoxy U is referred to as a "dUmV" mixture and aptamers selected there from are referred to as "dUmV" aptamers. A transcription mixture containing all 2'-OH nucleotides is referred to as a "rN" mixture and aptamers selected therefrom are referred to as "rN", "rRrY" or RNA aptamers, and a transcription mixture containing all deoxy nucleotides is referred to as a "dN" mixture and aptamers selected therefrom are referred to as "dN" or "dRdY" or DNA aptamers.

2'-modified oligonucleotides may be synthesized entirely of modified nucleotides, or with a subset of modified nucleotides. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this manner, transcripts, or pools of transcripts are generated using any combination of modifications, including for example, ribonucleotides (2'-OH), deoxyribonucleotides (2'-deoxy), 2'-F, and 2'-OMe nucleotides. Additionally modified oligonucleotides may contain nucleotides bearing more than one modification simultaneously such as a modification at the internucleotide linkage (e.g. phosphorothioate) and at the sugar (e.g. 2'-OMe) and the base (e.g. inosine). In another embodiment the nucleotide bearing more than one modification simultaneously comprises for example a 2'-OMe modification and a side chain modification at a position on its nucleo base.

Transcription Conditions

A number of factors have been determined to be important for the transcription conditions of the 2'-modified SELEX™ method. The factors described for transcription conditions with transcription mixtures comprising 2' modified, particularly 2'-OMe modified nucleotides, are also used in connection with transcription methods of the present invention with transcription mixtures comprising 2' modified and side chain nucleobase modified nucleotide triphosphates. Side chain modified nucleotide triphosphates for use in the present invention have been described. See, for example Vaught J D, Dewey T, Eaton B E. J Am Chem. Soc. 2004; 126:11231-11237; Nieuwlandt D, West M, Cheng X, Kirshenheuter G, Eaton B E. Chembiochem. 2003, 4, 651-654; Ito T, Ueno Y, Komatsu Y, Matsuda A. Nucleic Acids Res. 2003; 31, 2514-2523; Dewey, T M, Mundt, A A, Crouch, G J, Zyzniewyski, M C, Eaton, B E. J Am Chem Soc 1995, 117, 8474-8475; Jager S, Rasched G, Kornreich-Leshem H, Engeser M, Thum O, Famulok M. J Am Chem. Soc. 2005, 127, 15071-15082; Tarasow T M, Tarasow S L, Eaton B E. Nature. 1997, 389, 54-57; Liu D, Gugliotti L A, Wu T, Dolska M, Tkachenko A G, Shipton M K, Eaton B E, Feldheim D L. Langmuir. 2006, 22, 5862-5866; Gugliotti L A, Feldheim D L, Eaton B E. J Am Chem. Soc. 2005, 127, 17814-17818; Gugliotti L A, Feldheim D L, Eaton B E. Science. 2004, 304, 850-852; Kuwahara M, Hanawa K, Ohsawa K, Kitagata R, Ozaki H, Sawai H. Bioorg Med. Chem. 2006, 14, 2518-2526; Saitoh H, Nakamura A, Kuwahara M, Ozaki H, Sawai H. Nucleic Acids Res Suppl. 2002, 2, 215-216; Kuwahara M, Ohbayashi T, Hanawa K, Shoji A, Ozaki A N, Ozaki H, Sawai H. Nucleic Acids Res Suppl. 2002, 2, 83-84. Mehedi Masud M, Ozaki-Nakamura A, Kuwahara M, Ozaki H, Sawai H Chembiochem. 2003, 4, 584-548; Masud M M, Ozaki-Nakamura A, Satou F, Ohbayashi T, Ozaki H, Sawai H. Nucleic Acids Res Suppl. 2001; (1):21-2; Obayashi T, Masud M M, Ozaki A N, Ozaki H, Kuwahara M, Sawai H. Bioorg Med Chem. Lett. 2002, 12, 1167-70; Sawai H, Ozaki-Nakamura A, Mine M, Ozaki H. Bioconjug Chem. 2002, 2, 309-316; Ohbayashi T, Kuwahara M, Hasegawa M, Kasamatsu T, Tamura T, Sawai H Org Biomol Chem. 2005, 3, 2463-2468; Shoji A, Hasegawa T, Kuwahara M, Ozaki H, Sawai H. Bioorg Med Chem. Lett. 2006 Oct. 28; [Epub ahead of print] Kuwahara M, Nagashima J, Hasegawa M, Tamura T, Kitagata R, Hanawa K, Hososhima S, Kasamatsu T, Ozaki H, Sawai H. Nucleic Acids Res. 2006, 34, 5383-5394; Ito Y. Nucleic Acids Symp Ser. 997, 37, 259-260; Schoetzau T, Langner J, Moyroud E, Roehl I, Vonhoff S, Klussmann S. Bioconjug Chem. 2003, 5, 919-926; Mehedi Masud M, Ozaki-Nakamura A, Kuwahara M, Ozaki H, Sawai H. Chembiochem. 2003, 4, 584-588; and Ebara Y, Kaihatsu K, Ueji S. Nucleic Acids Symp Ser. 1999, 42, 175-176 each of which is incorporated herein by reference in its entirety.

For example, increases in the yields of modified transcript may be observed under some conditions when a particular leader sequence/mutant polymerase combination is used. A leader sequence is a sequence that can be incorporated into the 3' end of a fixed sequence at the 5' end of the DNA transcription template. The leader sequence is typically 6-15 nucleotides long, and may be composed of a predetermined nucleotide composition, for example it may be all purines, or a particular mixture of purine and pyrimidine nucleotides.

Examples of templates that may be used with the mutant polymerases and transcription conditions of the invention, particularly in combination with Y639L/H784A, Y639L/H784A/K378R, P266L/Y639L/H784A or P266L/Y639L/H784A/K378R, are ARC2118 (SEQ ID NO 7), ARC2119 (SEQ ID NO 31), and as indicated in the examples below. A leader sequence in the templates used with these mutant polymerases is optional.

In addition, the presence of 2'-OH GTP has historically been an important factor in obtaining transcripts incorporating modified nucleotides. Transcription can be divided into two phases: the first phase is initiation, during which an NTP is added to the 3'-end of GTP (or another substituted guanosine) to yield a dinucleotide which is then extended by about 10-12 nucleotides; the second phase is elongation, during which transcription proceeds beyond the addition of the first about 10-12 nucleotides. It was previously found that small amounts of 2'-OH GTP added to a transcription mixture containing Y639F/K378R mutant or Y639F/H784A/K378R mutant T7 RNA polymerase and an excess of 2'-OMe GTP was sufficient to enable the polymerase to initiate transcription using 2'-OH GTP (and gave a higher yield of 2'-OMe containing transcript than without 2'-OH GTP), but once transcription enters the elongation phase the reduced discrimination between 2'-OMe and 2'-OH GTP, and the excess of 2'-OMe GTP over 2'-OH GTP allows the incorporation of principally the 2'-OMe GTP.

The present invention provides mutant T7 RNA polymerases, e.g. Y639L/H784A, Y639L/H784A/K378R, P266L/Y639L/H784A or P266L/Y639L/H784A/K378R which do not require 2'-OH GTP in the transcription mixture for a high yield of 2'-OMe transcription resulting in transcripts in which GTP, except for the starting nucleotide, is 2'-OMe. In one embodiment, the high yield is on average at least one transcript per input transcription template.

Another factor in the incorporation of 2'-OMe substituted nucleotides into transcripts is the use of both divalent magnesium and manganese ($Mn^{2+}$) in the transcription mixture. Different combinations of concentrations of magnesium chloride and manganese chloride have been found to affect yields of 2'-O-methylated transcripts, the best concentration of the magnesium and manganese chloride being dependent on the concentration in the transcription reaction mixture of NTPs which complex divalent metal ions. To obtain the greatest yields of all 2'-O-methylated transcripts (i.e., all 2'-OMe ATP, 2'-OMe UTP, 2'-OMe CTP, and 2'-OMe GTP nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When each NTP is present at a concentration of 1.5 mM, concentrations of approximately 8 mM magnesium chloride and 3.0 mM manganese chloride are preferred. When the concentration of each NTP is 2.0 mM, concentrations of approximately 9.5 mM magnesium chloride and 3.0 mM manganese chloride are preferred. In any case, departures from these concentrations of up to two-fold still give significant amounts of modified transcripts.

Priming transcription with 2'-OH GMP, guanosine, or other 2'-OH guanosines substituted at a position other than the 2'-OH sugar position is also important for transcription mixtures which do not contain 2'-OH GTP. This effect results from the specificity of the polymerase for the initiating nucleotide. As a result, the 5'-terminal nucleotide of any transcript generated in this fashion is likely to be 2'-OH guanosine (2'-OH G). A preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), 2'-OMe UTP (100%). 2'-OMe CTP (100%) and 2'-OMe GTP (100%) ("MNA") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 3.0 mM, 2'-OMe NTP (each) 1.5 mM, 2'-OH GMP 1 mM, pH 7.5, Y639L/H784A/K378R mutant T7 RNA Polymerase 200 nM, inorganic pyrophosphatase 0.025 units/ml, and a DNA template. In some embodiments, the DNA template may be present in a concentration of preferably about 5 to 500 nM.

For maximum incorporation of 2'-OMe ATP (100%), 2'-OMe UTP (100%) or 2'-OMe TTP (100%), 2'-OMe GTP (100%) and 2'-deoxy CTP (100%) ("dCmD") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 3.0 mM, 2'-OMe NTP (ATP, UTP or TTP, GTP) 1.5 mM, 2-deoxy CTP 1.5 mM, 2'-OH GMP 1 mM, pH 7.5, Y639L/H784A/K378R mutant T7 RNA Polymerase 200 nM, inorganic pyrophosphatase 0.025 units/ml, and a DNA template. In some embodiments, the DNA template may be present in a concentration of preferably about 5 to 500 nM.

For maximum incorporation of 2'-OMe ATP (100%), 2'-OMe CTP (100%), 2'-OMe GTP (100%) and 2'-deoxy TTP (100%) ("dTmV") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 2.5 mM, 2'-OMe NTP (ATP, CTP, GTP) 1.5 mM, 2-deoxy TTP 1.5 mM, 2'-OH GMP 1 mM, pH 7.5, Y639L/H784A/K378R mutant T7 RNA Polymerase 200 nM, inorganic pyrophosphatase 5 units/ml, and a DNA template. In some embodiments, the DNA template may be present in a concentration of preferably about 5 to 500 nM.

For maximum incorporation of 2'-OMe ATP (100%), 2'-OMe CTP (100%), 2'-OMe GTP (100%) and 2'-deoxy UTP (100%) ("dUmV") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 3.0 mM, 2'-OMe NTP (ATP, CTP, GTP) 1.5 mM, 2-deoxy UTP 1.5 mM, 2'-OH GMP 1 mM, pH 7.5, Y639L/H784A/K378R mutant T7 RNA Polymerase 200 nM, inorganic pyrophosphatase 0.025 units/ml, and a DNA template. In some embodiments, the DNA template may be present in a concentration of preferably about 5 to 500 nM.

For maximum incorporation of 2'-OMe ATP (100%), 2'-OMe CTP (100%), 2'-OMe GTP (100%) and 2'-OH UTP (100%) ("rUmV") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 3.0 mM, 2'-OMe NTP (ATP, CTP, GTP) 1.5 mM, 2'-OH UTP 1.5 mM, 2'-OH GMP 1 mM, pH 7.5, Y639L/H784A/K378R mutant T7 RNA Polymerase 200 nM, inorganic pyrophosphatase 0.025 units/ml, and a DNA template. In some embodiments, the DNA template may be present in a concentration of preferably about 5 to 500 nM.

Optionally, the DNA template used with the above transcription conditions comprises an all purine leader sequence that increases the transcription yield relative to a template that does not comprise such a leader sequence when both templates are transcribed under identical conditions. In another embodiment, the leader sequence is a mixture of purines and pyrimidines that increases the transcription yield relative to a template that does not comprise such a leader sequence when both are transcribed under identical conditions. As used herein, one unit of inorganic pyrophosphatase is defined as the amount of enzyme that will liberate 1.0 mole of inorganic orthophosphate per minute at pH 7.2 and 25° C. The reaction may be carried out from about 1 to 24 hours.

In each case, the transcription products can then be used for input into the SELEX™ process to identify aptamers and/or to determine a conserved sequence that has binding specificity to a given target. The resulting sequences are already stabilized, eliminating this step from the post-SELEX™ modification process and giving a more highly stabilized aptamer as a result.

As described below, useful yields of transcripts incorporating 2' substituted nucleotides can be obtained under conditions other than the conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5:1, more preferably, the ratio is about 3-4:1.

The 2'-OMe NTP concentration (each NTP) can range from 5 μM to 5 mM.

The deoxy NTP concentration (each NTP) can range from 5 μM to 5 mM.

The 2'-OH NTP concentration (each NTP) can range from 5 μM to 5 mM.

The 2'-OH GTP concentration (where 2'-OMe GTP ranges from 5 μM to 5 mM in the reaction mixture) can range from 0 μM to 300 μM. In a preferred embodiment, transcription occurs in the absence of 2'-OH GTP (0 μM).

The concentration of 2'-OH GMP, guanosine or other 2'-OH G substituted at a position other than the 2'-sugar position, can range from 0 to 5 mM. Where 2'-OH GTP is not included in the reaction 2'-OH GMP is required and may range from 5 μM to 5 mM.

The DNA template concentration can range from 5 nM to 5 μM.

The mutant polymerase concentration can range from 2 nM to 20 μM.

The inorganic pyrophosphatase can range from 0 to 100 units/ml.

The pH can range from pH 6 to pH 9. The methods of the present invention can be practiced within the pH range of activity of most polymerases that incorporate modified nucleotides.

The transcription reaction may be allowed to occur from about one hour to weeks, preferably from about 1 to about 100 hours.

In addition, the methods of the present invention provide for the optional use of chelating agents in the transcription reaction condition including, for example, EDTA, EGTA, and DTT.

Aptamer Medicinal Chemistry

Once aptamers that bind to a desired target are identified, several techniques may be optionally performed to further increase binding and/or functional characteristics of the identified aptamer sequences. Aptamers, e.g. MNA, dCmD, dTmV, rUmV, dUmV aptamers, that bind to a desired target identified through the SELEX™ process, (e.g. the 2'-Modified SELEX™ method) may be optionally truncated to obtain the minimal aptamer sequence (also referred to herein as "minimized construct") having the desired binding and/or functional characteristics. One method of accomplishing this is by using folding programs and sequence analysis (e.g., aligning clone sequences resulting from a selection to look for conserved motifs and/or covariation) to inform the design of minimized constructs. Biochemical probing experiments can also be performed to determine the 5' and 3' boundaries of an aptamer sequence to inform the design of minimized constructs. Minimized constructs can then be chemically synthesized and tested for binding and functional characteristics as compared to the non-minimized sequence from which they were derived. Variants of an aptamer sequence containing a series of 5', 3' and/or internal deletions may also be directly chemically synthesized and tested for binding and/or functional characteristics as compared to the non-minimized aptamer sequence from which they were derived.

Additionally, doped reselections may be used to explore the sequence requirements within a single active aptamer sequence such as an MNA, dCmD, dTmV, rUmV or dUmV aptamer (i.e., an aptamer that binds to a desired target identified through the SELEX™ process, (including 2'-Modified SELEX™ process), or a single minimized aptamer sequence. Doped reselections are carried out using a synthetic, degenerate pool that has been designed based on the single sequence of interest. The level of degeneracy usually varies 70% to 85% from the wild type nucleotide, i.e., the single sequence of interest. In general, sequences with neutral mutations are identified through the doped reselection process, but in some cases sequence changes can result in improvements in affinity. The composite sequence information from clones identified using doped reselections can then be used to identify the minimal binding motif and aid in Medicinal Chemistry efforts.

Aptamer sequences identified using the SELEX™ process such as MNA, dCmD, dTmV, rUmV or dUmV aptamers (including the 2'-Modified SELEX process and doped reselections) and/or minimized aptamer sequences may also be optionally modified post-SELEX™ selection using Aptamer Medicinal Chemistry to perform random or directed mutagenesis of the sequence to increase binding affinity and/or functional characteristics, or alternatively to determine which positions in the sequence are essential for binding activity and/or functional characteristics.

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry may be used particularly as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some As (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is certainly not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:

(1) Substituents already present in the body, e.g., 2'-deoxy, 2'-ribo, 2'-O-methyl purines or pyrimidines or 5-methyl cytosine.

(2) Substituents already part of an approved therapeutic, e.g., phosphorothioate-linked oligonucleotides.

(3) Substituents that hydrolyze or degrade to one of the above two categories, e.g., methylphosphonate-linked oligonucleotides.

The aptamers of the present invention include aptamers developed through aptamer medicinal chemistry as described herein.

Target binding affinity of the aptamers of the present invention can be assessed through a series of binding reactions between the aptamer and target (e.g., a protein) in which trace $^{32}P$-labeled aptamer is incubated with a dilution series of the target in a buffered medium then analyzed by nitrocellulose filtration using a vacuum filtration manifold. Referred to herein as the dot blot binding assay, this method uses a three layer filtration medium consisting (from top to bottom) of nitrocellulose, nylon filter, and gel blot paper. RNA that is bound to the target is captured on the nitrocellulose filter whereas the non-target bound RNA is captured on the nylon filter. The gel blot paper is included as a supporting medium for the other filters. Following filtration, the filter layers are separated, dried and exposed on a phosphor screen and quantified using a phosphorimaging system from which. The quantified results can be used to generate aptamer binding curves from which dissociation constants ($K_D$) can be calculated. In a preferred embodiment, the buffered medium used to perform the binding reactions is 1× Dulbecco's PBS (with $Ca^{++}$ and $Mg^{++}$) plus 0.1 mg/mL BSA.

Generally, the ability of an aptamer to modulate the functional activity of a target, i.e., the functional activity of the aptamer, can be assessed using in vitro and in vivo models, which will vary depending on the biological function of the target. In some embodiments, the aptamers of the present invention may inhibit a known biological function of the target, while in other embodiments the aptamers of the invention may stimulate a known biological function of the target. The functional activity of aptamers of the present invention can be assessed using in vitro and in vivo models designed to measure a known function of the aptamer target.

The aptamers of the present invention may be routinely adapted for diagnostic purposes according to any number of techniques employed by those skilled in the art. Diagnostic utilization may include both in vivo or in vitro diagnostic applications. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any aptamer by procedures known in the art to incorporate a labeling tag in order to track the presence of such ligand. Such a tag could be used in a number of diagnostic procedures.

Aptamers Having Immunostimulatory Motifs

Recognition of bacterial DNA by the vertebrate immune system is based on the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 binds unmethylated oligodeoxynucleotide ("ODN") CpG sequences in a sequence-specific manner. The recognition of CpG motifs triggers defense mechanisms leading to innate and ultimately acquired immune responses. For example, activation of TLR 9 in mice induces activation of antigen presenting cells, up regulation of MHC class I and II molecules and expression of important co-stimulatory molecules and cytokines including IL-12 and IL-23. This activation both directly and indirectly enhances B and T cell responses, including robust up regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODNs can provide protection against infectious diseases, function as immuno-adjuvants or cancer therapeutics (monotherapy or in combination with a mAb or other therapies), and can decrease asthma and allergic response.

Aptamers of the present invention, e.g. MNA, dCmD, dTmV, rUmV or dUmV aptamers, may comprise one or more CpG or other immunostimulatory sequence. Such aptamers can be identified or generated by a variety of strategies using, e.g., the SELEX™ process described herein. In general the strategies can be divided into two groups. In group one, the strategies are directed to identifying or generating aptamers comprising both a CpG motif or other immunostimulatory sequence as well as a binding site for a target, where the target (hereinafter "non-CpG target") is a target other than one known to recognize CpG motifs or other immunostimulatory sequences and known to stimulates an immune response upon binding to a CpG motif The first strategy of this group comprises performing SELEX™ to obtain an aptamer to a specific non-CpG target, using an oligonucleotide pool wherein a CpG motif has been incorporated into each member of the pool as, or as part of, a fixed region, e.g., in some embodiments the randomized region of the pool members comprises a fixed region having a CpG motif incorporated therein, and identifying an aptamer comprising a CpG motif. The second strategy of this group comprises performing SELEX™ to obtain an aptamer to a specific non-CpG target preferably a target and following selection appending a CpG motif to the 5' and/or 3' end or engineering a CpG motif into a region, preferably a non-essential region, of the aptamer. The third strategy of this group comprises performing SELEX™ to obtain an aptamer to a specific non-CpG target, wherein during synthesis of the pool the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a specific non- CpG target, and identifying an aptamer comprising a CpG motif. The fifth strategy of this group comprises performing SELEX™ to obtain an aptamer to a specific non-CpG target and identifying an aptamer which, upon binding, stimulates an immune response but which does not comprise a CpG motif.

In group two, the strategies are directed to identifying or generating aptamers comprising a CpG motif and/or other sequences that are bound by the receptors for the CpG motifs (e.g., TLR9 or the other toll-like receptors) and upon binding stimulate an immune response. The first strategy of this group comprises performing SELEX™ to obtain an aptamer to a target known to bind to CpG motifs or other immunostimulatory sequences and upon binding stimulate an immune response using an oligonucleotide pool wherein a CpG motif has been incorporated into each member of the pool as, or as part of, a fixed region, e.g., in some embodiments the randomized region of the pool members comprise a fixed region having a CpG motif incorporated therein, and identifying an aptamer comprising a CpG motif. The second strategy of this group comprises performing SELEX™ to obtain an aptamer to a target known to bind to CpG motifs or other immunostimulatory sequences and upon binding stimulate an immune response and then appending a CpG motif to the 5' and/or 3' end or engineering a CpG motif into a region, preferably a non-essential region, of the aptamer. The third strategy of this group comprises performing SELEX™ to obtain an aptamer to a target known to bind to CpG motifs or other immunostimulatory sequences and upon binding stimulate an immune response wherein during synthesis of the pool, the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a target known to bind to CpG motifs or other immunostimulatory sequences and upon binding stimulate an immune response and identifying an aptamer comprising a CpG motif. The fifth strategy of this group comprises performing SELEX™ to obtain an aptamer to a target known to bind to CpG motifs or other immunostimulatory sequences, and identifying an aptamer which upon binding, stimulate an immune response but which does not comprise a CpG motif.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu. Rev. Immunol. 2002, 20:709-760, incorporated herein by reference. Additional immunostimulatory motifs are disclosed in the following U.S. patents, each of which is incorporated herein by reference: U.S. Pat. No. 6,207,646; U.S. Pat. No. 6,239,116; U.S. Pat. No. 6,429,199; U.S. Pat. No. 6,214,806; U.S. Pat. No. 6,653,292; U.S. Pat. No. 6,426,434; U.S. Pat. No. 6,514,948 and U.S. Pat. No. 6,498,148. Any of these CpG or other immunostimulatory motifs can be incorporated into an aptamer. The choice of aptamers is dependent on the disease or disorder to be treated. Preferred immunostimulatory motifs are as follows (shown 5' to 3' left to right) wherein "r" designates a purine, "y" designates a pyrimidine, and "X" designates any nucleotide: AACGTTCGAG (SEQ ID NO:8); AACGTT; ACGT, rCGy; rrCGyy, XCGX, XXCGXX, and $X_1X_2CGY_1Y_2$ wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs and upon binding stimulate an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used so long as the ability of the aptamer to bind to the non-CpG target is not significantly interfered with.

As used herein, "stimulation of an immune response" can mean either (1) the induction of a specific response (e.g., induction of a Th1 response) or of the production of certain molecules or (2) the inhibition or suppression of a specific response (e.g., inhibition or suppression of the Th2 response) or of certain molecules.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in the provisional application U.S. Ser. No. 60/550,790, filed on Mar. 5, 2004, and entitled "Controlled Modulation of the Pharmacokinetics and Biodistribution of Aptamer Therapeutics", and in the non-provisional application U.S. Ser. No. 11/075,648, filed on Mar. 7, 2005, and entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (C1), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (C1) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions, e.g. MNA, dCmD, dTmV, rUmV or dUmV aptamers, in vivo by conjugating an aptamer, e.g. an MNA, dCmD, dTmV, rUmV or dUmV aptamer, to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272 (25): 16010-7)), Ant (a 16-amino acid sequence derived from the third helix of the *Drosophila antennapedia* homeotic protein (Pietersz, et al. (2001), Vaccine 19 (11-12): 1397-405)) and $Arg_7$ (a short, positively charged cell-permeating peptides composed of polyarginine ($Arg_7$) (Rothbard, et al. (2000), Nat. Med. 6 (11): 1253-7; Rothbard, J et al. (2002), J. Med. Chem. 45 (17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2'F and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

PEG-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used in the invention include polyethylene glycol ("PEG"), also known as polyethylene oxide ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: $HO—CH_2CH_2O—(CH_2CH_2O)_n—CH_2CH_2—OH$. This polymer, alpha-, omega-dihydroxylpolyethylene glycol, can also be represented as HO-PEG-OH, where it is understood that the -PEG-symbol represents the following structural unit: $—CH_2CH_2O—(CH_2CH_2O)_n—CH_2CH_2—$ where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively non-reactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, —$OCH_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.,* 60:331-336 (1995). PAG conjugates are often used not only to enhance solubility and stability but also to prolong the blood circulation half-life of molecules.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched. In some embodiments the polymers are PEG.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid)$_n$ where n is greater than or equal to 1.

High molecular weight compositions of the invention include those having a molecular weight of at least 10 kDa. Compositions typically have a molecular weight between 10 and 80 kDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid- PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM $NaHCO_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

PAG-Derivatization of a Reactive Nucleic Acid

Figure 2:
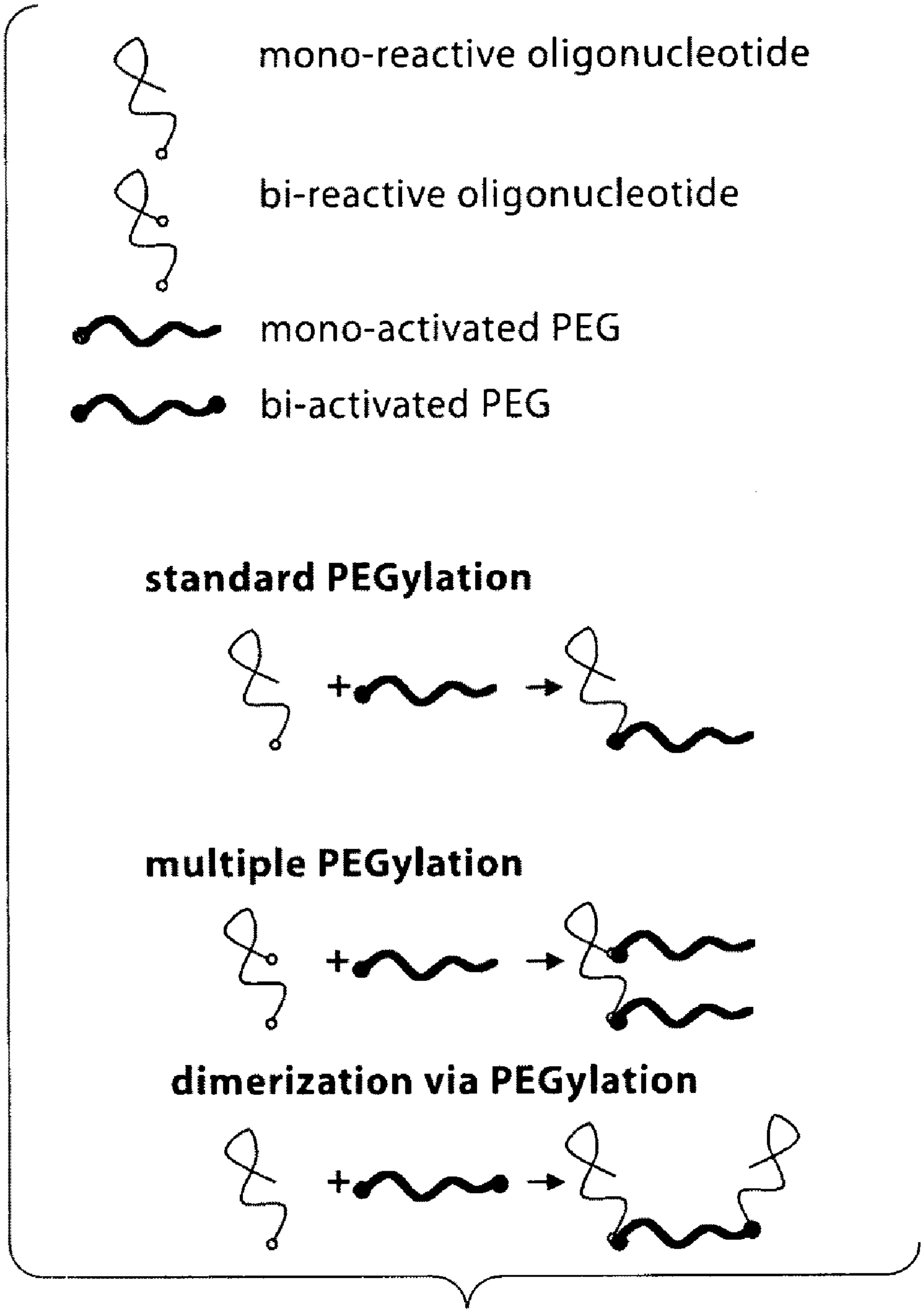
FIG. 2 is an illustration depicting various PEGylation strategies representing standard mono-PEGylation, multiple PEGylation, and dimerization via PEGylation.

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 2. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully, partially, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with the target will preclude the formation of complex between aptamer and the target. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Polymerase Expression and Purification

Mutant T7 RNA polymerase, for use in the methods of the invention may be prepared as follows. T7 RNA polymerase (nucleic acid and amino acid sequence shown in FIGS. 3A and 3B respectively and described in Bull, J. J et al., *J. Mol. Evol.,* 57 (3), 241-248 (2003) may be mutated to result in the LA mutant (Y639L/H784A), the LAR mutant (Y639L/H784A/K378R), the LLA mutant (P266L/Y639L/H784A) or the LLAR mutant P266L/Y639L/H784A/K378R). T7 RNA polymerase may be comprised in an expression vector (an example of a T7 RNA polymerase expression vector is described in U.S. Pat. No. 5,869,320 herein incorporated by reference in its entirety) or may be inserted into an expression vector following mutagenesis. The mutated T7 RNA polymerase may be engineered to optionally comprise a His-tag for ease during protein purification.

Complementary oligonucleotide sequences that contain the Leucine mutation for position 639 (agtcatgacgctggctCTGgggtccaaagagttcg (SEQ ID NO 9) and gaactctttggacccCAGagccagcgtcatgact (SEQ ID NO 10) may be synthesized. Complementary oligonucleotide sequences (ggctggcatctctcTgatgttccaaccttgc (SEQ ID NO 11) and gcaaggttggaacatcAgagagatgccagcc (SEQ ID NO 12) for P266L mutation may be synthesized. Complementary oligonucleotide sequences (cgctcctaactttgtaGCcagccaagacggtagc (SEQ ID NO 13) and gctaccgtcttggctgGCtacaaagttaggagcg (SEQ ID NO 14)) for H784A mutation may be synthesized. Complementary oligonucleotide sequences (gctctcaccgcgtggaGacgtgctgccgctgct (SEQ ID NO 15) and agcagcggcagcacgtCtccacgcggtgagagc (SEQ ID NO 16) for K378R mutation may be synthesized. Site-directed mutagenesis may be performed using QuikChange® Site-Directed Mutagenesis Kit (Stratagene, La Jolla, Calif.) according to the manufacturer's instructions to result in nucleic acid sequences (FIG. 4) encoding mutant polymerases having the above indicated combination of mutations. The resulting nucleic acid sequence encoding a mutant polymerase of the invention may be inserted into the desired expression vector using standard techniques for expression and purification.

Expression and Purification

The expression vector comprising the mutant T7 polymerase nucleic acid sequence is transformed into BL21 (DE3) competent cells (Stratagene, CA) and incubated on ice for 20 min. Heat shock is performed by putting the tube in 42° C. for 2 min. After putting the tube on ice for 1 minute, 1 ml L broth ("LB") is added and incubated in 37° C. shaker for 45 min. 100 ul of culture liquid is plated on LB+Amp agar plate and incubated at 37° C. overnight.

A single colony from the overnight cultured plate is inoculated into 100 ml LB-Amp+ (150 ug/ml), 37° C. overnight. On the second day, two 4-liter flasks containing 2 liters of pre-warmed LB+Amp are inoculated with 50 ml of overnight culture and grown at 37° C. until OD600 reaches between 0.6-0.8. 200 ul of 1M IPTG is added to each 2 L cell culture with final concentration of 100 uM and grow for another 3 hrs at 37° C. The cells are pelleted by spinning at 5000 rpm for 10 min. Cells are resuspended in 200 ml lysis buffer (Lysis buffer: 50 mM Tris-Cl, pH 8.0, 100 mM NaCl, 5% Glycerol, 1 mM imidazole, betamercaptoethanol ("BME") 5 mM) and divided into 6 conical 50 ml tubes. The cells are sonicated at power level 8, 3×30" for each tube and then bacterial debris is spun down at 11,000 rpm for 60 min and the supernatant filtered through 0.22 uM filter. Imidazole is added to the filtrate to a final concentration of 10 mM.

The filtrate is loaded onto a 5 ml Ni-NTA column (GE Healthcare Bio-Sciences, NJ) with sample pump. The column is washed with 10 column volumes (CV) of buffer A (Buffer A: 50 mM Tris-Cl, pH 8.0, 100 mM NaCl, 5% Glycerol, 10 mM imidazole, BME 10 mM) containing 20 mM imidazole. The column is then washed with 10 CV of buffer with a linear gradient of imidazole concentration from 40 mM to 70 mM in buffer A. The protein is eluted with 6 CV of Buffer B (Buffer B: 50 mM Tris-C1, pH 8.0, 100 mM NaCl, 5% Glycerol, 250 mM imidazole, BME10 mM). After checking the collection fractions with 5 μl of sample on 4-12% SDS-PAGE, all the fractions of interest are combined and dialyzed (dialysis tubing: Spectrum Spectra/por Molecular porous membrane (VWR) MWCO:12-14000) in 1 L of dialysis buffer (Dialysis buffer: 50 mM Tris-Cl, pH 7.9, 100 mM NaCl, 50% Glycerol, 0.1 mM EDTA, 0.1% Triton X-100, BME 20 mM) overnight. The dialysis buffer is changed after 12 hours and dialysis is carried out for an additional 4 hours. The concentration of T7 RNA polymerase is measured using the Bradford assay as described in Bradford, M. M. (1976) *Anal. Biochem.* 72, 248.

Example 2

Transcription Incorporating 100% 2'-O-Methyl Nucleotides

Example 2A

2'-O-Methyl Transcription without 2'-OH GTP

An experiment was performed to test the sensitivity of Y639L/H784A/K378R mutant polymerase to the concentration of 2'-OH GTP by using a titration of 2'-OH GTP.

ARC2118 and ARC2119, two libraries which showed high transcript yields when used with the Y639L/H784A/K378R mutant T7 RNA polymerase, were used to test the sensitivity of transcription of the Y639L/H784A/K378R mutant T7 RNA polymerase to the concentration of 2'-OH GTP. The sequence of ARC2118 is given in Example 2C below and that of ARC2119 is given immediately below in the 5' to 3' direction.

```
ARC2119
                                          (SEQ ID NO 31)
TAATACGACTCACTATAGGGGGTGATATTGACGTTCTCGNNNNNNNNNNN

NNNNNNNNNNNNNNNNNNNNNGGATCGTTACGACTAGCATCGATG
```

Transcriptions were performed using a titration of 2'-OH GTP (0-160 uM) with 1× transcription buffer (HEPES 200 mM, DTT 40 mM, spermidine 2 mM, Triton X-100 0.01% w/v). ~200 nM template, 2'-OMe ATP, CTP, UTP, and GTP 1 mM each, $MgCl_2$ 6.5 mM, $MnCl_2$ 2.0 mM, PEG-8000 w/v 10%, GMP 1 mM, inorganic pyrophosphatase 5 units/mL, Y639L/H784A/K378R mutant T7 RNA polymerase 200 nM, at 37° C. overnight.

Transcript yield under each condition was assayed by PAGE-gel analysis using 200 uL of reaction mixture, and transcript yield for each condition was quantitated from UV-shadowing of the PAGE-gel analysis using ImageQuant version 5.2 software (Molecular Dynamics). FIG. 5 summarizes the quantitated results of the PAGE-gel analysis, showing the fold-increase of transcript yield with of each condition relative to the background. As can be seen in FIG. 5, ARC2118 and ARC2119 transcribed with Y639L/H784A/K378R under all conditions, including no 2'-OH GTP, and the yield in the absence of 2'-OH GTP was comparable to transcription yield where 2'-OH GTP was included in the reaction mixture. These results indicate that the Y639L/H784A/K378R mutant T7 RNA polymerase does not require the presence of 2'-OH GTP for increased transcript yield, as opposed to the Y639F/H784A/K378R mutant T7 RNA polymerase, which requires 2'-OH GTP for transcription (data not shown).

An experiment was subsequently performed to determine the optimal transcription conditions to be used with the Y639L/H784A/K378R mutant T7 RNA polymerase. ARC2119, was used with the Y639L/H784A/K378R mutant T7 RNA polymerase to test the effect of varying the 2'-OMe NTP, magnesium and manganese concentrations on transcript yield.

Transcriptions were performed using lx transcription buffer (HEPES 200 mM, DTT 40 mM, spermidine 2 mM, Triton X-100 0.01%), ~200 nM template, 2'-OMe ATP, CTP, UTP, and GTP (0.5 mM, 1 mM, 1.5 mM, and 2 mM each), $MgCl_2$ (5 mM, 6.5 mM, 8 mM, and 9.5 mM), $MnCl_2$ (1.5 mM, 2 mM, 2.5 mM, 3 mM), PEG-8000 w/v 10%, GMP 1 mM, inorganic pyrophosphatase 5 units/mL, Y639L/H784A/K378R mutant T7 RNA polymerase 200 nM, at 37° C. overnight.

Transcript yield under each condition was assayed by PAGE-gel analysis using 200 uL of reaction mixture, and transcript yield for each condition was quantitated from UV-shadowing of the PAGE-gel analysis using ImageQuant version 5.2 software (Molecular Dynamics). FIG. 6 summarizes the quantitated results of the PAGE-gel analysis, showing the fold-increase of transcript yield with of each condition relative to background. Based on the cost of 2'-OMe NTPs, and the results of this experiment, 1.5 mM each 2'-OMe NTP (and 8 mM $MgCl_2$, 2.5 mM $MnCl_2$) was adopted as the preferred conditions for ARC2119 and the Y639L/H784A/K378R mutant T7 RNA polymerase of the present invention.

Example 2B

Fidelity and Bias of MNA Transcription Using Y639L/H784A/K378R Mutant T7 RNA Polymerase Additional experiments were performed to assess the fidelity and bias of MNA transcription using the Y639L/H784A/K378R mutant T7 RNA polymerase and no 2'-OH GTP. To test fidelity, a single cloned sequence was amplified by PCR, used to program a MNA transcription using the Y639L/H784A/K378R polymerase and no 2'-OH GTP, purified by PAGE, remaining DNA template was digested using RQ1 DNase (the absence of DNA template was then assayed by PCR) and the transcribed material was reverse-transcribed (Thermoscript, Invitrogen, Carlsbad, Calif.) and then amplified by PCR. This PCR product was sequenced and the statistics of deletions, insertions and substitutions was then calculated. Of the 1300 bases sequenced in this experiment, no deletions and insertions were observed, and three substitutions were observed (see FIG. 7). These numbers suggest that the sequence information encoded within a 30-nucleotide degenerate region would have a 93% chance of being faithfully transmitted to the next round of SELEX™, this number is so high that it exceeds that measured for wild-type RNA.

To test for nucleotide bias, library ARC2118 was transcribed under the following conditions: HEPES 200 mM, DTT 40 mM, spermidine 2 mM, Triton X-100 0.01% w/v, ~200 nM template, 2'-OMe ATP, CTP, UTP, and GTP 1 mM each (no 2'-OH GTP), $MgCl_2$ (6.5 mM), $MnCl_2$ (2 mM), PEG-8000 w/v 10%, GMP 1 mM, inorganic pyrophosphatase 5 units/mL, Y639L/H784A/K378R mutant T7 RNA polymerase 200 nM, at 37° C. overnight, purified by PAGE, the remaining DNA template was digested using RQ1 DNase (the absence of DNA template was then assayed by PCR) and the transcribed material was reverse-transcribed and amplified using PCR before cloning and sequencing. 48 clones from the amplified library and 48 clones from the starting library were sequenced. The statistics of nucleotide occurrence in the degenerate region were examined to see if bias occurred. As indicated by FIG. 8, the percentage of nucleotide composition after transcription was very similar to the percentage of nucleotide composition of the starting library in which the percentage of each nucleotide. (A, T, C and G) was approximately equal, indicating that no nucleotide bias occurs with the Y639L/H784A/K378R mutant T7 RNA polymerase is used for transcription.

Example 2C

MNA Transcription Using P266L/Y639L/H784A/K378R Mutant T7 RNA Polymerase

The following DNA template and primers were used to program a polymerase chain reaction to generate a double-stranded transcription template. N indicates a degenerate position with an approximately equal probability of being each of ATGC, all sequences are listed in the 5' to 3' direction:
PCR Template (ARC2118)

```
                                            (SEQ ID NO 7)
TAATACGACTCACTATAGGGGAGTACAATAACGTTCTCGNNNNNNNNNNNN
NNNNNNNNNNNNNNNNNNNGGATCGTTACGACTAGCATCGATG

5'-primer
                                            (SEQ ID NO 17)
AAAAAAAAAAAAAAAAAAAAAAAAAATAATACGACTCACTATAGGGGAG
TACAATAACGTTCTCG

3'-primer
                                            (SEQ ID NO 18)
CATCGATGCTAGTCGTAACG
```

The resultant double-stranded transcription template was then used to program 200 uL transcription mixtures for each sample as follows: HEPES (200 mM), DTT (40 mM), Spermidine (2 mM), Triton X-100 (0.01% w/v), $MgCl_2$ (8 mM), $MnCl_2$ (2.5 mM), PEG-8000 (10% w/v), 1.5 mM each of 2'-OMe NTP, GMP 1 mM, 100-200 nM transcription template, Inorganic Pyrophosphatase (1 unit), pH 7.5, the T7 mutant polymerase P266L/Y639L/H784A/K378R was diluted as indicated below. The transcription mixture was incubated at 37° C. overnight (16 h).

After incubation, the mixtures were precipitated with isopropanol, the resultant pellet was dissolved and quantitated using denaturing PAGE (12.5% acrylamide) for 60 min at 25 W. The samples were visualized and quantitated by UV shadow at 260 nm. Transcriptional yield is given in Table 1 below.

TABLE 1

Transcriptional Yield

| Enzyme | Enzyme Concentration | Normalized MNA Transcript Yield |
| --- | --- | --- |
| K378R/Y639L/H784A | 2.1 µg/ml | 100 |
| P266L/K378R/Y639L/H784A | 11 µg/ml | 130 |
| P266L/K378R/Y639L/H784A | 2.6 µg/ml | 65 |
| P266L/K378R/Y639L/H784A | 0.66 µg/ml | 13 |
| P266L/K378R/Y639L/H784A | 0.16 µg/ml | 8.3 |

Example 3

Transcription Incorporating 2'-O-Methyl ATP, GTP, and UTP Nucleotides and 2'-Deoxy CTP Nucleotides An experiment was performed to test the ability of Y639L/H784A/K378R mutant polymerase to incorporate both 2'-O-methyl nucleotides and 2'-deoxy nucleotides using in vitro transcription.

DNA templates ARC4206 and ARC4212 and their respective primers (sequences given in 5' to 3' direction below), were used to test the ability of transcription of the Y639L/H784A/K378R mutant T7 RNA polymerase to incorporate one 2'-deoxy CTP nucleotide with the other 3 nucleotides being 2'-O-methyl ATP, GTP, and UTP. Transcriptions were done using 200 mM HEPES, 40 mM DTT, 2.0 mM spermidine, 0.01% w/v TritonX-100, 10% PEG-8000, 8 mM $MgCl_2$, 2.5 mM $MnCl_2$, 1.5 mM dCTP, 1.5 mM mUTP, 1.5 mM mGTP, 1.5 mM mATP, 1 mM GMP, 0.01 units/µL inorganic pyrophosphatase, and ~9 µg/mL mutant T7 polymerase (Y639L/H784A/K378R) and 0.3 µM template DNA at 37° C. overnight to generate the ARC4206 and ARC4212 pools consisting of 2'-OMe ATP, GTP, and UTP nucleotides and 2'-deoxy CTP nucleotide (hereinafter "dCmD"). In parallel, transcriptions were done using 50 mM HEPES, 10 mM DTT, 0.5 mM spermidine, 0.0025% TritonX-100, 10% PEG-8000, 8 mM $MgCl_2$, 2.5 mM $MnCl_2$, 1.5 mM mCTP, 1.5 mM mUTP, 1.5 mM mGTP, 1.5 mM mATP, 1 mM GMP, 0.01 units/µL inorganic pyrophosphatase, and ~9 µg/mL mutant T7 polymerase (Y639L/H784A/K378R) and 0.3 µM template DNA at 37° C. overnight to generate the ARC4206 and ARC4212 pools consisting of 2'-OMe purine and pyrimidine nucleotides (hereinafter "MNA"). Transcript yield under each set of conditions was assayed by PAGE-gel analysis using 400 uL of reaction mixture, and transcript yield for each condition was visualized from UV-shadowing of the PAGE-gel. Table 2 summarizes the quantified results of the transcription yields, based on pool isolated after elution from the PAGE-gel in 300 mM NaOAc, 20 mM EDTA at 37° C. overnight, ethanol precipitation, followed by quantification by UV spectroscopy.

TABLE 2

| Transcriptional Yield | | |
|---|---|---|
| Pool | Yield (pmoles) | Yield (relative to MNA Pool) |
| ARC4206 MNA | 473 | |
| ARC4206 dCmD | 365 | 80% |
| ARC4212 MNA | 404 | |
| ARC4212 dCmD | 327 | 80% |

An additional experiment was performed to assess the fidelity of MNA and dCmD transcriptions using the Y639L/H784A/K378R mutant T7 RNA polymerase. To test fidelity, the ARC4206 and ARC4212 MNA and dCmD pools generated above were reverse-transcribed (Thermoscript, Invitrogen, Carlsbad, Calif.), amplified by PCR, and used to program an additional MNA and dCmD transcription using the Y639L/H784A/K378R polymerase. The pools were purified by PAGE, and the transcribed material was visualized from UV-shadowing of the PAGE-gel. Table 3 summarizes the quantified results of the transcription yields, based on pool isolated after elution from the PAGE-gel in 300 mM NaOAc, 20 mM EDTA for 4.5 hours at 65° C., ethanol precipitation, followed by quantification by UV spectroscopy.

TABLE 3

| Transcriptional Yield | | |
|---|---|---|
| Pool | Yield (pmoles) | Yield (relative to MNA Pool) |
| ARC4206 MNA | 367 | |
| ARC4206 dCmD | 145 | 40% |
| ARC4212 MNA | 402 | |
| ARC4212 dCmD | 182 | 45% |

```
ARC4206
                                        (SEQ ID NO 19)
GGGAGAATTCCGACCAGAAGCTTNNNNNNNNNNNNNNNNNNNNNNNNNNNNNN
NNNNNNNNNNNNNCATATGTGCGTCTACATGGATCCTCA

ARC4212
                                        (SEQ ID NO 20)
GGGAGAGACAAGCTTGGGTCNNNNNNNNNNNNNNNNNNNNNNNNNNNNNNNNN
NNNNNNNNNNAGAAGAGAAAGAGAAGTTAATTAAGGATCCTCAG
```

The templates were amplified with their respective DNA primers:

```
ARC4206
5' primer ARC4207
                                        (SEQ ID NO 21)
TAATACGACTCACTATAGGGAGAATTCCGACCAGAAGCTT

3' primer ARC4208
                                        (SEQ ID NO 22)
TGAGGATCCATGTAGACGCACATATG

ARC4212
5' primer ARC4213
                                        (SEQ ID NO 23)
TAATACGACTCACTATAGGGAGAGACAAGCTTGGGTC
```

-continued

```
3' primer ARC4214
                                        (SEQ ID NO 24)
CTGAGGATCCTTAATTAACTTCTCTTTCTCTTCT
```

Example 4

Aptamer Selection Using Y639L/H784A/K378R Mutant T7 RNA Polymerase

A selection was performed to identify aptamers to human Ang2 (hereinafter "h=Ang2") using a pool consisting of 2'-OMe purine and pyrimidine nucleotides (hereinafter "MNA"). The selection strategy yielded high affinity aptamers to specific for h-Ang2.

Human Ang2 was purchased from R&D Systems, Inc. (Minneapolis, Minn.). T7 RNA polymerase (Y639L/H784A/K378R) was expressed and purified as described in Example 1 above. 2'-OMe purine and pyrimidine nucleotides were purchased from TriLink BioTechnologies (San Diego, Calif.).

Selection of Ang2 Aptamer

Pool Preparation

A DNA template with the sequence 5'-TAATACGACTCACTATAGGGGAGTACAATAACGTTCTCGNNNNNNNNNNNNNNNNNNNNNNNNNNNNNNGGATCGTTACGACTAGCATCGATG ARC2118 (SEQ ID NO 7) was synthesized using an ABI EXPEDITE™ (Applied Biosystems, Foster City, Calif.) DNA synthesizer, and deprotected by standard methods. The templates were amplified with the primers (5'-(GATCGATCGATCGATCGATCTAATACGACTCACTATAGGGGAGTACAATAACGTTCTCG-3') (SEQ ID NO 26) and (5'-CATCGATGCTAGTCGTAACGATCC-3') (SEQ ID NO 27) and then used as a template for in vitro transcription with T7 RNA polymerase (Y639L/H784A/K378R). Transcriptions were done using 200 mM Hepes, 40 mM DTT, 2 mM spermidine, 0.01% w/v TritonX-100, 10% PEG-8000, 8 mM $MgCl_2$, 2.5 mM, $MnCl_2$, 1.5 mM mCTP, 1.5 mM mUTP, 1.5 mM mGTP, 1.5 mM mATP, 1 mM GMP, 0.01 units/μL inorganic pyrophosphatase, and ~9 μg/mL T7 polymerase (Y639L/H784A/K378R) and 0.5 μM template DNA to generate the ARC2118 mRmY pool.

Selection

The selection was initiated by incubating of 330 pmoles ($2\times10^{14}$ molecules) of MNA ARC 2118 pool with 100 pmoles of protein in a final volume of 100 μL selection buffer (1× Dulbecco's PBS (DPBS)) for 1 hr at room temperature. RNA-protein complexes and unbound RNA molecules were separated using a 0.45 micron nitrocellulose spin column (Schleicher and Schuell, Keene, N.H.). The column was pre-treated with KOH (Soak column filter in 1 mL 0.5M KOH, 15 min RT; spin through. Soak filter in 1 mL dH2O 5 min RT; spin through), washed 2×1 mL 1×PBS, and then the solution containing pool:Ang2 complexes was added to the column and centrifuged at 1500×g for 2 minutes. The filter was washed twice with 500 μL DPBS to remove non-specific binders. RNA was eluted by addition of 2×100 μL elution buffer (7 M urea, 100 mM sodium acetate, 3 mM EDTA, pre-heated to 95° C.) and then precipitated with ethanol. The RNA was reverse transcribed with the ThermoScript RT-PCR™ system (Invitrogen, Carlsbad, Calif.) according to the manufacturer's instructions using the primer SEQ ID NO 27. The cDNA was amplified by PCR with Taq polymerase (New England Biolabs, Beverly, Mass.) according to the manufacturer's instructions using SEQ ID NO 26 and SEQ ID NO 27. Templates were transcribed as described above for pool preparation and purified on a denaturing polyacrylamide gel.

Round 2 was performed with the same method as round 1. Rounds 3-12 were carried out with h-Ang2 immobilized on hydrophobic plates. Each round of selection was initiated by immobilizing 20 pmoles of h-Ang2 to the surface of a Nunc Maxisorp hydrophobic plate for 1 hour at room temperature in 100 μL of 1×DPBS. The plate was washed 5× with 120 μL DPBS then incubated with blocking buffer (1×DPBS, and 0.1 mg/mL BSA) for 1 hour. The supernatant was then removed and the wells were washed 5 times with 120 μL 1×DPBS. The pool RNA was incubated for 1 hour at room temperature in empty wells then for 1 hour in a well that had been previously blocked with 100 μL blocking buffer. From round 3 forward, the target-immobilized wells were blocked for 1 hour at room temperature in 100 μL blocking buffer (1×PBS, 0.1 mg/mL tRNA, 0.1 mg/mL ssDNA and 0.1 mg/mL BSA) before the positive selection step. In all cases, the pool RNA bound to immobilized h-Ang2 was reverse transcribed directly in the selection plate by the addition of reverse transcription ("RT") mix (3' primer, SEQ ID NO 27, and Thermoscript RT, Invitrogen, Carlsbad, Calif.) followed by incubation at 65° C. for 1 hour. The resulting cDNA was used as a template for PCR (Taq polymerase, New England Biolabs, Beverly, Mass.) and transcription as described for round 1. Conditions for each round are in Table 4.

TABLE 4

| Round Summary | | | | | | |
|---|---|---|---|---|---|---|
| Round | Pool (nM) | Platform | Negative | Buffer | Competitor | Target (nM) |
| 1 | 3300 | KOH filter | None | 1X DPBS | None | 1000 |
| 2 | 1000 | KOH filter | KOH filter | 1X DPBS | None | 1000 |
| 3 | 1000 | Plate | Plate; BSA plate | 1X DPBS | None | 200 |
| 4 | 1000 | Plate | Plate; BSA plate | 1X DPBS | None | 200 |
| 5 | 1000 | Plate | Plate; BSA plate | 1X DPBS | None | 200 |
| 6 | 1000 | Plate | Plate; BSA plate | 1X DPBS | None | 200 |
| 7 | 1000 | Plate | Plate; BSA plate | 1X DPBS | None | 200 |
| 8 | 1000 | Plate | Plate; BSA plate | 1X DPBS | None | 200 |
| 9 | 1000 | Plate | Plate; BSA plate | 1X DPBS | 0.1 mg/mL tRNA | 200 |
| 10 | 1000 | Plate | Plate; BSA plate | 1X DPBS | 0.1 mg/mL tRNA | 200 |
| 11 | 1000 | Plate | Plate; BSA plate | 1X DPBS | 0.1 mg/mL tRNA | 200 |
| 12 | 1000 | Plate | Plate; BSA plate | 1X DPBS | 0.1 mg/mL tRNA | 200 |

MNA Aptamer Binding Analysis

Dot blot binding assays were performed throughout the selections to monitor the protein binding affinity of the pools. Trace $^{32}$P-endlabeled pool RNA was combined with h-Ang2 and incubated at room temperature for 30 minutes in DPBS buffer in a final volume of 30 μL. The mixture was applied to a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-Ang2 binding was seen starting at round 9. Round 9, 10 and 12 pool templates were cloned using the TOPO TA cloning kit (Invitrogen, Carlsbad, Calif.) according to the manufacturer's instructions and 26 unique clones were chosen for chemical synthesis and dissociation constants ($K_D$) were determined. Briefly, the synthetic RNAs were 5' end labeled with γ-$^{32}$P ATP and $K_D$ values were determined using the dot blot assay and buffer conditions of 1×DPBS (w/ $Ca^{2+}$ and $Mg^{2+}$) (Gibco, Catalog #14040, Invitrogen, Carlsbad, Calif.). $K_D$s were estimated fitting the data to the equation: fraction RNA bound=amplitude*(((AptConc+[h-Ang2]+$K_D$)−SQRT((AptConc+[h-Ang2]+$K_D$)$^2$−4(AptConc*[h-Ang2])))/(2*AptConc))+background. Results are reported in Table 5 below.

Within the 26 unique sequences, 8 shared a similar motif and had similar binding and inhibitory activity. These sequences are identified as Family I. Family II comprises 2 sequences with a shared motif that had similar binding and inhibitory activities.

Analysis of MNA Aptamer Function

Elisa Assay

Some the aptamers were tested in an ELISA assay that was setup to measure their ability to interfere with Ang2 binding to the Tie2 receptor. To capture Tie2 receptor, 150 ng of Tie2-Fc (R&D systems 313-TI-100-CF, Minneapolis, Minn.) in 100 μL of PBS (pH 7.4) was put onto a 96-well Maxisorb plate (NUNC #446612, Rochester, N.Y.) and incubated overnight at 4° C. During the capture, 50 μL of various concentrations of synthetic RNA were mixed with 50 μL of 3.6 nM Ang2 (200 ng/mL) (R&D systems, 623-AN-025/CF, Minneapolis, Minn.) (in PBS with 0.2% BSA) with final Ang2 concentration at 1.8 nM (100 ng/mL) in PBS with 0.1% BSA and incubated at room temperature for 1 hour. The capture solution was removed after an overnight incubation and the plate was washed with 200 μL of TBST (25 mM Tris-HCl pH 7.5, 150 mM NaCl and 0.01% Tween 20) three times. The plate was then blocked with 200 μL TBST containing 5% nonfat dry milk for 30 minutes at room temperature. After blocking, the plate was washed with 200 μL of TBST again three times at room temperature and synthetic RNA:Ang2 mixture was added to the plate and incubated at room temperature for 1 hours. The plate was then washed with 200 μL of TBST three times and 100 μL of biotinylated goat anti- Ang2 antibody (1:1000; R&D Systems BAF623, Minneapolis, Minn.) was added and incubated for 1 hour at room temperature. After three washes with 200 μL of TBST, 100 μL of HRP linked Streptavidin (1:200; R&D systems #DY998, Minneapolis, Minn.) was added and incubated at room temperature for 0.5 hours. Then, the plate was washed again with 200 μL of TBST three times and 100 μL of TMP solution (Pierce, #34028) was added and incubated in the dark at room temp for 5 minutes. A solution of 1004 containing 2 N $H_2SO_4$ was added to stop the reaction and the plate was read by SpectroMax at 450 nm. The results are given in the final column of Table 5 below.

FACS Assay

Human umbilical vein endothelial cell ("HUVEC") (ATCC) and K293 cell, a cell line overexpressing human Tie2 receptor, were used to determine the $IC_{50}$ of specific MNA Ang2 aptamers that inhibit binding of Ang2 to Tie2 receptor on the cell membrane. In brief, recombinant mammalian expression vector pcDNA3.1-Tie2 was transfected into 293 cells (ATCC, Manassas, Va.) and stable clones were then obtained after selection with G418 (Invitrogen, Carlsbad, Calif.). Flow cytometry demonstrated expression of Tie2 protein on both HUVEC and K293 cells. An Ang2 titration assay further determined the amounts of Ang2 (R&D Systems, Minneapolis, Minn.) for aptamer inhibition assay on HUVEC and K293 cells which were 1 and 0.1 μg/mL, respectively.

In the flow cytometry binding assay, HUVEC and K293 cells ($2\times10^5$ cells/well) were pelleted in V bottomed 96-well plate and were subsequently resuspended and incubated in MNA aptamer/Ang2 solutions for 2 hours. Aptamer/Ang2 solutions were prepared by pre-incubation of different dosage of aptamers (100 nM, 33.3 nM, 11.1 nM, 3.7 nM, 1.2 nM, 0.411 nM, 0.137 nM, and 0.0456 nM) with Ang2 in FACs buffer (1% BSA, 0.2% sodium azide in PBS) for 30 min on ice. After three washes with FACs buffer, cells were incubated 30 minutes with biotinylated anti-human Ang2 antibody (5 μg/mL; R&D Systems, Minneapolis, Minn.), followed by another 30 minute incubation with Streptavidin PE (1:10; BD Biosciences, San Jose, Calif.). FACS analysis was completed using FACScan (BD Biosciences, San Jose, Calif.). The results are reported in Table 5 below.

TABLE 5

Summary of binding and functional results for anti-Ang2 MNA aptamers

| MNA Aptamer | Selection Round | Family | $K_D$ (nM) | $IC_{50}$ (293-Tie2 FACs) (nM) | $IC_{50}$ ELISA (nM) |
|---|---|---|---|---|---|
| 1 | 10 & 12 | I | 0.7 | 0.7 | Not tested |
| 2 | 10 & 12 | I | Not tested | 0.5 | Not tested |
| 3 | 12 | I | 0.2 | 0.5 | Not tested |
| 4 | 10 & 12 | I | 20.0 | 1.0 | Not tested |
| 5 | 12 | I | 34.0 | 0.7 | Not tested |
| 6 | 10 & 12 | I | 9.0 | 0.5 | 1.0 |
| 7 | 12 | I | 17.0 | 0.5 | 0.3 |
| 8 | 10 | II | 19.0 | 1.6 | 1.5 |
| 9 | 10 | I | 120.0 | Not tested | Not tested |
| 10 | 12 | I | 70.0 | Not tested | Not tested |
| 11 | 12 | I | No binding | Not tested | Not tested |
| 12 | 12 | I | 170.0 | Not tested | Not tested |
| 13 | 12 | I | 82.0 | Not tested | Not tested |
| 14 | 12 | I | No binding | Not tested | Not tested |
| 15 | 12 | I | No binding | Not tested | Not tested |
| 16 | 12 | I | No binding | No Inhibition | Not tested |
| 17 | 12 | I | 20.0 | No Inhibition | Not tested |
| 18 | 12 | I | 90.0 | Not tested | Not tested |
| 19 | 12 | II | 25.0 | 1.1 | 2.4 |
| 20 | 12 | I | No binding | No Inhibition | Not tested |
| 21 | 12 | I | 2.9 | 0.5 | Not tested |
| 22 | 12 | I | 17.0 | 0.6 | Not tested |
| 23 | 12 | I | No binding | Not tested | Not tested |
| 24 | 12 | I | No binding | Not tested | Not tested |
| 25 | 12 | I | No binding | No Inhibition | Not tested |
| 26 | 12 | I | No binding | Not tested | Not tested |

Example 5

Aptamer Selection Using Y639L/H784A/K378R Mutant T7 RNA Polymerase

A selection was performed to identify aptamers to human IgE (hereinafter "h-IgE") using a pool consisting of 2'-OMe purine and pyrimidine nucleotides (hereinafter "mRmY"). The selection strategy yielded high affinity aptamers specific for h-IgE.

Human IgE was purchased from Athens Research & Technology (Cat. #16-16-090705 Athens, Ga.). T7 RNA polymerase (Y639L/H784A/K378R) was expressed and purified as described in Example 1 above. 2'-OMe purine and pyrimidine nucleotides were purchased from TriLink BioTechnologies (San Diego, Calif.).

Selection of IgE Aptamer

Pool Preparation

A DNA template with the sequence 5'-TAATACGACTCACTATAGGGGAGTACAATAACGTTCTCGNNNNNNNNNNNNNNNNNNNNNNNNNNNNNNNNNGGATCGTTACGACTAGCATCGATG-3' ARC2118 (SEQ ID NO 7) was synthesized using an ABI EXPEDITE™ (Applied Biosystems, Foster City, Calif.) DNA synthesizer, and deprotected by standard methods. The templates were amplified with the primers (5'-(GATCGATCGATCGATCGATCTAATACGACTCACTATAGGGGAGTACAATAACGTTCTCG-3') (SEQ ID NO 26) and (5'-CATCGATGCTAGTCGTAACGATCC-3') (SEQ ID NO 27) and then used as a template for in vitro transcription with T7 RNA polymerase (Y639L/H784A/K378R). Transcriptions were done using 200 mM HEPES, 40 mM DTT, 2.0 mM spermidine, 0.01% w/v TritonX-100, 10% PEG-8000, 8 mM $MgCl_2$, 2.5 mM $MnCl_2$, 1.5 mM mCTP, 1.5 mM mUTP, 1.5 mM mGTP, 1.5 mM mATP, 1 mM GMP, 0.01 units/μL inorganic pyrophosphatase, and ~9 μg/mL mutant T7 polymerase (Y639L/H784A/K378R) and 0.3 μM template DNA to generate the ARC2118 MNA pool Selection The selection was initiated by incubating of 330 pmoles ($2\times10^{14}$ molecules) of MNA ARC 2118 pool with 24 pmoles of protein bound to a BSA-blocked hydrophobic plate (Maxisorp plate, Nunc, Rochester, N.Y.) in a final volume of 100 μL selection buffer (1× Dulbecco's PBS (DPBS) for 1 hr at room temperature. The well was washed four times with 120

μL DPBS to remove non-specific binders. RNA was eluted and reverse transcribed with the ThermoScript RT-PCR™ system (Invitrogen, Carlsbad, Calif.) according to the manufacturer's instructions using the primer SEQ ID NO 27. The cDNA was amplified by PCR with Taq polymerase (New England Biolabs, Beverly, Mass.) according to the manufacturer's instructions using SEQ ID NO 26 and SEQ ID NO 27. Templates were transcribed as described above for pool preparation and purified on a denaturing polyacrylamide gel.

All rounds were carried out with h-IgE immobilized on hydrophobic plates. Each round of selection was initiated by immobilizing 24 pmoles of h-IgE to the surface of a Nunc Maxisorp hydrophobic plate for 1 hour at room temperature in 100 μL of 1×DPBS. The plate was washed four times with 120 μL DPBS then incubated with blocking buffer (1×DPBS, and 0.1 mg/mL BSA) for 1 hour. The supernatant was then removed and the wells were washed four times with 120 μL 1×DPBS. Starting at Round 2, the pool RNA was incubated for 1 hour at room temperature in empty wells then for 1 hour in a well that had been previously blocked with 100 μL blocking buffer. From Round 2 forward, non-specific competitor was added to the positive selection step (0.1 mg/mL tRNA, and 0.1 mg/mL ssDNA). In all cases, the pool RNA bound to immobilized h-IgE was reverse transcribed directly in the selection plate by the addition of reverse transcription ("RT") mix (3' primer, SEQ ID NO 27, and Thermoscript RT, Invitrogen, Carlsbad, Calif.) followed by incubation at 65° C. for 1 hour. The resulting cDNA was used as a template for PCR (Taq polymerase, New England Biolabs, Beverly, Mass.) and transcription as described for round 1. Conditions for each round are in Table 6.

a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-IgE binding was seen starting at Round 8. Round 5, 8 and 12 pool templates were cloned using the TOPO TA cloning kit (Invitrogen, Carlsbad, Calif.) according to the manufacturer's instructions. The sequencing data revealed that the Round 8 pool had converged on a single major clone that comprised 59% of the total sequences. This major clone and three possible minimers were chosen for chemical synthesis and dissociation constants (KD) were determined. Briefly, the synthetic RNAs were 5' end labeled with $\gamma$-$^{32}$P ATP and KD values were determined using the dot blot assay and buffer conditions of 1×DPBS (w/ Ca2+ and Mg2+) (Gibco, Catalog #14040, Invitrogen, Carlsbad, Calif.). KDs were estimated fitting the data to the equation: fraction RNA bound=amplitude*(((AptConc+[h-IgE]+KD)−SQRT((AptConc+[h-IgE]+KD)2−4(AptConc*[h-IgE])))/(2*AptConc))+background. The major clone had a $K_D$ of about 800 pM. The best binding minimer, was also tested for binding to monkey IgE (m-IgE), but did not demonstrate cross-reactive binding to the monkey IgE protein. This lack of cross-reactivity for was also confirmed by ELISA. Minimers with an inverted dT on the 3' end, was used as the parent molecule for the medicinal chemistry process.

Medicinal Chemistry

Figure 9:
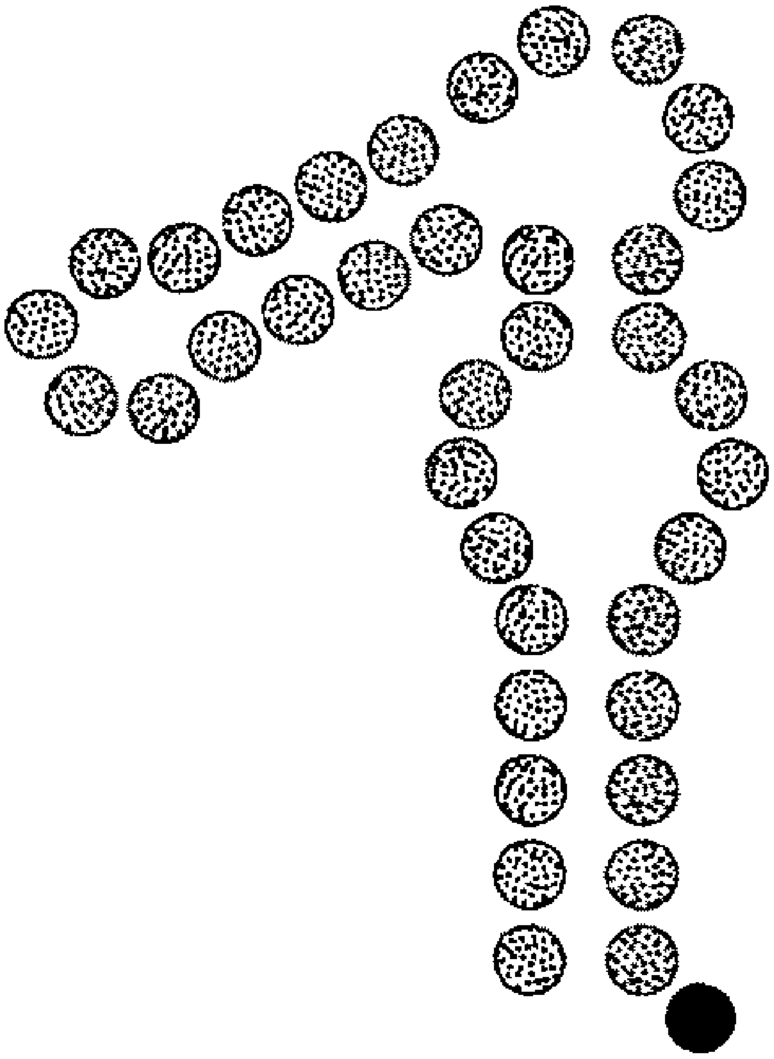
FIG. 9 is a schematic of a minimized MNA anti-IgE aptamer shown in the 5' to 3' direction having a cap on its 3'-end (dark colored ball).

The chemical composition of one of the IgE specific MNA minimers (FIG. 9) was altered to improve affinity, and potency while maintaining plasma stability of the compound.

TABLE 6

Round Summary

| Round | Pool (nM) | Platform | Negative | Buffer | Competitor | Washes | Target |
|---|---|---|---|---|---|---|---|
| 1 | 3300 | Plate | None | 1X DPBS | None | 4 × 120 μL | 24 pmols |
| 2 | 500 | Plate | Plate; BSA plate | 1X DPBS | 0.1 mg/mL tRNA; 0.1 mg/mL ssDNA | 4 × 120 μL | 24 pmols |
| 3 | 1000 | Plate | Plate; BSA plate | 1X DPBS | 0.1 mg/mL tRNA; 0.1 mg/mL ssDNA | 4 × 120 μL | 24 pmols |
| 4 | 1000 | Plate | Plate; BSA plate | 1X DPBS | 0.1 mg/mL tRNA; 0.1 mg/mL ssDNA | 4 × 120 μL | 24 pmols |
| 5 | 1000 | Plate | Plate; BSA plate | 1X DPBS | 0.1 mg/mL tRNA; 0.1 mg/mL ssDNA | 4 × 120 μL | 24 pmols |
| 6 | 1000 | Plate | Plate; BSA plate | 1X DPBS | 0.1 mg/mL tRNA; 0.1 mg/mL ssDNA | 4 × 120 μL | 24 pmols |
| 7 | 1000 | Plate | Plate; BSA plate | 1X DPBS | 0.1 mg/mL tRNA; 0.1 mg/mL ssDNA | 4 × 120 μL | 24 pmols |
| 8 | 1000 | Plate | Plate; BSA plate | 1X DPBS | 0.1 mg/mL tRNA; 0.1 mg/mL ssDNA | 4 × 120 μL | 24 pmols |
| 9 | 1000 | Plate | Plate; BSA plate | 1X DPBS | 0.1 mg/mL tRNA; 0.1 mg/mL ssDNA | 4 × 120 μL | 24 pmols |
| 10 | 1000 | Plate | Plate; BSA plate | 1X DPBS | 1.0 mg/mL tRNA; 1.0 mg/mL ssDNA | 8 × 120 μL (last wash = 15 min.) | 24 pmols |
| 11 | 500 | Plate | Plate; BSA plate | 1X DPBS | 1.0 mg/mL tRNA; 1.0 mg/mL ssDNA | 8 × 120 μL (last wash = 15 min.) | 24 pmols |
| 12 | 500 | Plate | Plate; BSA plate | 1X DPBS | 1.0 mg/mL tRNA; 1.0 mg/mL ssDNA | 8 × 120 μL (last wash = 15 min.) | 24 pmols |

MNA Aptamer Binding Analysis

Figure 10:
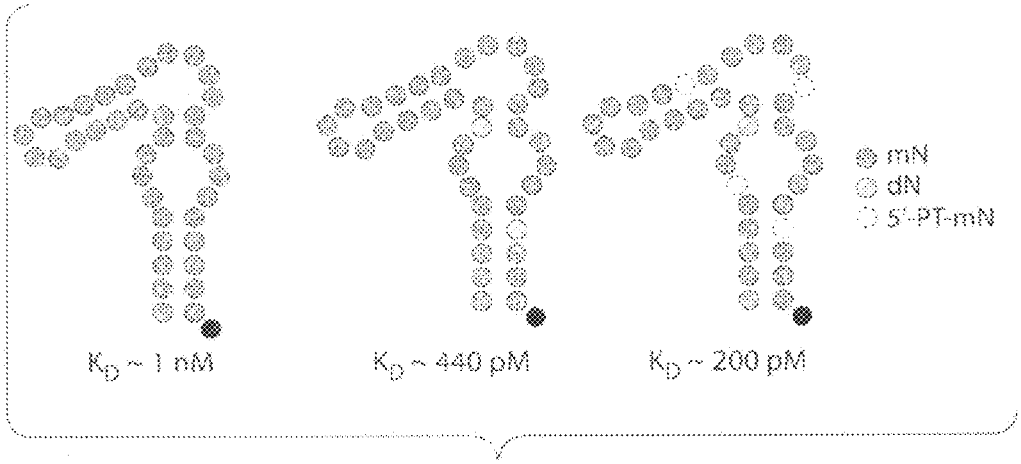
FIG. 10 is a schematic of the minimized MNA anti-IgE aptamer, the minimized MNA anti-IgE aptamer having two deoxy substitutions and the minimized MNA anti-IgE aptamer having one deoxy substitution and phosphorothioate substitutions, each shown in the 5' to 3' direction and each having a cap on its 3'-end (black colored ball).

Dot blot binding assays were performed throughout the selections to monitor the protein binding affinity of the pools. Trace 32P-endlabeled pool RNA was combined with h-IgE and incubated at room temperature for 30 minutes in DPBS buffer in a final volume of 30 μL. The mixture was applied to The process included the design, synthesis and evaluation of a series of derivatives of the minimized IgE aptamer where each derivative of the series comprised a single modification at each occurrence of a predetermined nucleotide to determine which residues tolerated substitution. The first set of modifications was the substitution of a deoxy nucleotide for each unique 2'-OMe nucleotide. In a separate round of modification, a series of derivatives was synthesized in which each derivative comprised a single phosphorothioate modification at a different internucleotide linkage position. Data generated in these initial phases of modification were used to establish a structure activity relationship (SAR) for the minimized aptamer. In a subsequent phase of modification, aptamers were synthesized and tested with composite sets of substitutions that were designed based on the initial SAR data. From the panel of composite substitutions, an aptamer 39 nucleotides in length with two 2'-OMe to 2'-deoxy substitutions introduced into its composition, was identified. In addition, a resulting modified minimized aptamer, 39 nucleotides in length with one 2'-OMe to 2'-deoxy substitution and four phosphate to phosphorothioate substitutions incorporated into its composition, was identified. As shown in FIG. 10, this deoxy/phosphorothioate modified aptamer, demonstrates increased binding affinity compared to both the minimized but unmodified parent aptamer as well as the parent minimized aptamer having two deoxy for 2'-OMe substitutions.

Serum Stability

The minimized unmodified parent and the deoxy/phosphorothioate modified aptamer were assayed to determine their stability in human, rat and monkey serums. Each aptamer was added to 1 ml of pooled serum to a final concentration of 5 μM in 90% serum. The aptamers were incubated at 37° C. with shaking and time points were taken at 0, 0.5, 1, 4, 24, 48, 72, and 98 hours. At each time point, 90 μl of stock from the incubated samples was added to 10 μl of 0.5M EDTA and frozen at −20° C. for later stability analysis using a BIACORE 2000 system.

All biosensor binding measurements were performed at 25° C. using a BIACORE 2000 equipped with a research-grade CM5 biosensor chip (BIACORE Inc., Piscataway, N.J.). Purified recombinant human IgE (Athens Research & Technology, Athens, Ga.) was immobilized to the biosensor surface using amino-coupling chemistry. To achieve this, the surfaces of two flow cells were first activated for 7 min with a 1:1 mixture of 0.1 M NHS (Nhydroxysuccinimide) and 0.4 M EDC (3-(N,Ndimethylamine) propyl-N-ethylcarbodiimide) at a flow rate of 5 μl/min. After surface activation, one flow cell was injected with 50 μg/ml of IgE at 10 μl/min for 20 min to allow for establishment of covalent bonds to the activated surface. Next, 1 M ethanolamine hydrochloride pH 8.5 was injected for 7 min at 5 μl/min to inactivate residual esters. For flow cell used as blank, 1 M ethanolamine hydrochloride pH 8.5 was injected for 7 min to inactivate residual esters without protein injection.

A set of aptamer standards was run through the prepared chip to generate a standard curve before all the time-points were analyzed. To establish a standard curve, aptamers were serially diluted (from 200 nM to 12.5 nM) into HBS-P buffer (10 mM HEPES pH7.4, 150 mM NaCl, 0.005% Surfactant 20) supplemented with 4% human serum and 50 mM EDTA. All diluted samples were injected into Biacore 2000 for binding at 20 μl/min for 5 min and wait for 3 minutes. To regenerate the chip, 1N NaCl was injected for 60 seconds at 30 μl/min. RU peak response at the end of binding phase was plotted against aptamer concentration and a standard curve was generated using a Four-Parameter logistic function. To measure the active aptamer concentration in human, rat, and monkey serums, time-point samples were diluted 22.5-fold in HBS-P to make the final serum concentration at 4% immediately prior to injection into the Biacore 2000. Functional aptamer concentrations at each serum incubation period were calculated by converting from RU response unit to concentration using standard curve generated above. As an additional quality control measure, two aptamer standards were independently tested at the end of experiment to make sure the BIACORE-measured concentrations are less than 20% deviated from standards. The minimized unmodified parent and the deoxy/phosphorothioate modified aptamer were both determined to be greater than 90% active at 98 hours in human, rat, and monkey serums.

Example 6

Aptamer Selection Using Y639L/H784A/K378R Mutant T7 RNA Polymerase

A selection was performed to identify aptamers to human von Willebrand factor (hereinafter "h-vWF") using a pool consisting of 2'-OMe ATP, GTP, and UTP nucleotides and 2'-deoxy CTP nucleotide (hereinafter "dCmD"). The selection strategy yielded high affinity aptamers specific for h-vWF.

Human vWF was purchased from EMD Biosciences, Inc. (Cat. # 681300, La Jolla. CA). Human vWF A1 domain was expressed and purified. Mutant polymerase (Y639L/H784A/K378R) was expressed and purified as described in Example 1 above. 2'-OMe ATP, GTP, and UTP nucleotides and 2'-deoxy CTP nucleotide were purchased from TriLink BioTechnologies (San Diego, Calif.).

Selection of vWF Aptamer

Pool Preparation

A template with the sequence 5'-GGGAGAATTCCGACCACAAGNNNNNNNNNNNNNNNNNNNNNNNNNNNNNNNNNNNNNNNNNNNNNNCATATGTGCGTCTACATGGATCCTCA-3' ARC4218 (SEQ ID NO 28) was synthesized using an ABI EXPEDITE™ (Applied Biosystems, Foster City, Calif.) DNA synthesizer, and deprotected by standard methods. The templates were amplified with the primers (5'-TAATACGACTCACTATAGGGAGAATTCCGACCACAAG-3') ARC4219 (SEQ ID NO 29) and (5'-TGAGGATCCATGTAGACGCACATATG-3') ARC4208 (SEQ ID NO 30) and then used as a template for in vitro transcription with T7 RNA polymerase (Y639L/H784A/K378R). Transcriptions were done using 200 mM HEPES, 40 mM DTT, 2.0 mM spermidine, 0.01 w/v % TritonX-100, 10% PEG-8000, 8 mM $MgCl_2$, 2.5 mM $MnCl_2$, 1.5 mM dCTP, 1.5 mM mUTP, 1.5 mM mGTP, 1.5 mM mATP, 1 mM GMP, 0.01 units/μL inorganic pyrophosphatase, and ~9 μg/mL mutant T7 polymerase (Y639L/H784A/K378R) and 0.3 μM template DNA to generate the ARC4218 dCmD pool.

Selection

The selection was initiated by incubating 330 pmoles ($2\times10^{14}$ molecules) of dCmD ARC4218 pool with 20 pmoles of protein bound to a HSA-blocked hydrophobic plate (Maxisorp plate, Nunc, Rochester, N.Y.) in a final volume of 1004 selection buffer (1× Dulbecco's PBS (DPBS) for 1 hr at room temperature. The well was washed five times with 200 μL DPBS to remove non-specific binders. RNA was eluted and reverse transcribed with the ThermoScript RT-PCR™ system (Invitrogen, Carlsbad, Calif.) according to the manufacturer's instructions using the primer ARC4208 (SEQ ID NO 30). The cDNA was amplified by PCR with Tag polymerase (New England Biolabs, Beverly, Mass.) according to the manufacturer's instructions using primers ARC4219 (SEQ ID NO 29) and ARC4208 (SEQ ID NO 30). Templates were transcribed as described above for pool preparation. Templates were purified by ethanol precipitation followed by a desalting step using a Micro Bio-spin column (Cat. #732-6250, Bio-Rad Laboratories, Hercules, Calif.).

All rounds were carried out with h-vWF immobilized on hydrophobic plates. The first three rounds of selection were initiated by immobilizing 10 pmoles of h-vWF and 10 pmoles of human vWF A1 domain to the surface of a Nunc Maxisorp hydrophobic plate for 30 minutes at room temperature in 100 μL of 1×DPBS. Starting at Round 4, 20 pmoles of h-vWF was immobilized on the hydrophobic plate for 2 rounds, followed by one round of 20 pmoles of human vWF A1 domain immobilized on the hydrophobic plate. The plate was washed three times with 200 μL DPBS then incubated with blocking buffer (1×DPBS, and 5% HSA) for 30 minutes. The supernatant was then removed and the wells were washed three times with 200 μL DPBS. Starting at Round 2, the pool RNA was incubated for 30 minutes at room temperature in an empty well, then for 30 minutes in a well that had been previously blocked with 100 μL blocking buffer. From Round 2 forward, non-specific competitor was added to the positive selection step (0.1 mg/mL tRNA). In all cases, the pool RNA bound to the immobilized target was reverse transcribed directly in the selection plate by the addition of reverse transcription ("RT") mix (3' primer, SEQ ID NO 30, and Thermoscript RT, Invitrogen, Carlsbad, Calif.) followed by incubation at 65° C. for 1 hour. The resulting cDNA was used as a template for PCR (Taq polymerase, New England Biolabs, Beverly, Mass.) and transcription as described for round 1. Conditions for each round are in Table 7.

TABLE 7

Round Summary

| Round | Pool (nM) | Platform | Negative | Buffer | Competitor | Washes | Target |
|---|---|---|---|---|---|---|---|
| 1 | 3300 | Plate | None | 1X DPBS | None | 5 × 200 μL | 10 pmoles vWF, 10 pmols A1 domain |
| 2 | 200 | Plate | Plate | 1X DPBS | 0.1 mg/mL tRNA | 5 × 200 μL | 10 pmoles vWF, 10 pmols A1 domain |
| 3 | 200 | Plate | Plate; HSA plate | 1X DPBS | 0.1 mg/mL tRNA | 5 × 200 μL | 10 pmoles vWF, 10 pmols A1 domain |
| 4 | 200 | Plate | Plate; HSA plate | 1X DPBS | 0.1 mg/mL tRNA | 5 × 200 μL | 20 pmols vWF |
| 5 | 200 | Plate | Plate; HSA plate | 1X DPBS | 1 mg/mL tRNA | 5 × 200 μL | 20 pmols vWF |
| 6 | 200 | Plate | Plate; HSA plate | 1X DPBS | 1 mg/mL tRNA | 5 × 200 μL | 20 pmols A1 domain |

dCmD Aptamer Binding Analysis

Dot blot binding assays were performed throughout the selections to monitor the protein binding affinity of the pools. Trace $^{32}$P-endlabeled pool RNA was combined with h-vWF and incubated at room temperature for 30 minutes in DPBS buffer in a final volume of 30 μL. The mixture was applied to a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-vWF binding was seen starting at Round 5. The dissociation constants ($K_D$) for Round 5 and Round 6 pools were determined. Briefly, the pool RNAs were 5'end labeled with γ-$^{32}$P ATP and $K_D$ values were determined using the dot blot assay and buffer conditions of 1×DPBS (w/ Ca2+ and Mg2+) (Gibco, Catalog #14040, Invitrogen, Carlsbad, Calif.). $K_D$S were estimated fitting the data to the equation: fraction RNA bound=amplitude*(((AptConc+[h-vWF]+KD)−SQRT((AptConc+[h-vWF]+KD)2−4 (AptConc*[h-vWF])))/(2*AptConc))+background. The Round 6 pool had a $K_D$ of about 2 nM. The pool was also tested for binding to the A1 domain, and had a $K_D$ of about 4 nM.

Example 7

Aptamer Selection Using Y639L/H784A/K378R Mutant T7 RNA Polymerase

A selection was performed to identify aptamers to human IgE (hereinafter "h-IgE") using a pool consisting of 2'-OMe ATP, GTP, and UTP nucleotides and 2'-deoxy CTP nucleotide (hereinafter "dCmD"). The selection strategy yielded high affinity aptamers specific for h-IgE.

Human IgE was purchased from Athens Research & Technology (Cat. #16-16-090705 Athens, Ga.). T7 RNA polymerase (Y639L/H784A/K378R) was expressed and purified as described in Example 1 above. 2'-OMe ATP, GTP, and UTP nucleotides and 2'-deoxy CTP nucleotide were purchased from TriLink BioTechnologies (San Diego, Calif.).

Selection of IgE Aptamer

Pool Preparation

A DNA template with the sequence 5'-GGGAGAATTCCGACCACAAGNNNNNNNNNNNNNNNNNNNNNNNNNNNNNNNNNNNNNNNNCATATGTGCGTCTACATGGATCCTCA-3' ARC4218 (SEQ ID NO 28) was synthesized using an ABI EXPEDITE™ (Applied Biosystems, Foster City, Calif.) DNA synthesizer, and deprotected by standard methods. The templates were amplified with the primers (5'-TAATACGACTCACTATAGGGAGAATTCCGACCACAAG-3') ARC4219 (SEQ ID NO 29) and (5'-TGAGGATCCATGTAGACGCACATATG-3') ARC4208 (SEQ ID NO 30) and then used as a template for in vitro transcription with T7 RNA polymerase (Y639L/H784A/K378R). Transcriptions were done using 200 mM HEPES, 40 mM DTT, 2.0 mM spermidine, 0.01% TritonX-100, 10% PEG-8000, 8 mM $MgCl_2$, 2.5 mM $MnCl_2$, 1.5 mM dCTP, 1.5 mM mUTP, 1.5 mM mGTP, 1.5 mM mATP, 1 mM GMP, 0.01 units/μL inorganic pyrophosphatase, and ~9 μg/mL mutant T7 polymerase (Y639L/H784A/K378R) and 0.3 μM template DNA to generate the ARC4218 dCmD pool.

Selection

The selection was initiated by incubating 330 pmoles ($2×10^{14}$ molecules) of dCmD ARC4218 pool with 20 pmoles of protein bound to a HSA-blocked hydrophobic plate (Maxisorp plate, Nunc, Rochester, N.Y.) in a final volume of 100 μL selection buffer (1× Dulbecco's PBS (DPBS) for 1 hr at room temperature. The well was washed five times with 200 μL DPBS to remove non-specific binders. RNA was eluted and reverse transcribed with the ThermoScript RT-PCR™ system (Invitrogen, Carlsbad, Calif.) according to the manufacturer's instructions using the primer ARC4208 (SEQ ID NO 30). The cDNA was amplified by PCR with Taq polymerase (New England Biolabs, Beverly, Mass.) according to the manufacturer's instructions using primers ARC4219 (SEQ ID NO 29) and ARC4208 (SEQ ID NO 30). Templates were transcribed as described above for pool preparation. Templates were purified by ethanol precipitation followed by a desalting step using a Micro Bio-spin column (Cat. #732-6250, Bio-Rad Laboratories, Hercules, Calif.).

All rounds were carried out with h-IgE immobilized on hydrophobic plates. Each round of selection was initiated by immobilizing 20 pmoles of h-IgE to the surface of a Nunc Maxisorp hydrophobic plate for 30 minutes at room temperature in 100 μL of 1×DPBS. The plate was washed three times with 200 μL DPBS then incubated with blocking buffer (1×DPBS, and 5% HSA) for 30 minutes. The supernatant was then removed and the wells were washed three times with 200 μL DPBS. Starting at Round 2, the pool RNA was incubated for 30 minutes at room temperature in an empty well, then for 30 minutes in a well that had been previously blocked with 100 μL blocking buffer. From Round 2 forward, non-specific competitor was added to the positive selection step (0.1 mg/mL tRNA). In all cases, the pool RNA bound to immobilized h-IgE was reverse transcribed directly in the selection plate by the addition of reverse transcription ("RT") mix (3' primer, SEQ ID NO 30, and Thermoscript RT. Invitrogen, Carlsbad, Calif.) followed by incubation at 65° C. for 1 hour. The resulting cDNA was used as a template for PCR (Taq polymerase, New England Biolabs, Beverly, Mass.) and transcription as described for round 1. Conditions for each round are in Table 8.

TABLE 8

| Round Summary | | | | | | | |
|---|---|---|---|---|---|---|---|
| Round | Pool (nM) | Platform | Negative | Buffer | Competitor | Washes | Target |
| 1 | 3300 | Plate | None | 1X DPBS | None | 5 × 200 μL | 20 pmols |
| 2 | 200 | Plate | Plate | 1X DPBS | 0.1 mg/mL tRNA | 5 × 200 μL | 20 pmols |
| 3 | 200 | Plate | Plate; HSA plate | 1X DPBS | 0.1 mg/mL tRNA | 5 × 200 μL | 20 pmols |
| 4 | 200 | Plate | Plate; HSA plate | 1X DPBS | 0.1 mg/mL tRNA | 5 × 200 μL | 20 pmols |
| 5 | 200 | Plate | Plate; HSA plate | 1X DPBS | 0.1 mg/mL tRNA | 5 × 200 μL | 20 pmols |
| 6 | 200 | Plate | Plate; HSA plate | 1X DPBS | 1 mg/mL tRNA | 5 × 200 μL | 20 pmols |

dCmD Aptamer Binding Analysis

Dot blot binding assays were performed throughout the selections to monitor the protein binding affinity of the pools. Trace $^{32}$P-endlabeled pool RNA was combined with h-IgE and incubated at room temperature for 30 minutes in DPBS buffer in a final volume of 30 μL. The mixture was applied to a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-IgE binding was seen starting at Round 5. The dissociation constants ($K_D$) for Round 5 and 6 pools were determined. Briefly, the pool RNAs were 5' end labeled with γ-$^{32}$P ATP and $K_D$ values were determined using the dot blot assay and buffer conditions of 1×DPBS (w/ Ca2+ and Mg2+) (Gibco, Catalog #14040, Invitrogen, Carlsbad, Calif.). $K_D$s were estimated fitting the data to the equation: fraction RNA bound=amplitude*(((AptConc+[h-IgE]+KD)−SQRT((AptConc+[h-IgE]+KD)2−4(AptConc*[h-IgE])))/(2*AptConc))+background. The Round 6 pool had a $K_D$ of about 8 nM.

Example 8

Transcription Incorporating 2'-O-Methyl ATP, CTP, GTP and 2'-O-methyl-5-Indolylmethylene UTP Nucleotides The Y639L/H784A/K378R mutant polymerase is used to incorporate 2'-O-methyl A, C, G and 2'-O-methyl-5-indolylmethylene U into a transcript using in vitro transcription. The modified uridine is depicted below as the nucleoside:

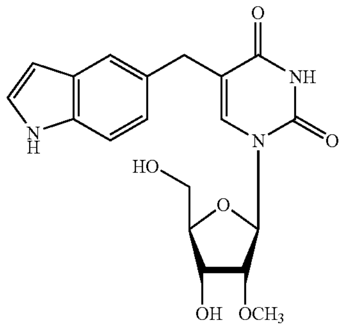

Transcriptions are performed using 200 mM HEPES, 40 mM DTT, 2 mM spermidine, 0.01% w/v TritonX-100, 10% PEG-8000, 8 mM $MgCl_2$, 2.5 mM $MnCl_2$, 1.5 mM mCTP, 1.5 mM 5-indolyl-mUTP, 1.5 mM mGTP, 1.5 mM mATP, 1 mM GMP, 0.01 units/μL inorganic pyrophosphatase, and ~9 μg/mL mutant T7 polymerase (Y639L/H784A/K378R) and 0.3 μM template DNA at 37° C. overnight to generate the transcripts consisting of 2'-OMe A. 2'-OMe G, 2'-OMe C and 2'-OMe-5-indolylmethylene U nucleotides with a single 2'-hydroxy GMP at the 5'-terminus (hereinafter "MNA-I"). Transcript yield under each condition is assayed by PAGE-gel analysis using 400 uL of reaction mixture, and transcript yield for each condition is visualized from UV-shadowing of the PAGE-gel.

Example 9

SELEX Using Y639L/H784A/K378R Mutant T7 RNA Polymerase and 2'-O-Methyl-5-Indolylmethylene Uridine SELEX against a protein target of therapeutic interest is performed using a transcription template containing multiple degenerate positions and the MNA-I transcription conditions described in the Example 7 above.

The selection step is initiated by incubating 330 pmoles (2×10$^{14}$ molecules) of the MNA-I transcript library with 20 pmoles of protein bound to a HSA-blocked hydrophobic plate (Maxisorp plate, Nunc, Rochester, N.Y.) in a final volume of 100 μL selection buffer (1× Dulbecco's PBS (DPBS) for 1 hr at room temperature. The well is washed five times with 200 μL DPBS to remove non-specific binders. RNA is reverse transcribed in the selection well using ThermoScript RT-PCR™ (Invitrogen, Carlsbad, Calif.) according to the manufacturer's instructions. The resultant cDNA is amplified by PCR with Taq polymerase (New England Biolabs, Beverly, Mass.) according to the manufacturer's instructions with a 5' primer encoding the T7 RNA polymerase promoter. The resultant transcription templates are transcribed as described above under MNA-I conditions. The resultant transcripts are purified by ethanol precipitation followed by desalting using a Micro Bio-spin column (Cat. #732-6250, Bio-Rad Laboratories, Hercules, Calif.).

After 10 rounds of SELEX, the resultant transcript library is reverse-transcribed, amplified by PCR, cloned and sequenced. Individual clones are transcribed under MNA-1 conditions and assayed for their ability to bind to and inhibit the target protein.

Example 10

Transcription Incorporating 2'-OMe TTP, 2'-OMe ATP, 2'-OMe CTP, 2'-OMe GTP Nucleotides (mTmV Compositions)

A 400 ul transcription was set up with 200 nM of a double-stranded transcription template with an internal contiguous degenerate region of 40 nucleotides, 200 mM HEPES, 40 mM DTT, 2 mM Spermidine, 0.01% Triton X-100, 1.5 mM each of 2'-OMe TTP, 2'-OMe ATP, 2'-OMe CTP, 2'-OMe GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C., precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-OMe TTP produced no observable band.

Example 11

Transcription Incorporating Deoxy TTP, 2'-OMe ATP, 2'-OMe CTP, 2'-OMe GTP Nucleotides (dTmV Compositions)

A 400 ul transcription was set up with 200 nM of a double-stranded transcription template ARC3205, 200 mM HEPES, 40 mM DTT, 2 mM Spermidine, 0.01% Triton X-100, 1.5 mM each of 2'-Deoxy TTP, 2'-OMe ATP, 2'-OMe CTP, 2'-OMe GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C. precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-Deoxy TTP produced no observable band.

Example 12

Transcription incorporating 2'-OH TTP, 2'-OMe ATP, 2'-OMe CTP, 2'-OMe GTP nucleotides (rTmV Compositions)

A 400 ul transcription was set up with 200 nM of a double-stranded transcription template with an internal contiguous degenerate region of 40 nucleotides, 200 mM HEPES. 40 mM DTT, 2 mM Spermidine, 0.01% Triton X-100, 1.5 mM each of 2'-OH TTP, 2'-OMe ATP, 2'-OMe CTP, 2'-OMe GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C., precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-OH TTP produced no observable band.

Example 13

Transcription Incorporating Deoxy UTP, 2'-OMe ATP, 2'-OMe CTP, 2'-OMe GTP Nucleotides (dUmV Compositions)

A 400 ul transcription was set up with 200 nM of a double-stranded transcription template ARC3205, 200 mM HEPES, 40 mM DTT, 2 mM Spermidine, 0.01% Triton X-100, 1.5 mM each of 2'-Deoxy UTP, 2'-OMe ATP, 2'-OMe CTP, 2'-OMe GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C., precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-Deoxy UTP produced no observable band.

Example 14

Transcription Incorporating 2'-OH UTP, 2'-OMe ATP, 2'-OMe CTP, 2'-OMe GTP Nucleotides (rUmV Compositions)

A 400 μl transcription was set up with 200 nM of a double-stranded transcription template ARC3205, 200 mM HEPES, 40 mM DTT, 2 mM Spermidine, 0.01% Triton X-100, 1.5 mM each of 2'-OH UTP, 2'-OMe ATP, 2'-OMe CTP, 2'-OMe GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C., precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-OH UTP produced no observable band.

Example 15

Transcription Incorporating 2'-OH GTP, Deoxy TTP, 2'-OMe ATP, 2'-OMe CTP Nucleotides (rGdTmM Compositions)

A 400 ul transcription was set up with 200 nM of a double-stranded transcription template ARC3205, 200 mM HEPES, 40 mM DTT, 2 mM Spermidine, 0.01% Triton X-100, 1.5 mM each of 2'-Deoxy TTP, 2'-OMe ATP, 2'-OMe CTP, 2'-OH GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. The solution was incubated overnight at 37° C., precipitated, dissolved in a denaturing loading buffer and analyzed using denaturing PAGE followed by visualization using UV shadowing upon a fluorescent screen. A band was observed that co-migrated with a corresponding MNA transcription product loaded into an adjacent well. A negative control transcription that was incubated without 2'-Deoxy TTP produced no observable band.

Example 16

Transcription Incorporating 2'-OMe QTP, 2'-OH GTP, 2'-OMe ATP, 2'-OMe CTP Nucleotides (mQrGmM Compositions)

A 400 ul transcription was set up with 200 nM of a double-stranded transcription template with an internal contiguous degenerate region of 40 nucleotides, 200 mM HEPES, 40 mM DTT, 2 mM Spermidine, 0.01% Triton X-100, 1.5 mM each of 2'-OMe QTP, 2'-OMe ATP, 2'-OMe CTP, 2'-OH GTP, 8 mM $MgCl_2$, 2.5 mM $MnCl_2$, 1 mM GMP, 10% PEG 8000, inorganic pyrophosphatase 2.5 units/ml, pH 7.5 and the K378R/Y639F/H784A mutant T7 polymerase. 2'-OMe QTP (mQ) is shown below:

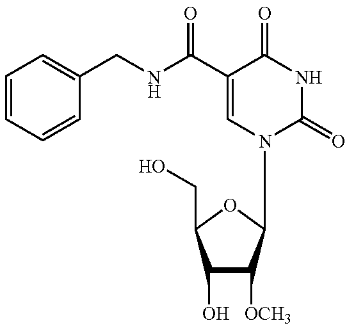

The solution was incubated overnight at 37° C., precipitated, dissolved in a denaturing loading buffer and analyzed using denaturing PAGE followed by visualization using UV shadowing upon a fluorescent screen. A clear band was observed that co-migrated with a corresponding MNA transcription product loaded into an adjacent well. A negative control transcription that was incubated without 2'-OMe QTP produced no observable band.

Example 17

Figure 11:
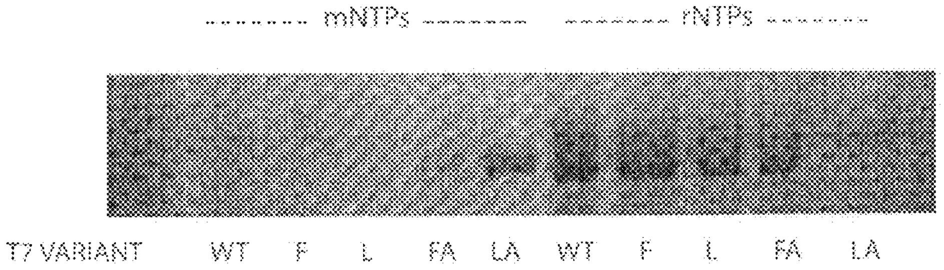
FIG. 11 is an illustration depicting the level of transcription incorporating 2'-OMe UTP, 2'-OMe ATP, 2'-OMe GTP, 2'-OMe CTP or 2'-OH NTPs using modified and wild-type T7 polymerases.

Transcription Incorporating 2'-OMe UTP, 2'-OMe ATP, 2'-OMe GTP, 2'-OMe CTP or 2'-OH NTPs Using Modified and Wild-Type T7 Polymerases 400 ul transcriptions were set up with 50 nM of a double-stranded transcription template with an internal contiguous degenerate region of 30 nucleotides, 200 mM HEPES, 40 mM DTT, 2 mM Spermidine, 0.01% Triton X-100, either 1.5 mM each of 2'-OMe UTP, 2'-OMe ATP, 2'-OMe CTP and 2'-OMe GTP or 1.5 mM each of 2'-OH UTP, 2'-OH ATP, 2'-OH CTP and 2'-OH GTP, 8 mM $MgCl_2$, 2.5 mM $MnCl_2$, 1 mM GMP, 10% PEG 8000, inorganic pyrophosphatase 2.5 units/ml, pH 7.5 and the mutant or wild-type T7 polymerase as shown below (WT is K378R, F is K378R/Y639F, L is K378R/Y639L, FA is K378R/Y639F/H784A, LA is K378R/Y639L/H784A). The solution was incubated overnight at 37° C., precipitated, dissolved in a denaturing loading buffer and analyzed using denaturing PAGE followed by visualization using UV shadowing upon a fluorescent screen. Different yields of transcription were observed as shown in FIG. 11.

The invention having now been described by way of written description and example, those of skill in the art will recognize that the invention can be practiced in a variety of embodiments and that the description and examples above are for purposes of illustration and not limitation of the following claims.

What is claimed is:

1. A method of identifying an aptamer, wherein the aptamer comprises a 2'-OMe modified nucleotide, comprising:

a) preparing a transcription reaction mixture comprising (i) a modified T7 RNA polymerase that is able to incorporate any one of a 2'-OMe modified nucleotide triphosphate (2'-OMe NTP) selected from 2'-OMe ATP, 2'-OMe GTP, 2'-OMe CTP, 2'-OMe TTP and 2'-OMe UTP, wherein the modified T7 RNA polymerase exhibits an increased ability to incorporate a 2'-modified nucleotide triphosphate (2'-modified NTP) as compared to the ability of the corresponding unmodified T7 RNA polymerase to incorporate the 2'-modified NTP, wherein the modified T7 RNA polymerase comprises mutations at amino acid positions 639 and 784 relative to the wild-type T7 RNA polymerase of SEQ ID NO: 33 and wherein the amino acid at position 639 is changed to a leucine and the amino acid at position 784 is changed to an alanine; (ii) at least one nucleic acid transcription template; and (iii) nucleotide triphosphates (NTPs), wherein the nucleotide triphosphates comprise guanidine triphosphates and wherein all of the guanidine triphosphates are 2'-OMe modified, and wherein the mixture of nucleoside triphosphates is selected from the following:

a mixture of 2'-deoxy cytidine triphosphate (2'-deoxy CTP), 2'-OMe adenosine triphosphate (2'-OMe ATP), 2'-OMe guanosine triphosphate GTP (2'-OMe GTP), and 2'-OMe uridine triphosphate (2'-OMe UTP) or 2'-OMe thymidine nucleotide triphosphates (2'-OMe TTP);

a mixture of 2'-deoxy thymidine triphosphate (2'-deoxy TTP) or 2'-deoxy uridine triphosphate (2'-deoxy UTP), and 2'-OMe adenosine triphosphate (2'-OMe ATP), 2'-OMe guanosine triphosphate GTP (2'-OMe GTP), and 2'-OMe cytidine triphosphate (2'-OMe CTP), and a mixture of 2'-OH thymidine triphosphate (2'-OH TTP) or 2'-OH uridine triphosphate (2'-OH UTP), and 2'-OMe adenosine triphosphate (2'-OMe ATP), 2'-OMe guanosine triphosphate GTP 2'-OMe GTP), and 2'-OMe cytidine triphosphate (2'-OMe CTP);

b) preparing a candidate mixture of single-stranded nucleic acids by transcribing the transcription reaction mixture under conditions whereby the modified T7 RNA polymerase incorporates at least one 2'-OMe modified nucleotide triphosphate into the nucleic acids of the candidate mixture of single-stranded nucleic acids, wherein all guanidine nucleotides of the single-stranded nucleic acids of the candidate mixture after the initial guanosine nucleotide are 2'-OMe modified;

c) contacting the candidate mixture with a target molecule;

d) partitioning the nucleic acids having an increased affinity for the target molecule from the candidate mixture, relative to the affinity of the candidate mixture for the target molecule; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified.

2. The method of claim 1, wherein the transcription reaction mixture further comprises magnesium ions, manganese ions, or both magnesium ions and manganese ions.

3. The method of claim 1, wherein the nucleic acid transcription template is at least partially double-stranded.

4. The method of claim 1, wherein the nucleic acid transcription template is fully double-stranded.

5. The method of claim 1, wherein the initial guanosine nucleotide in the resulting single-stranded nucleic acid is 2'-OMe modified.

6. The method of claim 3, wherein the at least partially double-stranded nucleic acid transcription template further comprises a leader sequence incorporated into a fixed region at the 5' end of the nucleic acid transcription template.

7. The method of claim 6, wherein the leader sequence is an all-purine leader sequence.

8. The method of claim 7, wherein the all-purine leader sequence has a length selected from at least 8 nucleotides long, at least 10 nucleotides long, at least 12 nucleotides long, and at least 14 nucleotides long.

9. The method of claim 2, wherein the transcription reaction mixture comprises both magnesium and manganese ions, and wherein the concentration of magnesium ions is between 3.0 and 3.5 times greater than the concentration of manganese ions.

10. The method of claim 2, wherein each NTP, 2'-modified NTP or 2'-OMe NTP is present at a concentration of about 0.5 mM, wherein the transcription reaction mixture comprises both magnesium and manganese ions, and wherein the concentration of magnesium ions is about 5.0 mM and the concentration of manganese ions is about 1.5 mM.

11. A method of identifying an aptamer, wherein the aptamer comprises a 2'-OMe modified nucleotide, comprising:

a) preparing a transcription reaction mixture comprising (i) a modified T7 RNA polymerase that is able to incorporate any one of a 2'-OMe modified nucleotide triphosphate (2'-OMe NTP) selected from 2'-OMe ATP, 2'-OMe GTP, 2'-OMe CTP, 2'-OMe TTP and 2'-OMe UTP, wherein the modified T7 RNA polymerase exhibits an increased ability to incorporate a 2'-modified nucleotide triphosphate (2'-modified NTP) as compared to the ability of the corresponding unmodified T7 RNA polymerase to incorporate the 2'-modified NTP, wherein the modified T7 RNA polymerase comprises mutations at amino acid positions 639 and 784 relative to the wild-type T7 RNA polymerase of SEQ ID NO: 33 and wherein the amino acid at position 639 is changed to a leucine and the amino acid at position 784 is changed to an alanine; (ii) at least one nucleic acid transcription template; (iii) nucleotide triphosphates (NTPs), wherein the nucleotide triphosphates comprise guanidine triphosphates and wherein all of the guanidine triphosphates are 2'-OMe modified, and (iv) magnesium ions, manganese ions, or both magnesium ions and manganese ions, wherein each NTP, 2'-modified NTP or 2'-OMe NTP is present at a concentration of about 1.0 mM, wherein the transcription reaction mixture comprises both magnesium and manganese ions, and wherein the concentration of magnesium ions is about 6.5 mM and the concentration of manganese ions is about 2.0 mM;

b) preparing a candidate mixture of single-stranded nucleic acids by transcribing the transcription reaction mixture under conditions whereby the modified T7 RNA polymerase incorporates at least one 2'-OMe modified nucleotide triphosphate into the nucleic acids of the candidate mixture of single-stranded nucleic acids, wherein all guanidine nucleotides of the single-stranded nucleic acids of the candidate mixture after the initial guanosine nucleotide are 2'-OMe modified;

c) contacting the candidate mixture with a target molecule;

d) partitioning the nucleic acids having an increased affinity for the target molecule from the candidate mixture, relative to the affinity of the candidate mixture for the target molecule; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified.

12. A method of identifying an aptamer, wherein the aptamer comprises a 2'-OMe modified nucleotide, comprising:

a) preparing a transcription reaction mixture comprising (i) a modified T7 RNA polymerase that is able to incorporate any one of a 2'-OMe modified nucleotide triphosphate (2'-OMe NTP) selected from 2'-OMe ATP, 2'-OMe GTP, 2'-OMe CTP, 2'-OMe TTP and 2'-OMe UTP, wherein the modified T7 RNA polymerase exhibits an increased ability to incorporate a 2'-modified nucleotide triphosphate (2'-modified NTP) as compared to the ability of the corresponding unmodified T7 RNA polymerase to incorporate the 2'-modified NTP, wherein the modified T7 RNA polymerase comprises mutations at amino acid positions 639 and 784 relative to the wild-type T7 RNA polymerase of SEQ ID NO: 33 and wherein the amino acid at position 639 is changed to a leucine and the amino acid at position 784 is changed to an alanine; (ii) at least one nucleic acid transcription template; (iii) nucleotide triphosphates (NTPs), wherein the nucleotide triphosphates comprise guanidine triphosphates and wherein all of the guanidine triphosphates are 2'-OMe modified, and (iv) magnesium ions, manganese ions, or both magnesium ions and manganese ions, wherein each NTP, 2'-modified NTP or 2'-OMe NTP is present at a concentration of about 2.0 mM, wherein the transcription reaction mixture comprises both magnesium and manganese ions, and wherein the concentration of magnesium ions is about 9.6 mM and the concentration of manganese ions is about 2.9 mM;

b) preparing a candidate mixture of single-stranded nucleic acids by transcribing the transcription reaction mixture under conditions whereby the modified T7 RNA polymerase incorporates at least one 2'-OMe modified nucleotide triphosphate into the nucleic acids of the candidate mixture of single-stranded nucleic acids, wherein all guanidine nucleotides of the single-stranded nucleic acids of the candidate mixture after the initial guanosine nucleotide are 2'-OMe modified;

c) contacting the candidate mixture with a target molecule;

d) partitioning the nucleic acids having an increased affinity for the target molecule from the candidate mixture, relative to the affinity of the candidate mixture for the target molecule; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified.

13. The method of claim 1, wherein the transcription reaction mixture further comprises GMP.

14. The method of claim 1, wherein the transcription reaction mixture further comprises a polyalkylene glycol.

15. The method of claim 14, wherein the polyalkylene glycol is polyethylene glycol.

16. The method of claim 1, wherein the transcription reaction mixture further comprises inorganic pyrophosphatase.

17. The method of claim 1, wherein the transcription reaction mixture further comprises a nucleobase modified with a side chain.

18. The method of claim 17, wherein the nucleobase is modified at a position selected from the group consisting of: the 5- and 6-positions of uridine; the 5- and 6-positions of thymidine; the 5- and 6-positions and the exocyclic amine of cytidine; the 2-, 7- and 8-positions and the exocyclic amine of adenosine; and the 7- and 8-positions and the exocyclic amine of guanosine.

19. A method of identifying an aptamer, wherein the aptamer comprises a 2'-OMe modified nucleotide, comprising:

a) preparing a transcription reaction mixture comprising (i) a modified T7 RNA polymerase that is able to incorporate any one of a 2'-OMe modified nucleotide triphosphate (2'-OMe NTP) selected from 2'-OMe ATP, 2'-OMe GTP, 2'-OMe CTP, 2'-OMe TTP and 2'-OMe UTP, wherein the modified T7 RNA polymerase exhibits an increased ability to incorporate a 2'-modified nucleotide triphosphate (2'-modified NTP) as compared to the ability of the corresponding unmodified T7 RNA polymerase to incorporate the 2'-modified NTP, wherein the modified T7 RNA polymerase comprises mutations at amino acid positions 639 and 784 relative to the wild-type T7 RNA polymerase of SEQ ID NO: 33 and wherein the amino acid at position 639 is changed to a leucine and the amino acid at position 784 is changed to an alanine; (ii) at least one nucleic acid transcription template; (iii) nucleotide triphosphates (NTPs), wherein the nucleotide triphosphates comprise guanidine triphosphates and wherein all of the guanidine triphosphates are 2'-OMe modified, and (iv) a nucleobase modified with a side chain, wherein modified nucleobase is a uracil, cytosine or thymidine, and wherein the nucleobase is modified at a position selected from the group consisting of: the 5- and 6-positions of uridine; the 5- and 6-positions of thymidine; and the 5- and 6-positions and the exocyclic amine of cytidine;

b) preparing a candidate mixture of single-stranded nucleic acids by transcribing the transcription reaction mixture under conditions whereby the modified T7 RNA polymerase incorporates at least one 2'-OMe modified nucleotide triphosphate into the nucleic acids of the candidate mixture of single-stranded nucleic acids, wherein all guanidine nucleotides of the single-stranded nucleic acids of the candidate mixture after the initial guanosine nucleotide are 2'-OMe modified;

c) contacting the candidate mixture with a target molecule;

d) partitioning the nucleic acids having an increased affinity for the target molecule from the candidate mixture, relative to the affinity of the candidate mixture for the target molecule; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified.

20. A method of identifying an aptamer, wherein the aptamer comprises a 2'-OMe modified nucleotide, comprising:

a) preparing a transcription reaction mixture comprising (i) a modified T7 RNA polymerase that is able to incorporate any one of a 2'-OMe modified nucleotide triphosphate (2'-OMe NTP) selected from 2'-OMe ATP, 2'-OMe GTP, 2'-OMe CTP, 2'-OMe TTP and 2'-OMe UTP, wherein the modified T7 RNA polymerase exhibits an increased ability to incorporate a 2'-modified nucleotide triphosphate (2'-modified NTP) as compared to the ability of the corresponding unmodified T7 RNA polymerase to incorporate the 2'-modified NTP, wherein the modified T7 RNA polymerase comprises mutations at amino acid positions 639 and 784 relative to the wild-type T7 RNA polymerase of SEQ ID NO: 33 and wherein the amino acid at position 639 is changed to a leucine and the amino acid at position 784 is changed to an alanine; (ii) at least one nucleic acid transcription template; (iii) nucleotide triphosphates (NTPs), wherein the nucleotide triphosphates comprise guanidine triphosphates and wherein all of the guanidine triphosphates are 2'-OMe modified, and (iv) a nucleobase modified with a side chain, wherein the side chain is a hydrophobic aromatic side chain;

b) preparing a candidate mixture of single-stranded nucleic acids by transcribing the transcription reaction mixture under conditions whereby the modified T7 RNA polymerase incorporates at least one 2'-OMe modified nucleotide triphosphate into the nucleic acids of the candidate mixture of single-stranded nucleic acids, wherein all guanidine nucleotides of the single-stranded nucleic acids of the candidate mixture after the initial guanosine nucleotide are 2'-OMe modified;

c) contacting the candidate mixture with a target molecule;

d) partitioning the nucleic acids having an increased affinity for the target molecule from the candidate mixture, relative to the affinity of the candidate mixture for the target molecule; and e) amplifying the increased affinity nucleic acids to yield an aptamer enriched mixture, whereby an aptamer to the target molecule comprising all 2'-OMe-modified guanidine nucleotides, except optionally one of the guanidine nucleotides of the aptamer, is identified.

21. The method of claim 20, wherein the side chain is benzyl or indolyl.

22. The method of claim 1, wherein the modified T7 RNA polymerase further comprises a mutation at amino acid position 266 relative to the wild-type T7 RNA polymerase of SEQ ID NO: 33 and wherein the amino acid at position 266 is changed to a leucine.

23. The method of claim 1, wherein the modified T7 RNA polymerase further comprises a mutation at amino acid position 378 relative to the wild-type T7 RNA polymerase of SEQ ID NO: 33 and wherein the amino acid at position 378 is changed to an arginine.

24. The method of claim 1, wherein the modified T7 RNA polymerase further comprises mutations at amino acid positions 266 and 378 relative to the wild-type T7 RNA polymerase of SEQ ID NO: 33 and wherein the amino acid at position 266 is changed to a leucine and the amino acid at position 378 is changed to an arginine.

* * * * *